US007169778B2

(12) United States Patent
Denny et al.

(10) Patent No.: US 7,169,778 B2
(45) Date of Patent: Jan. 30, 2007

(54) PTERIDINONES AS KINASE INHIBITORS

(75) Inventors: William Alexander Denny, Pakuranga (NZ); Gordon William Rewcastle, Manurewa (NZ); Ellen Dobrusin, Ann Arbor, MI (US); James Bernard Kramer, Sylvania, OH (US); Dennis Joseph McNamara, Ann Arbor, MI (US); Howard Daniel Hollis Showalter, Ann Arbor, MI (US); Peter Laurence Toogood, Ann Arbor, MI (US)

(73) Assignee: Warner-Lambert Company, Morris Plains, NJ (US)

( * ) Notice: Subject to any disclaimer, the term of this patent is extended or adjusted under 35 U.S.C. 154(b) by 125 days.

(21) Appl. No.: 10/070,530

(22) PCT Filed: Jun. 21, 2000

(86) PCT No.: PCT/US00/17037

§ 371 (c)(1),
(2), (4) Date: Mar. 6, 2002

(87) PCT Pub. No.: WO01/19825

PCT Pub. Date: Mar. 22, 2001

(65) Prior Publication Data
US 2003/0130286 A1    Jul. 10, 2003

Related U.S. Application Data

(60) Provisional application No. 60/154,095, filed on Sep. 15, 1999.

(51) Int. Cl.
*A61K 31/535*    (2006.01)
*C07D 475/00*    (2006.01)

(52) U.S. Cl. .................. 514/234.5; 544/257; 544/258; 544/259; 544/260

(58) Field of Classification Search ................ 544/118, 544/258, 259, 260; 514/234.2, 249, 234.5
See application file for complete search history.

(56) References Cited

FOREIGN PATENT DOCUMENTS

| EP | 0 837 063 A1 | 4/1998 |
| WO | WO 96/40142 A1 | 12/1996 |
| WO | WO 2002/076985 A1 * | 10/2002 |

OTHER PUBLICATIONS

Wolff, Manfred E. "Burger's Medicinal Chemistry, 5ed, Part I", John Wiley & Sons, 1995, pp. 975-977.*
Banker, G.S. et al, "Modern Pharmaceutics, 3ed.", Marcel Dekker, New York, 1996, pp. 451 and 596.*
PCT/SU00/17037 International Search Report.
M. Ott, "Zur Synthese des 4-Amino-7-oxo-7,8-dihydropteridin-N-8-beta-D-ribofuranosids-ein strukturanaloges Nucleosid des Adenosins", Chem. Ber., 1974, 339-361, vol. 107.
H. Hiroto, "Ethynylpyrimidine Derivative" Patent Abstracts of Japan, Mar. 26, 1999, vol. 1999, No. 8.
S. Tadashi, "Penicillin Derivatives" Patent Abstracts of Japan, Oct. 30, 1978, vol. 003, No. 003.

* cited by examiner

*Primary Examiner*—Deepak Rao
*Assistant Examiner*—Cecilia Jaisle
(74) *Attorney, Agent, or Firm*—Bryan C. Zielinski; Galina M. Yakovleva

(57) ABSTRACT

Disclosed are compounds of Formulae (Ia), (Ib), (Ic), (Id) wherein: W is NH, S, SO, or $SO_2$; $R^2$ is (un)substituted aryl, (un)substituted heteroaryl, or (un)substituted carbocycle or heterocycle; Q is hydrogen or lower alkyl; $R^4$ and $R^6$ are the same or different and represent hydrogen, halogen, lower alkyl, lower alkoxy, (un)substituted aryl, (un)substituted heteroaryl, (un)substituted arylalkyl or (un)substituted heteroarylalkyl; and $R^8$ is hydrogen, lower alkyl or an (un) substituted carbocyclic group containing from 3–7 members, up to two of which members are optionally hetero atoms selected from oxygen and nitrogen; or $R^8$ is (un) substituted aryl, (un)substituted heteroaryl, (un)substituted arylalkyl or (un)substituted heteroarylalkyl. These compounds are useful for treating cell proliferative disorders, such as cancer and restenosis. These compounds are potent inhibitors of cyclin-dependent kinases (cdks) and growth factor-mediated kinases. The present invention also provides a method of treating cell proliferative disorders. Also provided by the present invention is a pharmaceutically acceptable composition containing a compound of Formula (I).

7 Claims, No Drawings

PTERIDINONES AS KINASE INHIBITORS

CROSS-REFERENCE TO RELATED APPLICATIONS

This application claims the benefit of PCT/US00/17037, filed Jun. 21, 2000 and of U.S. Provisional Application No. 60/154,095, filed Sep. 15, 1999.

BACKGROUND OF THE INVENTION

1. Field of the Invention

This invention relates to 8H-pteridine-7-ones, tetrahydropteridin-7-ones, 5H,8H-pteridine-6,7-diones and pteridine-7-ureas that inhibit cyclin-dependent serine/threonine kinase, Wee 1 tyrosine kinase, and growth factor-mediated tyrosine kinase enzymes, and as such are useful to treat cell proliferation diseases and disorders. These include cardiovascular diseases including atherosclerosis and restenosis; cancer; angiogenesis; viral infections including DNA viruses such as herpes and RNA viruses such as HIV; fungal infections; type 1 diabetes and diabetic neuropathy and retinopathy; multiple sclerosis; glomerulonephritis; neurodegenerative diseases including Alzheimer's disease; autoimmune diseases such as psoriasis, rheumatoid arthritis, lupus; organ transplant rejection and host versus graft disease; Gout; polycystic kidney disease; and inflammation including inflammatory bowel disease.

2. Summary of the Related Art

Cell cycle kinases are naturally occurring enzymes involved in regulation of the cell cycle (Meijer L., "Chemical Inhibitors of Cyclin-Dependent Kinases", *Progress in Cell Cycle Research*, 1995; 1:351–363). Typical enzymes include serine/threonine kinases such as the cyclin-dependent kinases (cdk) cdk1, cdk2, cdk4, cdk5, cdk6 as well as tyrosine kinases involved in cell cycle regulation such as Wee 1 kinase. Increased activity or temporally abnormal activation or regulation of these kinases has been shown to result in development of human tumors and other proliferative disorders. Compounds that inhibit cdks, either by blocking the interaction between a cyclin and its kinase partner, or by binding to and inactivating the kinase, cause inhibition of cell proliferation, and are thus useful for treating tumors or other abnormally proliferating cells.

Several compounds that inhibit cdks have demonstrated preclinical anti-tumor activity. For example, flavopiridol is a flavonoid that has been shown to be a potent inhibitor of several types of breast and lung cancer cells (Kaur, et al., *J. Natl. Cancer Inst.*, 1992;84:1736–1740; *Int. J. Oncol.*, 1996; 9:1143–1168). The compound has been shown to inhibit cdk2 and cdk4. Olomoucine [2-(hydroxyethylamino)-6-benzylamine-9-methylpurine] is a potent inhibitor of cdk2 and cdk5 (Vesely, et al., *Eur. J. Biochem.*, 1994;224:771–786), and has been shown to inhibit proliferation of approximately 60 different human tumor cell lines used by the National Cancer Institute (NCI) to screen for new cancer therapies (Abraham, et al., *Biology of the Cell*, 1995;83:105–120). More recently, the purvalanol class of cdk inhibitors have emerged as more potent derivatives of the olomoucine class of compounds (Gray, N. S., et al., *Science*, 1998;281: 533–538).

In addition, tyrosine kinases are a class of enzymes that catalyze the transfer of the terminal phosphate of adenosine triphosphate (ATP) to tyrosine residues on protein substrates. Tyrosine kinases are essential for the propagation of growth factor signal transduction leading to cell cycle progression, cellular proliferation, differentiation, and migration. Tyrosine kinases include cell surface growth factor receptor tyrosine kinases such as FGFr and PDGFr; as well as nonreceptor tyrosine kinases, including c-src and lck. Inhibition of these enzymes have been demonstrated to cause antitumor and antiangiogenesis activity (Hamby, et al., *Pharmacol. Ther.*, 1999;82(2–3):169–193).

Despite the progress that has been made, the search continues for small molecular weight compounds that are orally bioavailable and useful for treating a wide variety of human tumors and other proliferative disorders, including restenosis, angiogenesis, diabetic retinopathy, psoriasis, surgical adhesions, macular degeneration, and atherosclerosis. The present invention provides such compounds, their pharmaceutical formulations, and their use in treating proliferative disorders.

SUMMARY OF THE INVENTION

This invention provides novel pteridine compounds which function as inhibitors of cell cycle regulatory kinases such as the cyclin dependent kinases and Wee 1, as well as the growth factor-mediated tyrosine kinases. Thus, these compounds are useful to treat cell proliferative disorders such as atherosclerosis and restenosis; cancer; angiogenesis; viral infections including DNA viruses such as herpes and RNA viruses such as HIV, fungal infections; type 1 diabetes and diabetic neuropathy and retinopathy; multiple sclerosis; glomerulonephritis; neurodegenerative diseases including Alzheimer's disease; autoimmune diseases such as psoriasis, rheumatoid arthritis, lupus; organ transplant rejection and host Vs. graft disease; Gout; polycystic kidney disease; and inflammation including inflammatory bowel disease. Accordingly, a broad embodiment of the invention is directed to compounds of general Formulas Ia, Ib, Ic, Id, and Ie:

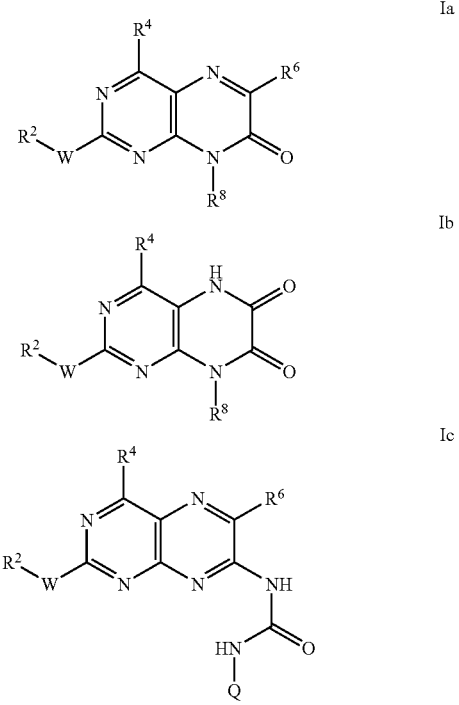

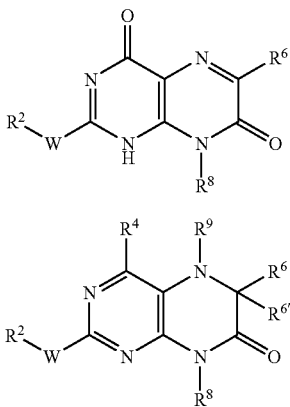

and pharmaceutically acceptable salts, esters, amides and prodrugs thereof, wherein:

W is NH, O, S, SO, or $SO_2$;

$R^2$ is:

$C_1$–$C_{10}$ alkyl, $C_2$–$C_{10}$ alkenyl, $C_2$–$C_{10}$ alkynyl, $C_3$–$C_{10}$ cycloalkyl, $(CH_2)_n$-aryl, $COR^4$, $(CH_2)_n$-heteroaryl, and $(CH_2)_n$-heterocyclicyl, wherein each of the foregoing alkyl, alkenyl, alkynyl, cycloalkyl, aryl, heteroaryl, and heterocyclicyl groups can be unsubstituted or substituted with from 1 to 5 substituent groups selected from:
(a) halogen
(b) amino, alkylamino, and dialkylamino
(c) alkoxy, aminoalkoxy, alkylaminoalkoxy, and dialkylaminoalkoxy
(d) phenyl, substituted phenyl, phenoxy, and substituted phenoxy
(e) hydroxy
(f) thio, alkylthio
(g) cyano
(h) nitro
(i) alkanoyl, aminoalkanoyl, alkylaminoalkanoyl, and dialkylaminoalkanoyl
(j) aminocarbonyl, alkylaminocarbonyl, and dialkylaminocarbonyl
(k) amino-$C_3$–$C_7$ cycloalkylcarbonyl, alkylamino-$C_3$–$C_7$ cycloalkylcarbonyl, and dialkylamino-$C_3$–$C_7$ cycloalkylcarbonyl
(l) COZ, $CO_2Z$, SOZ, $SO_2Z$, and $PO_3Z$, where Z is hydrogen, hydroxy, alkoxy, lower alkyl, substituted alkyl, amino, alkylamino, dialkylamino, piperidinyl, substituted piperidinyl, morpholinyl, substituted morpholinyl, piperazinyl, and substituted piperazinyl
(m) a carbocyclic group containing from 3 to 7 ring members, one or two of which may be a heteroatom selected from O or N, and wherein the carbocyclic group may be substituted with one, two, or three substituent groups selected from:
(1) halogen
(2) hydroxy
(3) alkyl, aminoalkyl, alkyl and dialkylaminoalkyl
(4) trifluoromethyl
(5) alkoxy
(6) amino, alkylamino, dialkylamino, alkanoylamino
(7) COZ, $CO_2Z$, SOZ, $SO_2Z$, or $PO_3Z$
(8) aryl
(9) heteroaryl
(10) $(CH_2)_n$ morpholino
(11) $(CH_2)_n$ piperazinyl
(12) $(CH_2)_n$ piperadinyl
(13) $(CH_2)_n$ tetrazolyl
(n) trifluoromethyl;

$R^4$, $R^6$, $R^{6'}$, and $R^9$ are:
(a) the same or different and are independently hydrogen, halogen, lower alkyl, or lower alkoxy, substituted alkyl, $(CH_2)_n$-alkenyl, $(CH_2)_n$-alkynyl, $(CH_2)_n$-cyano, amino, aminoalkoxy, phenoxy, hydroxy, trifluoromethyl, mono- or dialkylamino, mono- or dialkylaminoalkoxy, thiol, thioalkyl, nitrile, nitro, carboxylic acid, carboxylic acid esters, carboxamides, $SO_3Z$, $PO_3Z$, aminoalkanoyl, aminocarbonyl, amino-$C_3$–$C_7$-cycloalkylcarbonyl, and N-mono- or N,N-dialkylaminocarbonyl;
(b) the same or different and are independently $(CH_2)_n$-aryl, $(CH_2)_n$-heteroaryl, arylalkyl, or heteroarylalkyl, wherein each aryl and heteroaryl is unsubstituted or substituted with up to five groups selected from halogen, hydroxy, lower alkyl, trifluoromethyl, substituted alkyl, alkenyl, substituted alkenyl, alkynyl, substituted alkynyl, lower alkoxy, amino, mono- or dialkylamino, trifluoromethyl, thiol, thioalkyl, nitrile, nitro, carboxylic acid, carboxylic acid esters, carboxamides, $SO_3Z$, and $PO_3Z$;

$R^8$ is:
(a) hydrogen, lower alkyl, substituted alkyl, $(CH_2)_n$-alkenyl, $(CH_2)_n$-alkynyl, or a $(CH_2)_n$-carbocyclic group containing from 3–7 members, up to two of which members are hetero atoms selected from oxygen and nitrogen, wherein the carbocyclic group is unsubstituted or substituted with one, two or three groups selected from the group consisting of halogen, hydroxy, lower alkyl, lower alkoxy, acetoxy, mono- or dialkylamino, aryl and heteroaryl;
(b) $(CH_2)_n$-aryl, $(CH_2)_n$-heteroaryl, arylalkyl, or heteroarylalkyl, wherein each aryl or heteroaryl is unsubstituted or substituted with up to five groups selected from the group consisting of halogen, hydroxy, lower alkyl, substituted alkyl, lower alkoxy, amino, mono- or dialkylamino and trifluoromethyl, alkenyl, substituted alkenyl, alkynyl, substituted alkynyl, thiol, thioalkyl, nitrile, nitro, carboxylic acid, carboxylic acid esters, carboxamides, $SO_3Z$, and $PO_3Z$; and n is an integer from 0 to 6;

provided that $R^8$ is other than hydrogen or $C_1$–$C_3$ alkyl when $R^2$ is metyl, ethyl, or acetyl.

It is noted that when $R^4$ in Formula Ia is OH, then Ia is the tautomer of Id.

It will also be noted that $R^6$ and $R^{6'}$ can be taken together to form 6-keto compounds such as Formula Ib.

The present invention also provides a pharmaceutically acceptable composition that comprises a compound of Formulas Ia, Ib, Ic, Id, and Ie together with a pharmaceutically acceptable carrier, diluent, or excipient.

The present invention also provides methods for inhibiting cell cycle regulatory kinases such as cyclin-dependent kinase, Wee 1 and growth factor-mediated tyrosine kinase enzymes comprising administering a pteridine of the above formulas to a mammal.

The present invention also provides a method of treating subjects suffering from diseases caused by cellular proliferation. The method comprises inhibiting proliferation of tumorigenic cells of epithelial origin and vascular smooth muscle proliferation, and/or cellular migration, by administering a therapeutically effective amount of a compound of Formulas Ia, Ib, Ic, Id, and Ie to a subject in need of treatment.

The invention also provides the above compounds useful in the diagnosis and treatment of cancer, psoriasis, vascular smooth muscle cell proliferation associated with atherosclerosis and postsurgical vascular stenosis and restenosis in mammals.

The present invention also provides a method of treating subjects suffering from diseases caused by DNA tumor viruses such as herpes viruses comprising administering a pteridine of the above formulas.

DETAILED DESCRIPTION OF THE INVENTION

The pteridines provided by this invention are those described by the general Formulas Ia, Ib, Ic, Id, and Ie set forth above, and the pharmaceutically acceptable salts, esters, amides, and prodrugs thereof Preferred among the compounds of Formulas Ia, Ib, Ic, Id, and Ie are the compounds of Formula II:

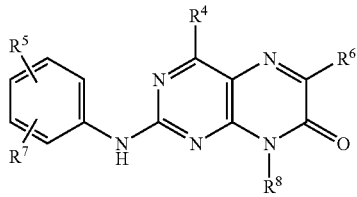

II wherein $R^4$, $R^6$, and $R^8$ are as defined above, and $R^5$ and $R^7$ are:

(a) the same or different and are selected from hydrogen, halogen, amino, aminoalkoxy, lower alkoxy, phenoxy, hydroxy, thiol, thioalkyl, nitrile, nitro, phenyl, substituted phenyl, heteroaryl, halogen, amino, alkylamino, dialkylamino, trifluoromethyl, mono- or dialkylamino, mono- or dialkylaminoalkoxy, aminoalkanoyl, aminocarbamoyl, amino-$C_3$–$C_7$-cycloalkylcarbonyl, N-mono- or N,N-dialkylaminocarbonyl, or $CO_2Z$, $COZ$, $SO_2Z$, or $PO_3Z$ where Z is H lower alkyl, substituted alkyl, hydroxy, alkoxy, amino, mono- or dialkylamino, piperidinyl, morpholinyl or piperazinyl (substituted or unsubstituted);

(b) lower alkyl unsubstituted or substituted with one or two groups selected from lower alkoxy, halogen, amino, hydroxy, mono- or dialkylamino, aryl or a carbocyclic group containing from 3–7 members, up to two of which members are hetero atoms selected from oxygen and nitrogen, wherein the carbocyclic group is unsubstituted or substituted with one, two or three groups independently selected from the group consisting of halogen, hydroxy, lower alkyl, lower alkoxy, amino, or mono- or dialkylamino; or (c) a carbocyclic group containing from 3–7 members, up to two of which members are hetero atoms selected from oxygen and nitrogen, wherein the carbocyclic group is unsubstituted or substituted with one, two or three groups independently selected from the group consisting of halogen, hydroxy, lower alkyl, branded alkyl, trifluoromethyl, lower alkyl, amino, mono- or dialkylamino, aryl, heteroaryl, carbxylic acid, carboxamide, carboxylic acid ester, morpholinoalkyl, piperazinylalkyl, piperadinylalkyl, tetrazolylalkyl, aminoalkyl, and aminoalkanoyl.

Preferred compounds of Formula II are those in which:

(a) $R^4$ is hydrogen;

(b) $R^6$ is hydrogen, halogen, substituted or unsubstituted alkyl, aryl or heteroaryl, where such aryl or heteroaryl is unsubstituted or substituted with one to five groups selected from hydroxy, amino, carboxy, NH—CHO, halogen, lower alkyl, or lower alkoxy;

(c) $R^8$ is lower alkyl or a carbocyclic group containing from 3–7 members;

(d) $R^7$ is hydrogen or halogen; and (e) $R^5$ is in the 4-position (ie, para), and is selected from halogen, mono- or dialkylaminoalkoxy, N-mono- or N,N-dialkylcarbamoyl, $(CH_2)_n$-carboxylic acid, $(CH_2)_n$-carboxylic acid ester or amide, $(CH_2)_n$—$SO_2Z$, $(CH_2)_n$—$PO_3Z$, or a carbocyclic group containing from 3–7 members, up to two of which members are hetero atoms selected from oxygen and nitrogen, wherein the carbocyclic group is unsubstituted or substituted with lower alkyl, acyl, morpholinoalkyl, piperazinylalkyl, piperadinylalkyl, tetrazolylalkyl, aminoalkyl, and alkanoylamino.

More preferred compounds of Formula II are those wherein:

(a) $R^4$ is hydrogen;

(b) $R^8$ is methyl, ethyl, or cyclopentyl;

(c) $R^7$ is hydrogen;

(d) $R^5$ is in the 4-position and is selected from mono- or dialkylaminoalkoxy, N-mono- or N,N-dialkylcarbamoyl, or a carbocyclic group containing from 3–7 members, up to two of which members are hetero atoms selected from oxygen and nitrogen, wherein the carbocyclic group is unsubstituted or substituted with lower alkyl, acyl, morpholinoalkyl, piperazinylalkyl, piperadinylalkyl, tetrazolylalkyl, aminoalkyl, and alkanoylamino; and (e) $R^6$ is hydrogen or methyl, phenyl or 4-pyridyl, wherein phenyl and pyridyl groups are unsubstituted or substituted with up to five groups selected from the group consisting of chlorine, fluorine, hydroxy, methyl, amino, carboxy, and methoxy.

In addition, the present invention also encompasses preferred compounds of the Formula III:

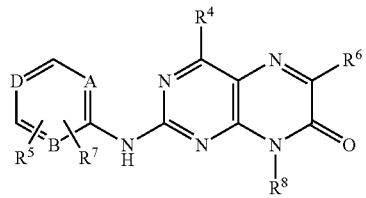

III wherein $R^4$, $R^5$, $R^6$, $R^7$, and $R^8$ are as defined above; and A, B, and D are the same or different and represent N or CH, provided that at least one of A, B or D is CH.

Preferred compounds of Formula III are those in which only one of A, B, and D is N; $R^5$ and $R^7$ are hydrogen; $R^8$ is lower alkyl or a carbocyclic group containing from 3–7 members; $R^4$ is hydrogen and $R^6$ is hydrogen, aryl, or pyridyl unsubstituted or substituted with up to five groups selected from hydroxy, amino, carboxy, halogen, lower alkyl, or lower alkoxy.

More preferred compounds of Formula III are those in which D is N; A and B are CH; $R^4$ is hydrogen; $R^6$ is hydrogen, aryl, or pyridyl unsubstituted or substituted with up to four groups selected from halogen, hydroxy, lower alkyl, and lower alkoxy; and $R^8$ is methyl, ethyl, or cyclopentyl.

In addition, the present invention also provides compounds of the Formula IVa and IVb:

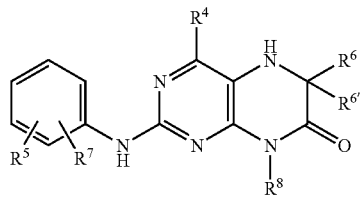

IVa

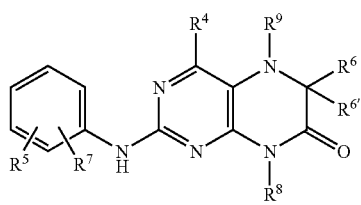

IVb wherein $R^4$ and $R^8$ are as defined above for Formulas Ia, Ib, Ic, and Id; and $R^5$ and $R^7$ are defined as defined above for Formula II; $R^9$ is H, OH, $NH_2$, lower alkyl, substituted alkyl, $(CH_2)_n$-alkenyl, or $(CH_2)_n$-alkynyl; when $R^6$ and $R^{6\prime}$ are taken together as C=O (IVc) or each is H for IVd.

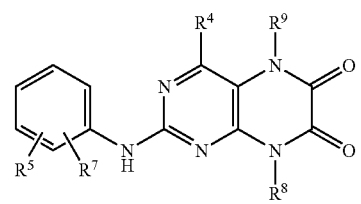

IVc

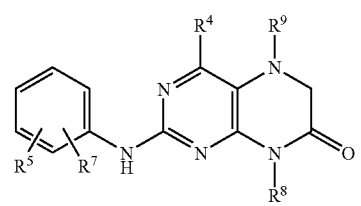

IVd

Preferred compounds of Formula IVc when $R^9$ is H or methyl are those in which $R^4$ is hydrogen; $R^8$ is lower alkyl or a carbocyclic group containing from 3–7 members; $R^7$ is hydrogen; and $R^5$ is in the 4-position and represents a carbocyclic group containing from 3–7 members, up to two of which members are hetero atoms selected from oxygen and nitrogen, where the carbocyclic group is unsubstituted or substituted with lower alkyl.

More preferred compounds of Formula IVc are those wherein $R^8$ is cyclopentyl and $R^5$ is in the 4-position and represents morpholin-4-yl, 4-piperazin-1-yl, or 4-methylpiperazin-1-yl.

In addition, the present invention also provides compounds of Formula V:

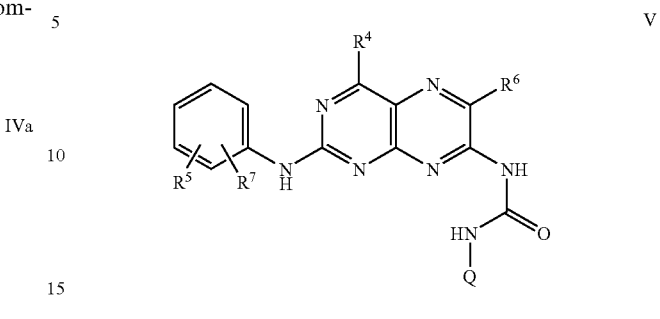

V wherein $R^4$, $R^6$, and Q are as defined above for Formulas Ia, Ib, Ic, Id, and Ie; and $R^5$ and $R^7$ are defined as defined above for Formula II.

Preferred compounds of Formula V are those wherein $R^4$ is hydrogen, $R^6$ is aryl, pyridyl, hydrogen or lower alkyl, Q is lower alkyl, $R^5$ is halogen or hydrogen and $R^7$ is lower alkyl, unsubstituted or substituted with a carbocyclic group containing from 3–7 members, up to two of which members are hetero atoms selected from oxygen and nitrogen, wherein the carbocyclic group is unsubstituted or substituted with lower alkyl, acyl, amino, or mono- or dialkylamino.

More preferred compounds of Formula V are those wherein $R^7$ is lower alkyl unsubstituted or substituted with morpholine, piperidine, piperazine, or pyrrolidine, each of which is unsubstituted or independently substituted with lower alkyl, amino or mono- or dialkylamino.

By "alkyl", "lower alkyl", and "$C_1$–$C_{10}$ alkyl" in the present invention is meant straight or branched chain alkyl groups having 1–10 carbon atoms, such as preferably $C_1$–$C_6$, methyl, ethyl, n-propyl, isopropyl, n-butyl, sec-butyl, tert-butyl, pentyl, 2-pentyl, isopentyl, neopentyl, hexyl, 2-hexyl, 3-hexyl, decyl, octyl, and 3-methylpentyl. These groups may be substituted, for instance with halo, amino, alkyl, and dialkylamino, hydroxy and the like. Examples include chloromethyl, 2-amino ethyl, and 3-dimethyl-aminopropyl.

"Alkenyl" and "alkynyl" mean $C_2$–$C_{10}$ carbon chains having one or two nonadjacent double or triple bonds, respectively. Preferred are $C_2$–$C_6$ alkenyl such as 3-butenyl and 1-methyl-3-pentenyl. Typical $C_2$–$C_6$ alkynyl groups include 2-propynyl and 1,1-dimethyl-3-butynyl. Substituted alkenyl and alkynyl groups include 4,4-dibromo-2-pentenyl and 3-amino-5-hexynyl.

By "alkoxy", "lower alkoxy", and "$C_1$–$C_{10}$ alkoxy" in the present invention is meant straight or branched chain alkoxy groups having 1 to 10 carbon atoms, preferably 1–6 carbon atoms bonded through an oxygen atom, such as, for example, methoxy, ethoxy, n-propoxy, isopropoxy, n-butoxy, sec-butoxy, tert-butoxy, pentoxy, 2-pentyloxy, isopentoxy, neopentoxy, hexoxy, 2-hexoxy, 3-hexoxy, and 3-methylpentoxy. These alkoxy groups may be substituted, for example with amino, alkylamino, and dialkylamino groups. Examples include aminomethoxy, 2-(methylamino)ethoxy, and 4-(dimethylamino)butoxy.

The term "alkanoyl" means an alkyl group bonded through a carbonyl moiety. Examples include acetyl and pentanoyl. "Aminoalkanoyl" means the alkyl group is substituted with an amino group. Examples include aminoacetyl and 3-aminohexanoyl. "Alkylaminoalkanoyl" means an aminoalkanoyl group wherein the amine is substituted with a $C_1$–$C_{10}$ alkyl group, and includes methylaminoacetyl and 4-(isobutylamino)-octanoyl. "Dialkylaminoalkanyl" means an N,N-di-substituted aminoalkanoyl group such as diisopropylaminoacetyl.

The term "aminocarbonyl" means an amino group bonded through a carbonyl group, for example aminoformyl. "Alkylaminocarbonyl" includes groups such as methylaminoformyl, and "dialkylaminocarbonyl" includes groups such as diethylaminoformyl.

By the term "halogen" in the present invention is meant fluorine, bromine, chlorine, and iodine.

"Alkylthio" means the above $C_1$–$C_{10}$ alkyl groups bonded through a sulfur atom. Examples include methylthio, isopropylthio, decylthio, and 1,1-dimethylbutylthio.

By "aryl" is meant an aromatic carbocyclic group having a single ring (e.g., phenyl), multiple rings (e.g., biphenyl), or multiple condensed rings in which at least one is aromatic, (e.g., 1,2,3,4-tetrahydronaphthyl, naphthyl, anthryl, or phenanthryl), which can be mono-, di-, trisubstituted or tetrasubstituted with, e.g., halogen, lower alkyl, lower alkoxy, lower alkylthio, trifluoromethyl, lower acyloxy, aryl, heteroaryl, amino, and hydroxy. A preferred aryl is phenyl and substituted phenyl, including 2,6-dichlorophenyl, 3-methoxyphenyl, 2,3-difluoro-4-methoxy-5-trifluoromethylphenyl, 2-chloro-6-bromophenyl, 3,5-diethoxyphenyl, 2,6-dimethylphenyl, 2,6-dichloro-3-hydroxyphenyl, 2,6-dichloro-4-hydroxyphenyl, 3-aminophenyl, 4-aminophenyl, 2-chloro-6-methoxyphenyl, 2-chloro-6-hydroxyphenyl, 2,6-dichloro-4-aminophenyl, and 2,6-dichloro-3-aminophenyl.

By "heteroaryl" is meant one or more aromatic ring systems of 5-, 6-, or 7-members containing at least one and up to four heteroatoms selected from nitrogen, oxygen, or sulfur. Such heteroaryl groups include, for example, thienyl, furanyl, thiazolyl, imidazolyl, (is)oxazolyl, tetrazolyl, pyridyl, pyridonyl, pyrimidinyl, pyrazole, (iso)quinolinyl, napthyridinyl, phthalimidyl, benzimidazolyl, benzoxazolyl. Preferred heteroaryls of the present invention are pyridyl, phthalimidyl and tetrazolyl. The heteroaryl group can be substituted with one, two, three, or four of the groups mentioned above for aryl, such as 2,3,4,6-tetrachloropyridyl and 2-methoxy-3-trifluoromethylthien-4-yl.

A "carbocyclic group" means a nonaromatic cyclic ring or fused rings having from 3 to 7 ring carbon members. Examples include cyclopropyl, cyclobutyl, and cycloheptyl. These rings may be substituted with one or more of the substituent groups mentioned above for aryl, for example alkyl, halo, amino, hydroxy, and alkoxy. Typical substituted carbocyclic groups include 2-chlorocyclopropyl, 2,3-diethoxycyclopentyl, and 2,2,4,4-tetrafluorocyclohexyl. The carbocyclic group may contain one or two heteroatoms selected from oxygen, sulfur, and nitrogen, and such ring systems are referred to as "heterocyclicyl". Examples include pyranyl, tetrahydrofuranyl, and dioxanyl. These heterocyclicyl groups may be substituted with up to four of the substituent groups mentioned for aryl to give groups such as 3-chloro-2-dioxanyl, and 3,5-dihydroxymorpholino.

The term "cancer" includes, but is not limited to, the following cancers: breast, ovary, cervix, prostate, testis, esophagus, glioblastoma, neuroblastoma, stomach, skin, keratoacanthoma, lung, epidermoid carcinoma, large cell carcinoma, adenocarcinoma, bone, colon, adenocarcinoma, adenoma, pancreas, adenocarcinoma, thyroid, follicular carcinoma, undifferentiated carcinoma, papillary carcinoma, seminoma, melanoma, sarcoma, bladder carcinoma, liver carcinoma, and biliary passages, kidney carcinoma, myeloid disorders, lymphoid disorders, Hodgkins, hairy cells, buccal cavity, and pharynx (oral), lip, tongue, mouth, pharynx, small intestine, colon-rectum, large intestine, rectum, brain, and central nervous system; and leukemia.

The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See, for example, Berge S. M. et al., "Pharmaceutical Salts," *J. Pharm. Sci.*, 1977;66:1–19 which is incorporated herein by reference.)

Examples of pharmaceutically acceptable, non-toxic esters of the compounds of this invention include $C_1$–$C_6$ alkyl esters, wherein the alkyl group is a straight or branched, substituted or unsubstituted, $C_5$–$C_7$ cycloalkyl esters, as well as arylalkyl esters such as benzyl and triphenylmethyl. $C_1$–$C_4$ alkyl esters are preferred, such as methyl, ethyl, 2,2,2-trichloroethyl, and tert-butyl. Esters of the compounds of the present invention may be prepared according to conventional methods.

Examples of pharmaceutically acceptable, non-toxic amides of the compounds of this invention include amides derived from ammonia, primary $C_1$–$C_6$ alkyl amines and secondary $C_1$–$C_6$ dialkyl amines, wherein the alkyl groups are straight or branched. In the case of secondary amines, the amine may also be in the form of a 5- or 6-membered heterocycle containing one nitrogen atom. Amides derived from ammonia, $C_1$–$C_3$ alkyl primary amines and $C_1$–$C_2$ dialkyl secondary amines are preferred. Amides of the compounds of the invention may be prepared according to conventional methods.

The term "prodrug" refers to compounds that are rapidly transformed in vivo to yield the parent compound of the above formulae, for example, by hydrolysis in blood. A thorough discussion of prodrugs is provided in T. Higuchi and V. Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are hereby incorporated by reference.

Representative compounds of the invention are shown below in Table 1.
TABLE 1
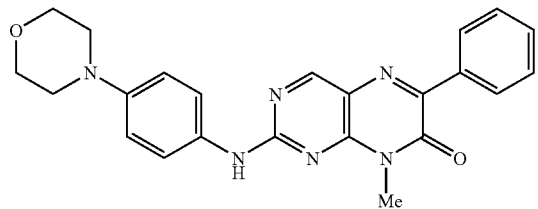
1
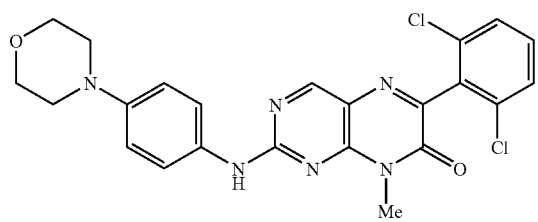
2
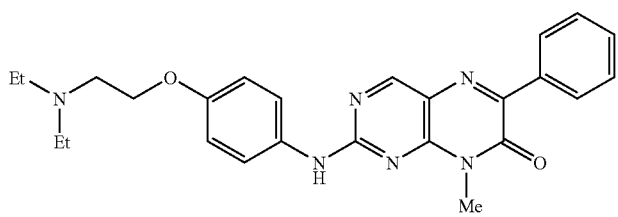
3
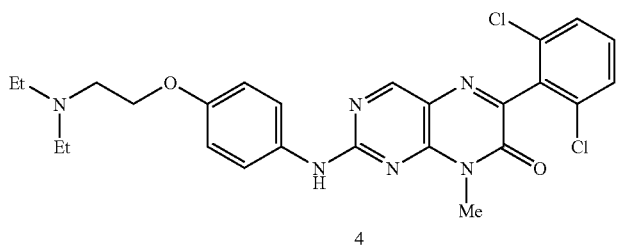
4
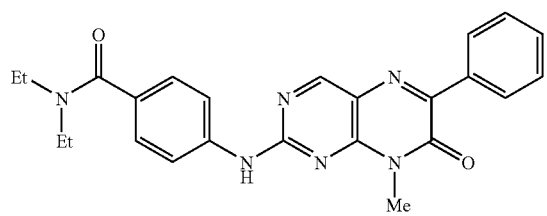
5

TABLE 1-continued
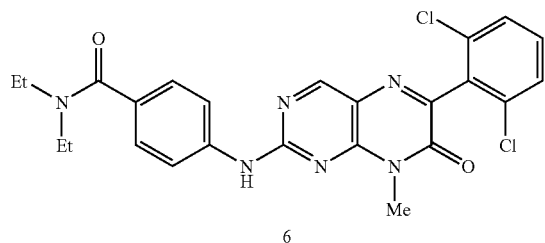
6
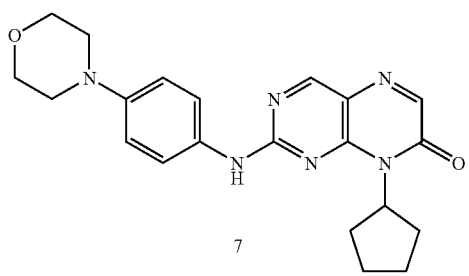
7
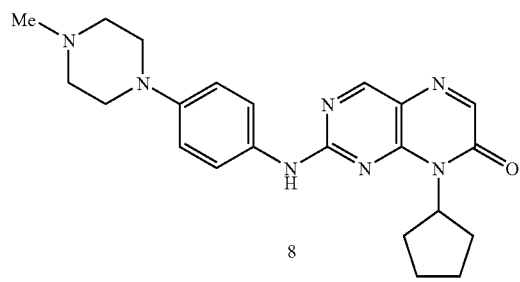
8
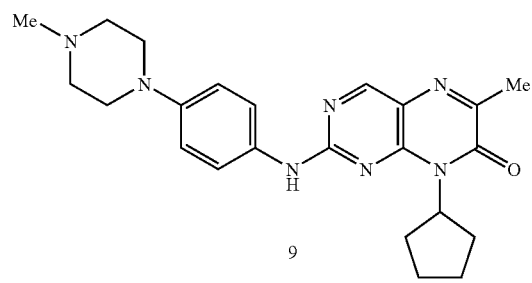
9
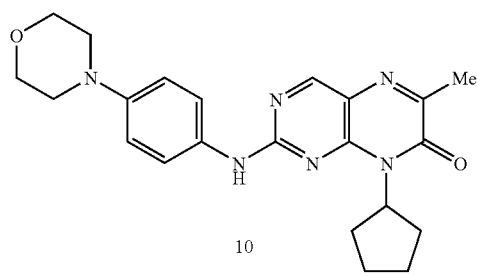
10
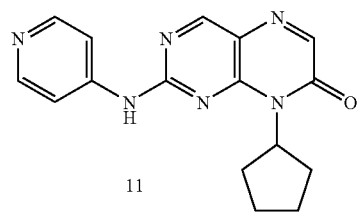
11

TABLE 1-continued
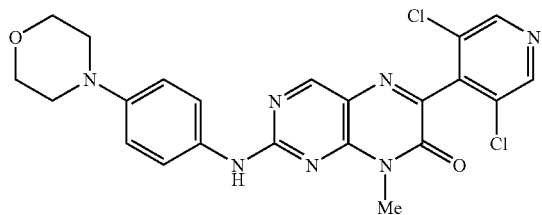
12
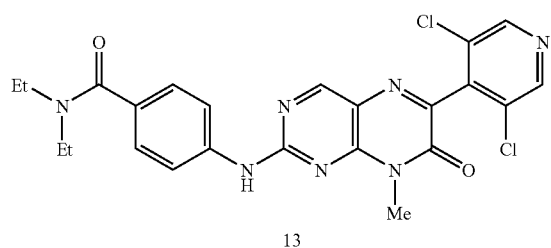
13
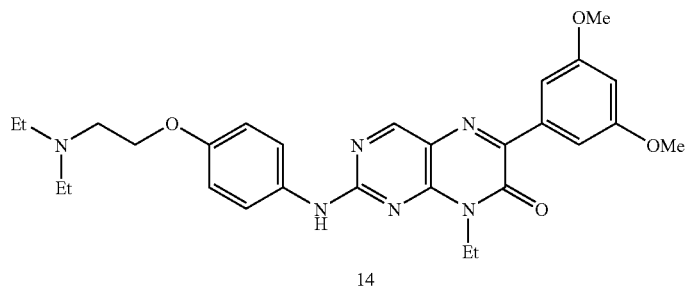
14
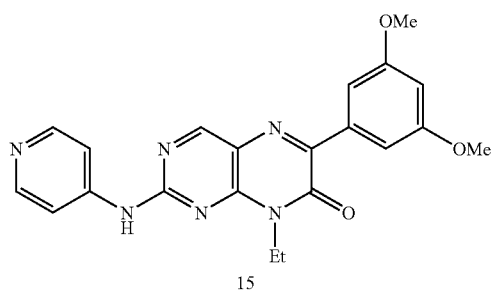
15
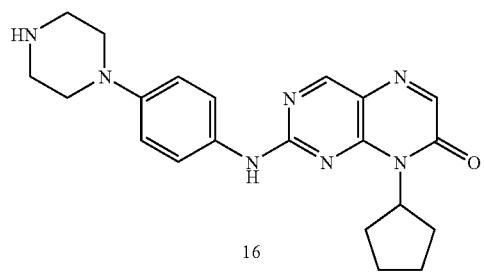
16

TABLE 1-continued
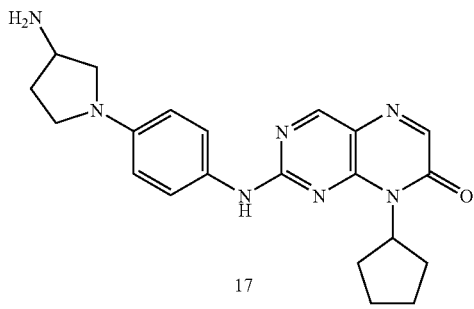
17
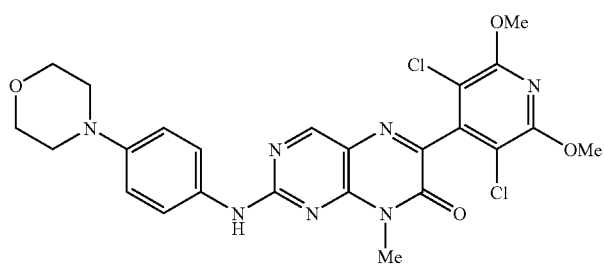
18
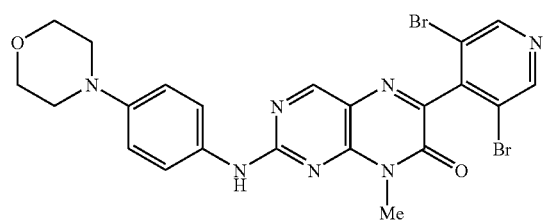
19
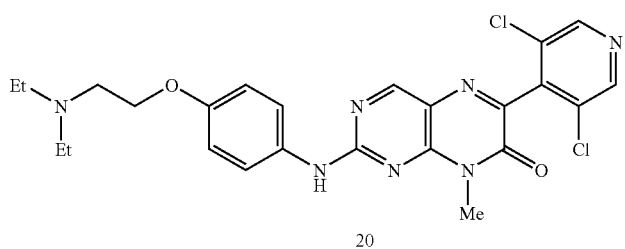
20
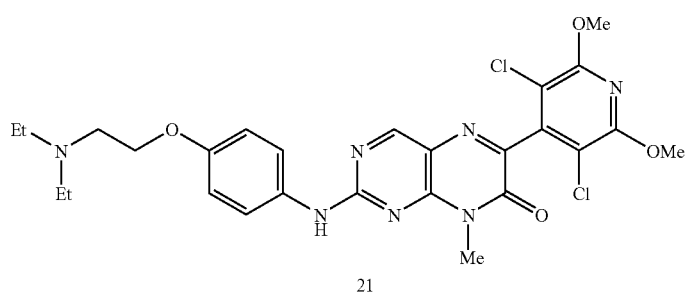
21

TABLE 1-continued
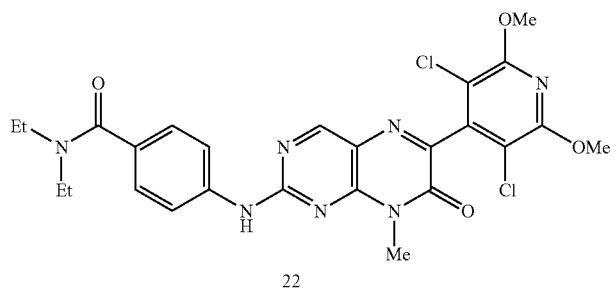
22
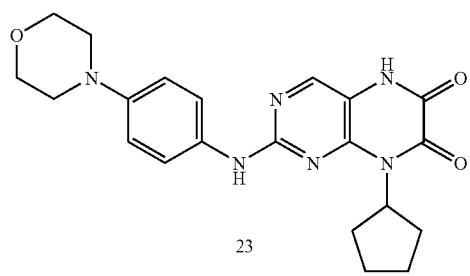
23
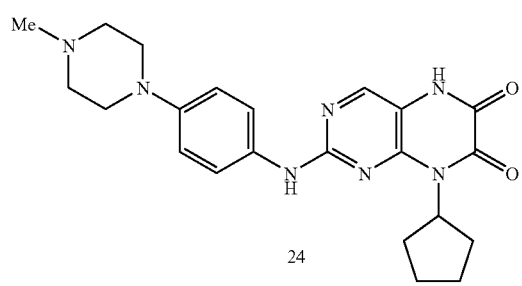
24
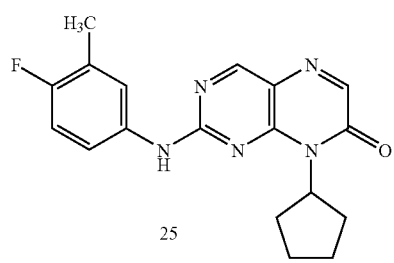
25
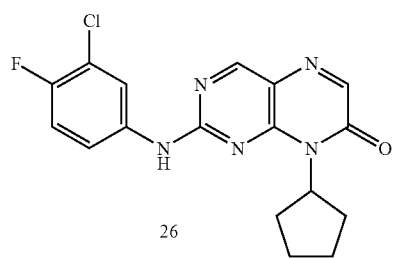
26

TABLE 1-continued
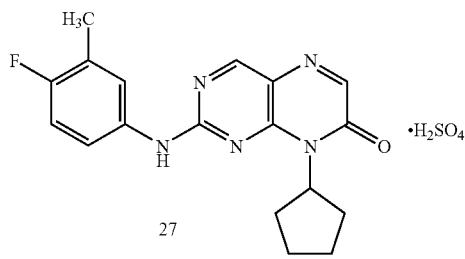
27
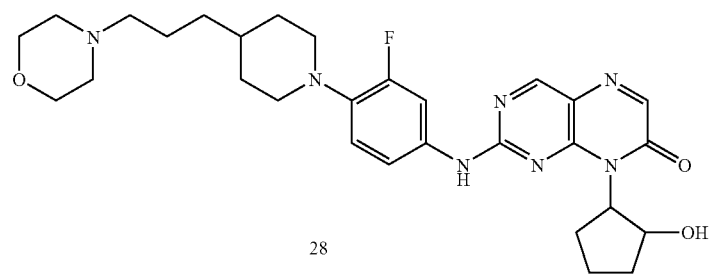
28
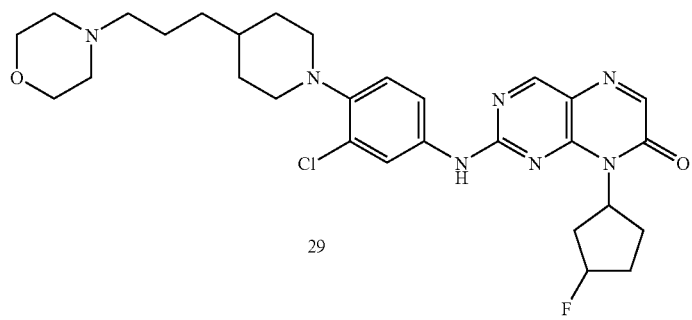
29
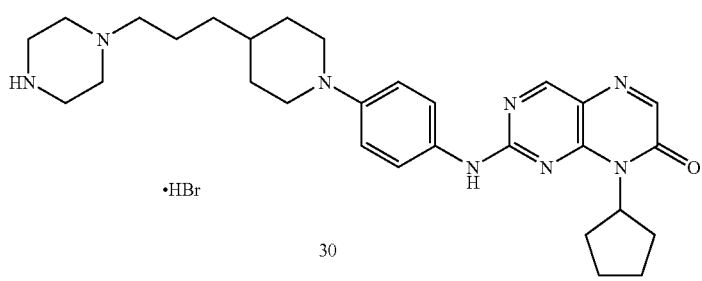
30
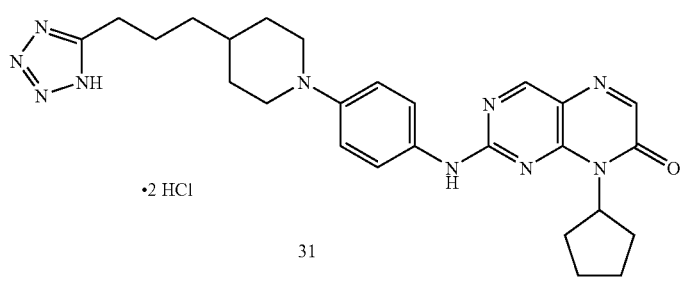
31

TABLE 1-continued
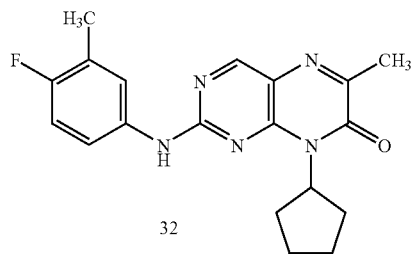
32
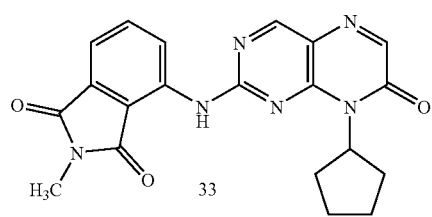
33
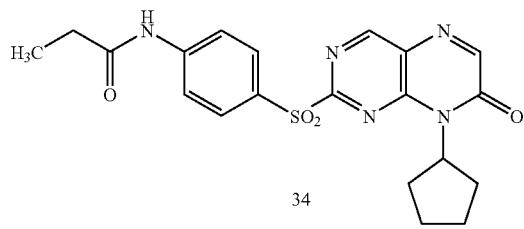
34
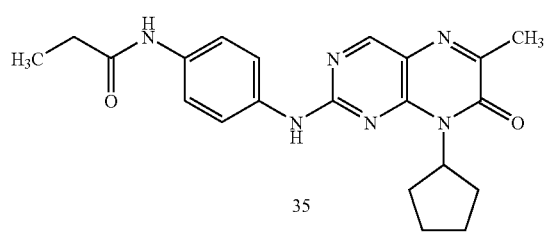
35
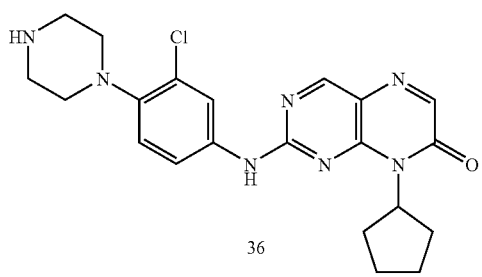
36
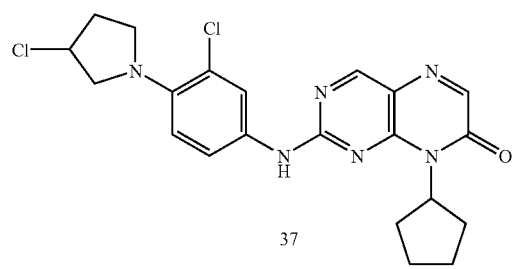
37

TABLE 1-continued
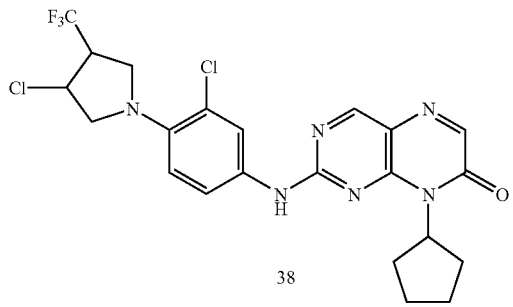
38
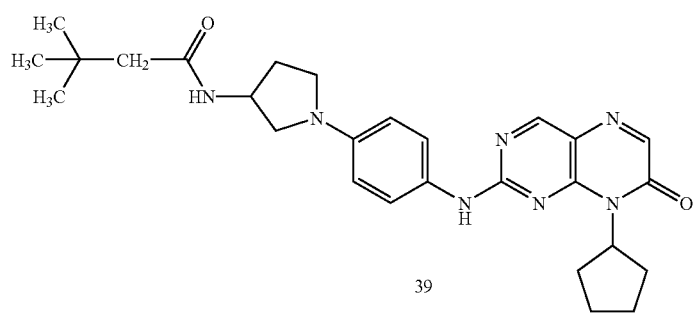
39
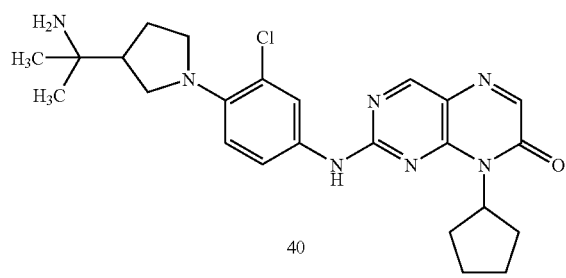
40
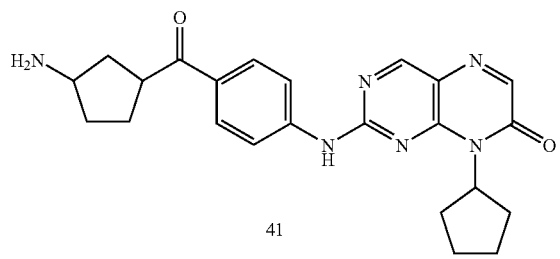
41
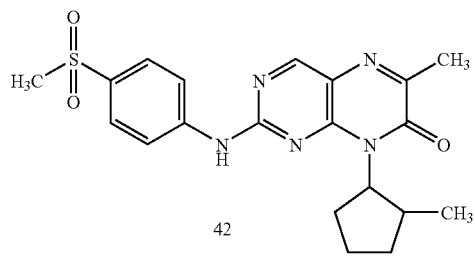
42

TABLE 1-continued
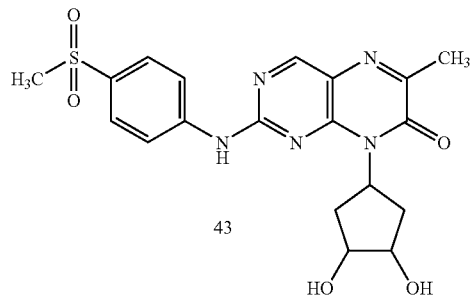
43
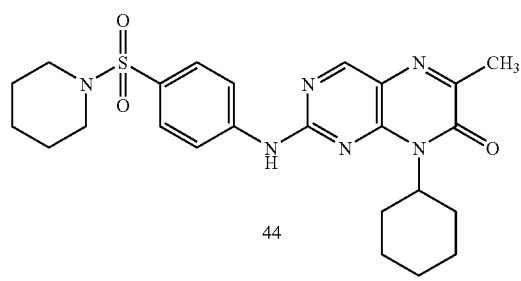
44
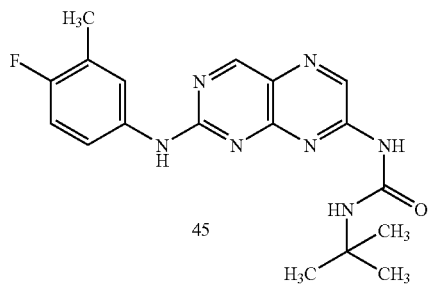
45
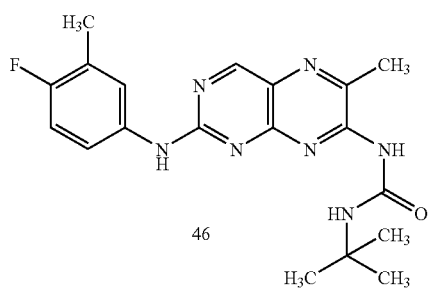
46
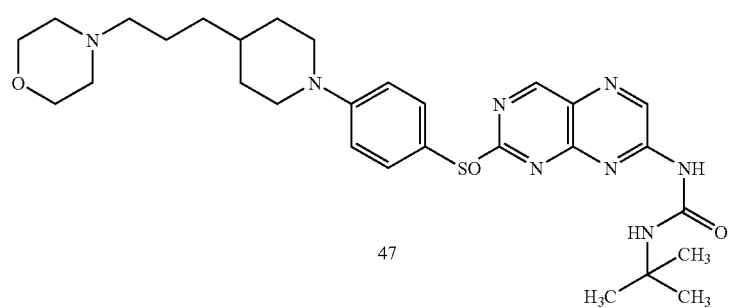
47

TABLE 1-continued

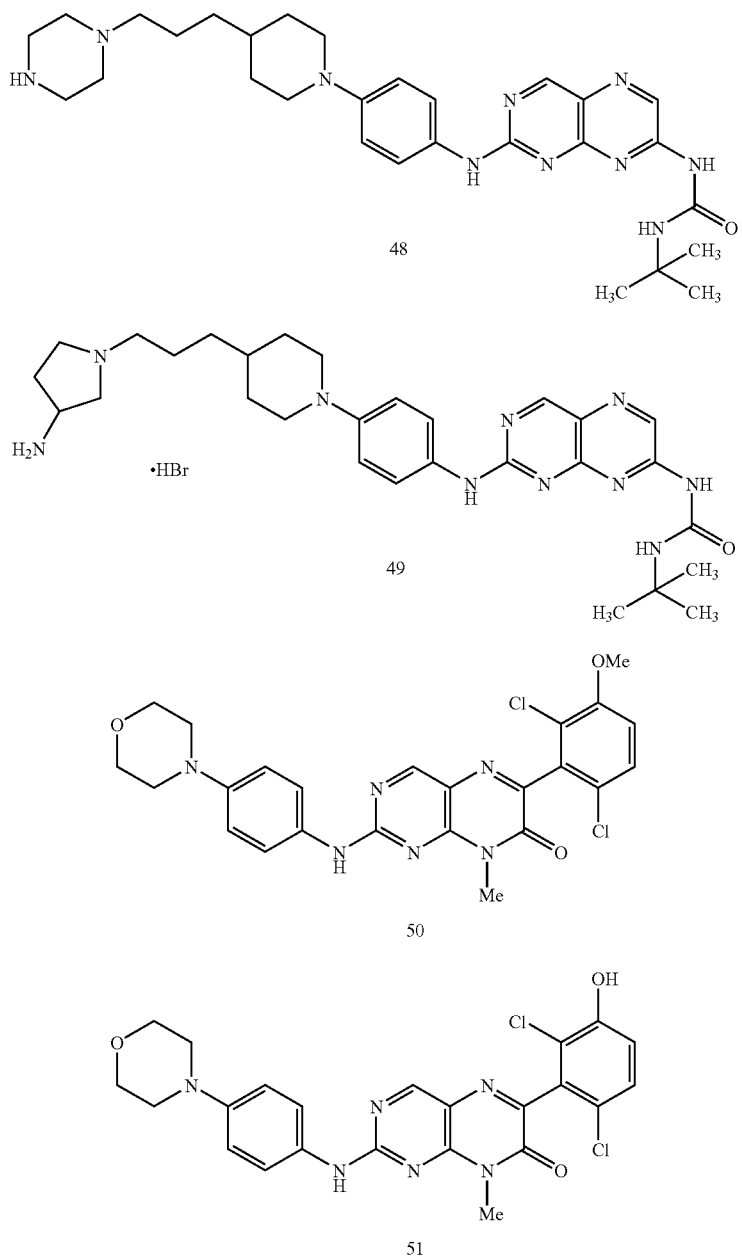

The pteridines provided by this invention are named according to the following numbering:

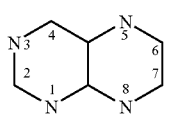

For example, compound 51 shown in Table 1 is named as 6-(2,6-dichloro-3-hydroxyphenyl)-8-methyl-2[[4-(morpholin-4-yl)phenyl]amino]-8H-pteridine-7-one. Additional preferred compounds include the following:

8-(3-Ethoxycyclopentyl)-5-methyl-2-(4-piperazin-1-yl-phenylamino)-5,8-dihydro-6H-pteridin-7-one;

2-[4-(4-Acetyl-piperazin-1-yl)-phenylamino]-8-cyclopentyl-5-methyl-5,8-dihydro-6H-pteridin-7-one;

N-{1-[4-(8-Cyclopentyl-5-methyl-7-oxo-5,6,7,8-tetrahydro-pteridin-2-ylamino)-phenyl]-pyrrolidin-3-yl}-3,3-dimethyl-butyramide;

8-Cyclopentyl-5-methyl-2-(4-morpholin-4-yl-phenylamino)-5,8-dihydro-6H-pteridin-7-one;

8-cyclopentyl-2-{4-[4-(2-hydroxy-ethyl)-piperazin-1-yl]-phenylamino}-5-methyl-5,8-dihydro-6H-pteridin-7-one;

8-cyclopentyl-2-{4-[4-(2-hydroxy-ethyl)-3,5-dimethyl-piperazin-1-yl]-phenylamino}-5-methyl-5,8-dihydro-6H-pteridin-7-one;

1-[4-(8-Isopropyl-5-methyl-7-oxo-5,6,7,8-tetrahydro-pteridin-2-ylamino)-phenyl]-pyrrolidine-3-carboxylic acid butylamide;

{4-[4-(8-Cyclopentyl-5-methyl-7-oxo-5,6,7,8-tetrahydro-pteridin-2-ylamino)-phenyl]-piperazin-1-yl}-acetic acid; and 6-(2,6-Dichloro-3-hydroxy-phenyl)-8-methyl-2-(4-morpholin-4-yl-phenylamino)-8H-pteridin-7-one.

Representative compounds of the present invention, which are encompassed by Formulas Ia, Ib, Ic, and Id, include, but are not limited to the compounds in Table 1 and their pharmaceutically acceptable acid or base addition salts, or amide or prodrugs thereof.

The compounds of the present invention can exist in unsolvated forms as well as solvated forms, including hydrated forms. In general, the solvated forms, including hydrated forms, are equivalent to unsolvated forms and are intended to be encompassed within the scope of the present invention.

The compounds of Formulas Ia, Ib, Ic, and Id are capable of further forming both pharmaceutically acceptable formulations comprising salts, including but not limited to acid addition and/or base salts, solvates and N-oxides of a compound of Formulas Ia, Ib, Ic, and Id. This invention also provides pharmaceutical formulations comprising a compound of Formulas Ia, Ib, Ic, and Id together with a pharmaceutically acceptable carrier, diluent, or excipient therefor. All of these forms are within the present invention.

Pharmaceutically acceptable acid addition salts of the compounds of Formulas Ia, Ib, Ic, and Id include salts derived form inorganic acids such as hydrochloric, nitric, phosphoric, sulfuric, hydrobromic, hydriodic, phosphorus, and the like, as well as the salts derived from organic acids, such as aliphatic mono- and dicarboxylic acids, phenyl-substituted alkanoic acids, hydroxy alkanoic acids, alkanedioic acids, aromatic acids, aliphatic, and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are the salts of amino acids such as arginate, gluconate, galacturonate, and the like; see, for example, Berge, et al., "Pharmaceutical Salts," *J. of Pharmaceutical Science*, 1977;66:1–19.

The acid addition salts of the basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metal hydroxides, or of organic amines. Examples of metals used as cations are sodium, potassium, magnesium, calcium, and the like. Examples of suitable amines are N,N'-dibenzylethylenediamine, chloroprocaine, choline, diethanolamine, ethylenediamine, N-methylglucamine, and procaine; see, for example, Berge, et al., supra.

The base addition salts of acidic compounds are prepared by contacting the free acid form with a sufficient amount of the desired base to produce the salt in the conventional manner. The free acid form may be regenerated by contacting the salt form with an acid and isolating the free acid in a conventional manner. The free acid forms differ from their respective salt forms somewhat in certain physical properties such as solubility in polar solvents, but otherwise the salts are equivalent to their respective free acid for purposes of the present invention.

The compounds of the present invention are useful for treating cancer (for example, leukemia and cancer of the lung, breast, prostate, and skin such as melanoma), and other proliferative diseases including but not limited to psoriasis, HSV, HIV, restenosis, and atherosclerosis. To utilize a compound of the present invention to treat cancer, a patient having cancer is administered a therapeutically effective amount of a pharmaceutically acceptable composition comprising an invention compound.

A further embodiment of this invention is a method of treating subjects suffering from diseases caused by vascular smooth muscle cell proliferation. Compounds within the scope of the present invention effectively inhibit vascular smooth muscle cell proliferation and migration. The method entails inhibiting vascular smooth muscle proliferation, and/or migration by administering an effective amount of a compound of Formulas Ia, Ib, Ic, and Id to a subject in need of treatment.

The compounds of the present invention can be formulated and administered in a wide variety of oral and parenteral dosage forms, including transdermal and rectal administration. It will be recognized to those skilled in the art that the following dosage forms may comprise as the active component, either a compound of Formulas Ia, Ib, Ic, and Id or a corresponding pharmaceutically acceptable salt or solvate of a compound of Formulas Ia, Ib, Ic, and Id.

A further embodiment of this invention is a pharmaceutical formulation comprising a compound of Formulas Ia, Ib, Ic. and Id together with a pharmaceutically acceptable carrier, diluent, or excipient therefor. For preparing pharmaceutical compositions with the compounds of the present invention, pharmaceutically acceptable carriers can be either a solid or liquid. Solid form preparations include powders, tablets, pills, capsules, cachets, suppositories, and dispensable granules. A solid carrier can be one or more substances which may also act as diluents, flavoring agents, binders, preservatives, tablet disintegrating agents, or an encapsulating material.

In powders, the carrier is a finely divided solid such as talc or starch which is in a mixture with the finely divided active component. In tablets, the active component is mixed with the carrier having the necessary binding properties in suitable proportions and compacted in the shape and size desired.

The formulations of this invention preferably contain from about 5% to about 70% or more of the active compound. Suitable carriers include magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. A preferred form for oral use are capsules, which include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogenously therein, as by stirring. The molten homogenous mixture is then poured into convenient size molds, allowed to cool, and thereby to solidify.

Liquid form preparations include solutions, suspensions, and emulsions such as water or water/propylene glycol solutions. For parenteral injection, liquid preparations can be formulated in solution in aqueous polyethylene glycol solution, isotonic saline, 5% aqueous glucose, and the like. Aqueous solutions suitable for oral use can be prepared by dissolving the active component in water and adding suitable colorants, flavors, stabilizing and thickening agents as desired. Aqueous suspensions suitable for oral use can be made by dispersing the finely divided active component in water and mixing with a viscous material, such as natural or synthetic gums, resins, methylcellulose, sodium carboxymethylcellulose, or other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like. Waxes, polymers, microparticles, and the like can be utilized to prepare sustained-release dosage forms. Also, osmotic pumps can be employed to deliver the active compound uniformly over a prolonged period.

The pharmaceutical preparations of the invention are preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampules. Also, the unit dosage form can be a capsule, tablet, cachet, or lozenge itself, or it can be the appropriate number of any of these in packaged form.

The therapeutically effective dose of a compound of Formulas Ia, Ib, Ic, and Id will generally be from about 1 mg to about 100 mg/kg of body weight per day. Typical adult doses will be about 50 mg to about 800 mg per day. The quantity of active component in a unit dose preparation may be varied or adjusted from about 0.1 mg to about 500 mg, preferably about 0.5 mg to 100 mg according to the particular application and the potency of the active component. The composition can, if desired, also contain other compatible therapeutic agents. A subject in need of treatment with a compound of Formulas Ia, Ib, Ic, and Id is administered a dosage of about 1 to about 500 mg per day, either singly or in multiple doses over a 24-hour period.

The compounds of the present invention are capable of binding to and inhibiting the activity of protein kinases, such as cdks, Wee 1, PDGFr, FGFr, c-src, and EGFr-FL. Cdks form complexes with cyclins, and these complexes phosphorylate key proteins that regulate the progression of cells through the cell cycle (Meijer L., *Progress in Cell Cycle Research*, 1995;1:351–363). The compounds of this invention inhibit this phosphorylation and therefore can be used as anti-proliferative agents for the treatment of cancer and/or restenosis and other proliferative diseases.

Because of their inhibitory activity against cdks and other kinases, the compounds of the present invention are also useful research tools for studying the mechanism of action of those kinases, both in vitro and in vivo.

The pteridines of this invention can be prepared by any of several standard synthetic processes commonly utilized by those skilled in the art of organic chemistry. An illustration of a typical preparation of compounds of the present invention is shown in Scheme I. Although these schemes often indicate exact structures, those with ordinary skill in the art will appreciate that the methods apply widely to analogous pteridines and intermediates therefor, given appropriate consideration to protection and deprotection of reactive functional groups by methods standard to the art of organic chemistry For example, hydroxy groups, in order to prevent unwanted side reactions, generally need to be converted to ethers or esters during chemical reactions at other sites in the molecules. The hydroxy protecting group is readily removed to provide the free hydroxy group. Amino groups and carboxylic acid groups are similarly derivatized to protect them against unwanted side reactions. Typical protecting groups and methods for attaching and cleaving them are described fully by Greene and Wuts in *Protective Groups in Organic Synthesis*, John Wiley and Sons, New York, ($2^{nd}$ Ed., 1991), and McOmie, *Protective Groups in Organic Chemistry*, Plenum Press, New York, 1973.

Scheme I

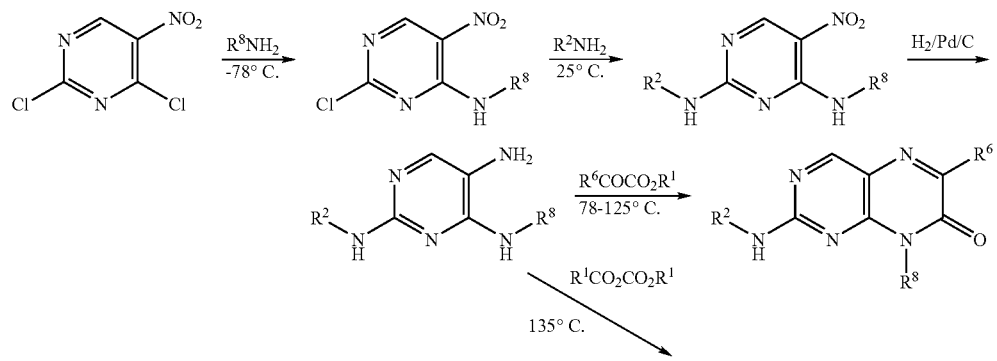

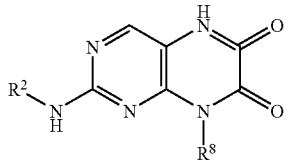

Those having skill in the art will recognize that the starting materials may be varied and additional steps employed to produce compounds encompassed by the present invention, as demonstrated by the following detailed examples.

As shown in Scheme I, 2,4-dichloro-5-nitropyrimidine is reacted with an appropriate amine at decreased temperatures to afford the corresponding 4-aminopyrimidine. The 2-chloro-5-nitro4-substituted aminopyrimidine is reacted with another amine ($R^2NH_2$) at ambient temperatures to produce a 5-nitro-2,4-diaminopyrimidine. The nitro group is subsequently reduced by hydrogenation to form a 2,4,5-triaminopyrimidine, which is then cyclized to the desired pteridine-7-one or -6,7-dione by reaction with the appropriate pyruvate or oxalate at elevated temperatures of about 50° C. to about 150° C. The term "$R^1$" in Scheme I is an oxalate or pyruvate ester forming group, typically a $C_1$–$C_6$ alkyl such as ethyl.

Alternatively, compounds of Formula IVd are made according to Scheme II. A 2,4,5-trihalopyrimidine is reacted sequentially with appropriately substituted amines to afford a 5,6-diaminopyrimidine. Cyclization to give a 2-halo pteridine is accomplished by reaction with bromoacetylchloride. Among the preferred compounds of the invention are those derived from reaction of the 2-halo pteridine with an appropriately substituted arylamine such as an aniline.

Scheme II

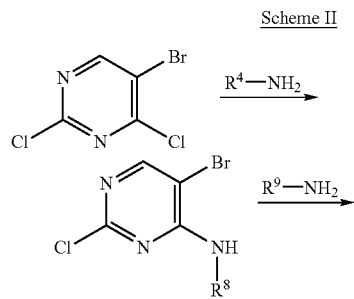

-continued

Compounds of the Formulas Ia–Ie wherein W is S, SO, or $SO_2$ are biologically active, as well as being particularly useful as intermediates leading to the compounds wherein W is NH. For example, Scheme III shows that a 2-alkylthio-4,5-dihalopyrimidine can be the starting material for animation as shown in Scheme II. Following normal cyclization to form the pteridine ring, the 2-alkylthio group can be oxidized, for example by reaction with meta-chloroperbenzoic acid, to provide a sulfoxide (n=1) or a sulfone (n=2). The sulfoxide or sulfone is readily displaced by reaction with an amine such as an arylamine (aryl $NH_2$). Typical compounds have the structures shown in Table 1 with the 2-arylamino group replaced by alkyl $S(O)_n$—.

Scheme III

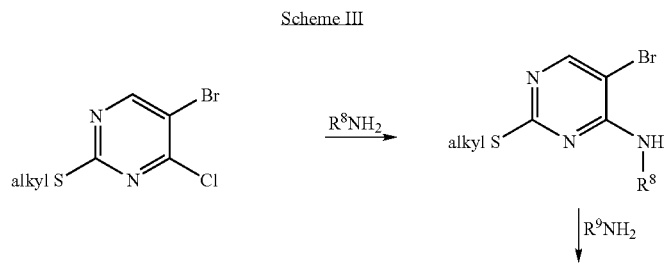

-continued

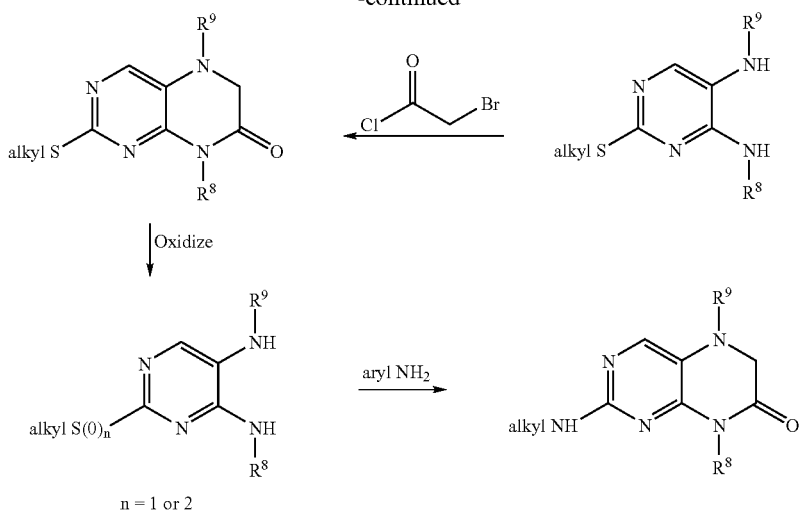

The pteridine ureas of Formula Ic can be conveniently prepared by acylating a 7-amino pteridine, which in turn is readily prepared using a 4,5-diaminopyrimidino. This is illustrated in Scheme IV below:

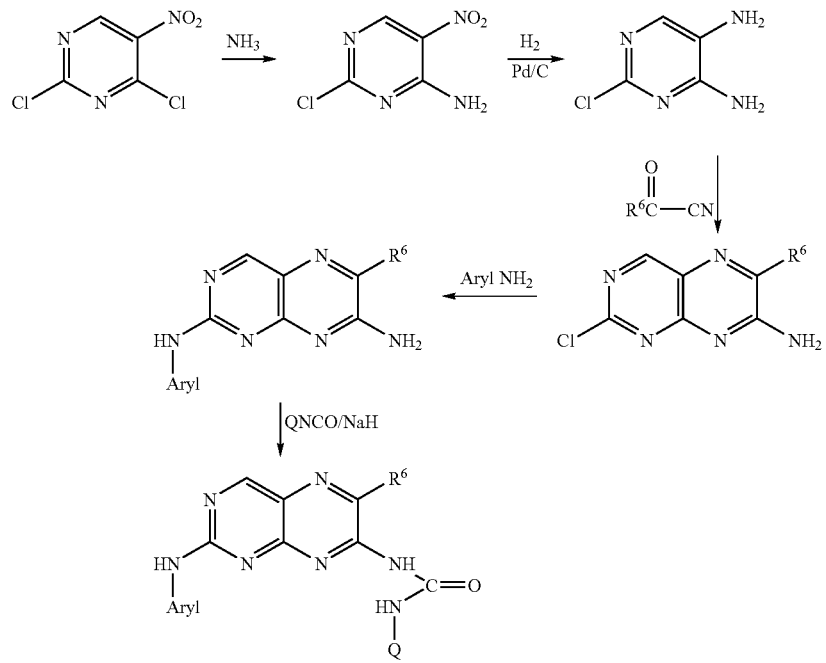

In the foregoing Scheme IV, 2,4-dichloro-5-nitropyrimidine is reacted with ammonia to afford the 4-amino-2-chloro-5-nitropyrimidine. Reduction of the nitro group, for instance by reaction with hydrogen in the presence of a catalyst such as palladium on carbon, provides the 2-chloro-4,5-diamino-pyrimidine, similar to that shown in Scheme III. Cyclization to a pteridine is accomplished by reaction of the 4,5-diaminopyrimidine with an agent such as a ketonitrile ($R^6$COCN) to afford the corresponding 2-chloro-7-aminopteridine. The 2-chloro group is readily displaced by reaction with an amine, for instance an arylamine, to give the corresponding 2-substitued-7-aminopteridine. This is an important intermediate in that it is readily acylated, for instance by reaction with an acyl halide, or preferably an isocyanate, to give the invention urea. The urea can be isolated and purified by standard processes such as chromatography, crystallization, and the like.

The disclosures in this application of all articles and references, including patents, are incorporated herein by reference.

The invention is illustrated further by the following detailed examples which are not to be construed as limiting the invention in scope or spirit to the specific procedures and compounds described therein The starting materials and various intermediates may be obtained from commercial sources, prepared from commercially available organic compounds, or prepared using well known synthetic methods. Each Example provides a general procedure for preparing several specific compounds, each of which is identified numerically as a subsection of each broad Example.

EXAMPLE 1

Synthesis of 2-Halo-4-(substituted-amino)-5-nitropyrimidines 1. 2-Chloro-4-(methylamino)-5-nitropyrimidine

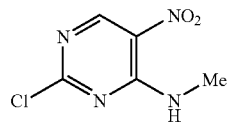

A solution of 5.82 g (30 mmol) of 2,4-dichloro-5-nitropyrimidine (N. Whittaker, *J. Chem. Soc.*, 1951;1565–1570) in 100 mL of tetrahydrofuran (THF) is cooled to −78° C. and a solution of 4.66 g (60 mmol) of 40% aqueous methylamine in 20 mL of 2-propanol is added dropwise over 5 minutes. After a further 10 minutes at −78° C., the mixture is allowed to warm to room temperature, and the solvent is removed under vacuum. The residue is then extracted into ethyl acetate (EtOAc), washed with water, and dried with sodium sulfate ($Na_2SO_4$). Removal of the solvent and chromatography on silica, eluting with hexane/EtOAc (92:8), gives 4.87 g (86%) of the title compound: mp (hexane) 86–87° C. (lit. mp: 90–91° C.; G. B. Barlin, *J. Chem. Soc. (B)*, 1967:954–958).

$^1$H NMR ($CDCl_3$): δ 9.05 (s, 1H, H-6), 8.40 (br, 1H, exchangeable with $D_2O$, NH), 3.23 (d, J=5.1 Hz, 3H, $CH_3$).

$^{13}$C NMR ($CDCl_3$): δ 164.25 (s, C-2), 156.89 (d, C-6), 156.10 (s, C-4), 126.80 (s, C-5), 28.28 (q, $CH_3$).

Further elution with solvent gives 0.48 g (8.5%) of 4-chloro-2-(methylamino)-5-nitropyrimidine mp (hexane) 167–169° C.; (lit. mp: 172–173° C.; G. B. Barlin, *J. Chem. Soc. (B)*, 1967:954–958).

$^1$H NMR [($CD_3$)$_2$SO] (2 conformers; ratio ca. 1:1): δ 9.12 and 9.03 (2 s, 1H, H-6), 8.97 (br, 1H, exchangeable with $D_2O$, NH), 2.92 and 2.90 (2 d, J=4.7 Hz, 3H, $CH_3$).

2. 2-Chloro-4-(cyclopentylamino)-5-nitropyrimidine

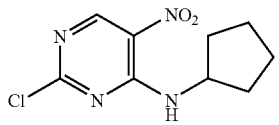

To a solution of 5.82 g (30 mmol) of 2,4-dichloro-5-nitropyrimidine (N. Whittaker, *J. Chem. Soc.*, 1951:1565–1570) in 100 mL THF at −78° C. is added dropwise over 5 minutes a solution of 5.11 g (60 mmol) of cyclopentylamine in 20 mL THF. After a further 10 minutes at −78° C., the mixture is allowed to warm to room temperature, and the solvent is removed under vacuum. The residue is then extracted into EtOAc, washed with water, and dried with $Na_2SO_4$. Removal of the solvent and chromatography on $SiO_2$, eluting with hexane/EtOAc (95:5) gives 6.20 g (85%) of the title compound: mp (hexane) 80–81.5° C.

$^1$H NMR ($CDCl_3$): δ 9.03 (s, 1H, H-6), 8.38 (br, 1H, exchangeable with $D_2O$, NH), 4.60 (sextet, J=7.0 Hz, 1H, cyclopentyl CH), 2.21–2.13 (m, 2H, cyclopentyl), 1.85–1.68 (m, 4H, cyclopentyl), 1.62–1.54 (m, 2H, cyclopentyl).

$^{13}$C NMR ($CDCl_3$): δ 164.15 (s, C-2), 157.08 (d, C-6), 154.96 (s, C-4), 126.43 (s, C-5), 53.23 (d, CH), 32.99 (t, $CH_2$), 23.69 (t, $CH_2$).

Analysis calculated for $C_9H_{11}ClN_4O_2$: C, 44.55; H, 4.57; N, 23.09. Found: C, 44.80; H, 4.54; N, 22.90.

Further elution with solvent gives 0.54 g (7.4%) of 4-chloro-2-(cyclopentylamino)-5-nitropyrimidine: mp (hexane) 149–153° C.

$^1$H NMR ($CDCl_3$) (2 conformers; ratio ca. 1:1): δ 9.07 and 8.96 (2 s, 1H, H-6), 6.11 and 5.97 (2 br, 1H, exchangeable with $D_2O$, NH), 4.38 (sextet, J=7.0 Hz, 1H, cyclopentyl CH), 2.17–2.05 (m, 2H, cyclopentyl), 1.81–1.64 (m, 4H, cyclopentyl), 1.56–1.47 (m, 2H, cyclopentyl).

$^{13}$C NMR ($CDCl_3$): δ 160.81 and 160.84 (2 s, C-4), 158.08 and 157.39 (2 d, C-6), 155.89 and 154.94 (2 s, C-2), 132.71 and 132.75 (2 s, C-5), 53.84 and 53.79 (2 d, CH), 32.96 and 32.91 (2 t, $CH_2$), 23.61 and 23.54 (2 t, $CH_2$).

HREIMS calculated for $C_9H_{11}ClN_4O_2$: 242.0571/244.0541. Found: 242.0574/244.0547.

3. 2-Chloro-4-(ethylamino)-5-nitropyrimidine

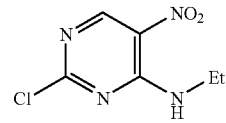

To a solution of 5.82 g (30 mmol) of 2,4-dichloro-5-nitropyrimidine (N. Whittaker, *J. Chem. Soc.*, 1951:1565–1570) in 100 mL THF at −78° C. is added dropwise over 5 minutes a solution of 3.87 g (60 mmol) of 70% aqueous ethylamine in 20 mL of 2-propanol. After being stirred at −78° C. for 15 minutes, the reaction mixture is allowed to warm to room temperature, and the solvent is removed under vacuum. The residue is worked up in EtOAc and chromatographed on silica, eluting with hexane/EtOAc (92:8), to give 4.90 g (81%) of the title compound: mp (hexane) 64–66° C.

$^1$H NMR ($CDCl_3$): δ 9.04 (s, 1H, H-6), 8.38 (br, 1H, exchangeable with $D_2O$, NH), 3.72 (qd, J=7.2, 5.3 Hz, 2H, $CH_2$), 1.35 (t, J=7.3 Hz, 3H, $CH_3$).

$^{13}$C NMR ($CDCl_3$): δ 164.24 (s, C-2), 157.05 (d, C-6), 155.40 (s, C-4), 126.50 (s, C-5), 36.58 (t, $CH_2$), 14.20 (q, $CH_3$).

Analysis calculated for $C_6H_7ClN_4O_2$: C, 35.57; H, 3.48; N, 27.65. Found: C, 35.52; H, 3.22; N, 27.57.

Further elution with hexane/EtOAc (9:1) gives 0.43 g (7%) of 4-chloro-2-(ethylamino)-5-nitropyrimidine: mp (i-$Pr_2O$) 122–123° C.

$^1$H NMR [($CD_3$)$_2$SO] (2 conformers; ratio ca. 1:1): δ 9.10 and 9.02 (2 s, 1H, H-6), 9.05 (m, 1H, exchangeable with $D_2O$, NH), 3.46–3.35 (m, 2H, $CH_2$), 1.16 and 1.15(2 t, J=7.2 Hz, 3H, $CH_3$).

$^{13}$C NMR [(CD$_3$)$_2$SO] (2 conformers; ratio ca. 1:1): δ 160.77 and 160.71 (2 s, C-4), 158.47 and 157.95 (2 d, C-6), 154.44 and 153.67 (2 s, C-2), 131.45 (s, C-5), 36.34 and 36.17 (2 t, CH$_2$), 13.94 and 13.86 (2 q, CH$_3$).

Analysis calculated for C$_6$H$_7$ClN$_4$O$_2$: C, 35.57; H, 3.48; N, 27.65. Found: C, 35.46; H 3.30; N, 27.43.

EXAMPLE 2

Synthesis of 2-(Substituted-amino)-4-(Substituted-amino)-5-nitropyrimidines 1. 4-(Methylamino)-2-[[4-(morpholin-4-yl)phenyl]amino]-5-nitropyrimidine

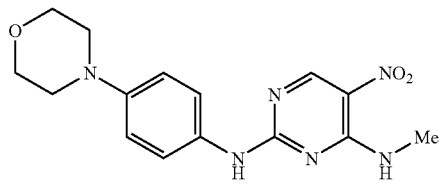

To a room temperature solution of 0.943 g (5 mmol) of 2-chloro-4-(methylamino)-5-nitropyrimidine in 25 mL THF is added a solution of 1.96 g (11 mmol) of 4-(4-aminophenyl)morpholine in 100 mL of 2-propanol, and the resulting mixture is heated and stirred at 50° C. for 30 minutes. The mixture is then diluted with water, the solid precipitate is collected, washed with water, and dried, to give 1.62 g (98%) of the title compound: mp (EtOH) 240–241° C.

$^1$H NMR [(CD$_3$)$_2$SO]: δ 10.24 (br, 1H, exchangeable with D$_2$O, $_2$NH), 8.93 (s, 1H, H-6), 8.87 (br, 1H, exchangeable with D$_2$O, $^4$NH), 7.71 (br d, J=8.1 Hz, 2H, H-2',6'), 6.94 (d, J=8.8 Hz, 2H, H-3',5'), 3.73 (br t, J=4.7 Hz, 4H, CH$_2$O), 3.07 (br t, J=4.7 Hz, 4H, CH$_2$N), 3.04 (d, J=4.7 Hz, 3H, CH$_3$N).

Analysis calculated for C$_{15}$H$_{18}$N$_6$O$_3$: C, 54.54; H, 5.49; N, 25.44. Found: C, 54.81; H, 5.63; N, 25.59.

2. 2-[[4-[2-(Diethylamino)ethoxy]phenyl]amino]-4-(methylamino)-5-nitropyrimidine

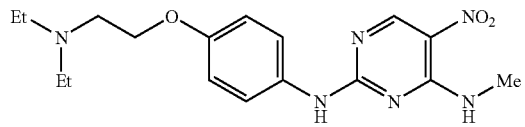

To a solution of 1.89 g (10 mmol) of 2-chloro-4-(methylamino)-5-nitropyrimidine in 100 mL THF at −78° C. is added a solution of 2.48 g (12 mmol) of 4-[2-(diethylamino)ethoxy]aniline in 100 mL of 2-propanol, and the resulting mixture is allowed to warm slowly to room temperature. The precipitate is collected, washed with 2-propanol, and dissolved in water. After being filtered through celite, the aqueous solution is basified with aqueous ammonia, and the resulting precipitate is collected, washed with water, and dried, to give 2.88 g (80%) of the title compound: mp (EtOH) 163–164° C.

$^1$H NMR [(CD$_3$)$_2$SO]: δ 10.27 (br, 1H, exchangeable with D$_2$O, $_2$NH), 8.94 (s, 1H, H-6), 8.87 (br, 1H, exchangeable with D$_2$O, $^4$NH), 7.73 (br d, J=6.9 Hz, 2H, H-2',6'), 6.92 (d, J=8.7 Hz, 2H, H-3',5'), 3.99 (t, J=6.1 Hz, 2H, CH$_2$O), 3.04 (d, J=4.0 Hz, 3H, CH$_3$N), 2.75 (t, J=6.2 Hz, 2H, CH$_2$N), 2.54 (q, J=7.1 Hz, 4H, CH$_2$N), 0.97 (t, J=7.1 Hz, 6H, CH$_3$).

Analysis calculated for C$_{17}$H$_{24}$N$_6$O$_3$: C, 56.65; H. 6.71; N, 23.32. Found: C, 56.77; H, 6.52; N, 23.57.

3. 2-[[4-(Diethylaminocarbonyl)phenyl]amino]-4-(methylamino)-5-nitropyrimidine

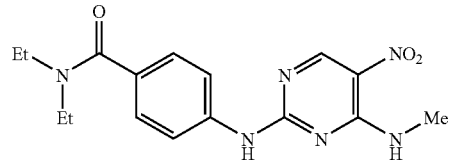

To a room temperature solution of 0.943 g (5 mmol) of 2-chloro-4-(methylamino)-5-nitropyrimidine in 25 mL THF is added a solution of 2.11 g (11 mmol) of 4-amino-N,N-diethylbenzamide in 100 mL of 2-propanol, and the resulting mixture is heated and stirred at reflux for 1 hour. The mixture is then diluted with water, the solid precipitate is collected, washed with water, and dried, to give 1.50 g (87%) of the title compound: mp (EtOH) 213–215° C.

$^1$H NMR [(CD$_3$)$_2$SO]: δ 10.49 (br, 1H, exchangeable with D$_2$O, $_2$NH), 8.99 (s, 1H, H-6), 8.90 (br, 1H, exchangeable with D$_2$O, $^4$NH), 7.88 (br d, J=7.6 Hz, 2H, H-2',6'), 7.34 (d, J=8.5 Hz, 2H, H-3',5'), 3.34 (m, 4H, CH$_2$), 3.07 (d, J=4.7 Hz, 3H, CH$_3$N), 1.10(br, 6H, CH$_3$).

Analysis calculated for C$_{16}$H$_{20}$N$_6$O$_3$: C, 55.80; H, 5.85; N, 24.40. Found: C, 55.85; H, 5.54; N, 24.50.

4. 4-(Cyclopentylamino)-2-[[4-(morpholin-4-yl)phenyl)]amino]-5-nitropyrimidine

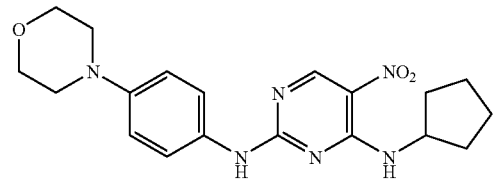

To a room temperature solution of 1.21 g (5 mmol) of 2-chloro-4-(cyclopentylamino)-5-nitropyrimidinein 50 mL THF is added a solution of 1.96 g (11 mmol) of 4-(4-aminophenyl)morpholine in 100 mL of 2-propanol, and the resulting mixture is heated under reflux for 30 minutes. The mixture is then diluted with water, the solid precipitate is collected, washed with water, and dried to give 1.77 g (100%) of the title compound: mp (MeOH) 211–213° C.

$^1$H NMR [(CD$_3$)$_2$SO]: δ 10.30 (br, 1H, exchangeable with D$_2$O, $^2$NH), 8.94 (s, 1H, H-6), 8.52 (br d, J=6.5 Hz, 1H, exchangeable with D$_2$O, $^4$NH), 7.69 (br d, J=8.4 Hz, 2H, H-2',6'), 6.94 (d, J=8.9 Hz, 2H, H-3',5'), 4.44 (m, 1H, cyclopentyl CH), 3.73 (br t, J=4.7 Hz, 4H, CH$_2$O), 3.07 (br t, J=4.7 Hz, 4H, CH$_2$N), 2.09–2.01 (m, 2H, cyclopentyl), 1.77–1.57 (m, 6H, cyclopentyl).

Analysis calculated for C$_{19}$H$_{24}$N$_6$O$_3$: C, 59.36; H, 6.29; N, 21.86. Found: C, 59.43; H, 6.12; N, 21.73.

5. 4-(Cyclopentylamino)-2-[[4-(4-methylpiperazin-1-yl)phenyl]amino]-5-nitropyrimidine

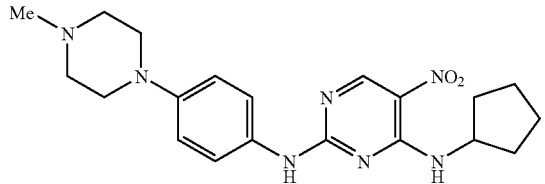

To a solution of 0.97 g (4 mmol) of 2-chloro-4-(cyclopentylamino)-5-nitropyrimidine in 50 mL THF at −78° C. is added a solution of 0.91 g (4.8 mmol) of 1-(4-aminophenyl)-4-methylpiperazine in 50 mL of 2-propanol, and the resulting mixture is allowed to warm slowly to room temperature. After acidification with acetic acid, the solvents were removed under vacuum, and the residue is dissolved in water. After being washed with EtOAc, the aqueous solution is basified with aqueous ammonia, and the product is extracted into EtOAc and dried, to give 1.15 g (77%) of the title compound: mp (MeOH) 204–206° C.

$^1$H NMR [$(CD_3)_2SO$]: δ 10.26 (br, 1H, exchangeable with $D_2O$, $^2$NH), 8.94 (s, 1H, H-6), 8.51 (br d, J=6.3 Hz, 1H, exchangeable with $D_2O$, $^4$NH), 7.67 (br d, J=8.2 Hz, 2H, H-2',6'), 6.92 (d, J=8.9 Hz, 2H, H-3',5'), 4.45 (m, 1H, cyclopentyl CH), 3.10 (br t, J=4.8 Hz, 4H, $CH_2N$), 2.44 (br t, J=4.9 Hz, 4H, $CH_2N$), 2.22 (s, 3H, $CH_3$), 2.09–2.00 (m, 2H, cyclopentyl), 1.78–1.56 (m, 6H, cyclopentyl).

Analysis calculated for $C_{20}H_{27}N_7O_2$: C, 60.44; H, 6.85; N, 24.67. Found: C, 60.36; H, 6.82; N, 24.58.

Evaporation of the solvent from the EtOAc wash gives a solid which is identified as 4-[(cyclopentyl)amino]-2-[[4-[4-[4-(cyclopentylamino)-5-nitropyrimidin-2-yl]piperazin-1-yl]phenyl]amino]-5-nitropyrimidine: mp (EtOAc) 244–246.5° C.

$^1$H NMR ($CDCl_3$): δ 9.01 and 9.00 (2 s, 2H, H-6,6''), 8.53 (br, 1H, exchangeable with $D_2O$, NH), 8.40 (br d, J=6.6 Hz, 1H, exchangeable with $D_2O$, NH), 7.89 (br, 1H, exchangeable with $D_2O$, $^2$NH), 7.57 (br, 2H, H-2',6'), 6.97 (d, J=9.0 Hz, 2H, H-3',5'), 4.54–4.42 (m, 2H, cyclopentyl CH), 4.18–4.06 (m, 4H, $CH_2N$), 3.25 (br, 4H, $CH_2N$), 2.15–2.07 (m, 4H, cyclopentyl), 1.85–1.54 (m, 12H, cyclopentyl).

Analysis calculated for $C_{28}H_{35}N_{11}O_4$: C, 57.03; H, 5.98; N, 26.13. Found: C, 56.57; H. 5.88; N, 25.76.

6. 4-(Cyclopentylamino)-2-[(pyridin-4-yl)amino]-5-nitropyrimidine

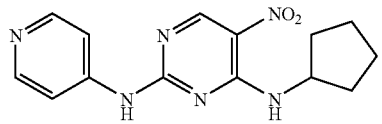

A mixture of 0.64 g (3 mmol) of 2-chloro-4-(cyclopentylamino)-5-nitropyrimidine and 0.62 g (6.6 mmol) of 4-aminopyridine in 5 mL of DMSO is stirred at room temperature for 15 minutes. The solution is diluted with water and basified with aqueous ammonia to give 0.41 g (44%) of the title compound: mp (EtOH) 219–221° C.

$^1$H NMR [$(CD_3)_2SO$]: δ 10.66 (br, 1H, exchangeable with $D_2O$, $^2$NH), 9.04 (s, 1H, H-6), 8.53 (br d, J=6.9 Hz, 1H, exchangeable with $D_2O$, $^4$NH), 8.45 (d, J=6.0 Hz, 2H, H-2',6'), 7.79 (br d, J=6.3 Hz, 2H, H-3',5'), 4.53 (sextet, J=6.4 Hz, 1H, cyclopentyl CH), 2.13–2.02 (m, 2H, cyclopentyl), 1.80–1.60 (m, 6H, cyclopentyl).

Analysis calculated for $C_{14}H_{16}N_6O_2$: C, 55.99; H, 5.37; N, 27.98. Found: C, 55.95; H, 5.56; N, 27.89.

7. 2-[[4-[2-(Diethylamino)ethoxy]phenyl]amino]-4-(ethylamino)-5-nitropyrimidine

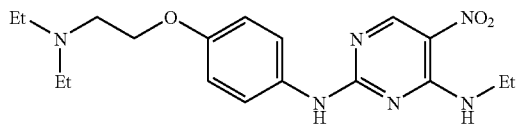

To a solution of 1.013 g (5 mmol) of 2-chloro-4-(ethylamino)-5-nitropyrimidine in 50 mL THF at −78° C. is added a solution of 2.48 g (12 mmol) of 4-[2-(diethylamino)ethoxy]aniline in 50 mL of 2-propanol, and the resulting mixture is allowed to warm slowly to room temperature. After removal of the solvent, the residue is dissolved in aqueous acetic acid and filtered through celite. The aqueous solution is then basified with aqueous ammonia, and the resulting precipitate is collected, washed with water, and dried to give 1.65 g (95%) of the title compound: mp (MeOH) 134–136° C.

$^1$H NMR [$(CD_3)_2SO$]: δ 10.24 (br, 1H, exchangeable with $D_2O$, $^2$NH), 8.95 (s, 1H, H-6), 8.88 (br, 1H, exchangeable with $D_2O$, $^4$NH), 7.17 (br d, J=7.2 Hz, 2H, H-2',6'), 6.92 (d, J=8.9 Hz, 2H, H-3',5'), 3.99 (t, J=6.2 Hz, 2H, $CH_2O$), 3.57 (br q, J=7.1 Hz, 2H, $CH_2N$), 2.75 (t, J=6.2 Hz, 2H, $CH_2N$), 2.54 (q, J=7.1 Hz, 4H, $CH_2N$), 1.21 (t, J=7.1 Hz, 3H, $CH_3$), 0.97 (t, J=7.1 Hz, 6H, $CH_3$).

Analysis calculated for $C_{18}H_{26}N_6O_3$: C, 57.74; H, 7.00; N, 22.44. Found: C, 57.87; H, 7.24; N, 22.52.

8. 4-(Ethylamino)-2-[(pyridin-4-yl)amino]-5-nitropyrimidine

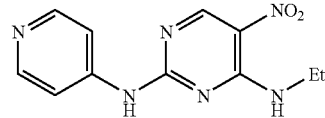

To a solution of 1.013 g (5 mmol) of 2-chloro-4-(ethylamino)-5-nitropyrimidine in 25 mL of DMSO at room temperature is added 1.04 g (11 mmol) of 4-aminopyridine, and the resulting solution is stirred at room temperature overnight. Dilution with water and neutralization with aqueous $K_2CO_3$ then gives 0.72 g (55%) of the title compound: mp (MeOH) 235–236° C.

$^1$H NMR [$(CD_3)_2SO$]: δ 10.60 (br, 1H, exchangeable with $D_2O$, $^2$NH), 9.03 (s, 1H, H-6), 8.96 (br, 1H, exchangeable with $D_2O$, $^4$NH), 8.44 (dd, J=5.0, 1.5 Hz, 2H, H-2',6'), 7.78 (dd, J=5.0, 1.5 Hz, 2H, H-3',5'), 3.64 (br q, J=7.1 Hz, 2H, $CH_2N$), 1.26 (t, J=7.1 Hz, 3H, $CH_3$).

Analysis calculated for $C_{11}H_{12}N_6O_2$: C, 50.77; H, 4.65; N, 32.29. Found: C, 50.59; H, 4.61; N, 32.27.

9. 2-[[4-[4-(tert-Butoxycarbonyl)piperazin-1-yl]phenyl]amino]-4-(cyclopentylamino)-5-nitropyrimidine

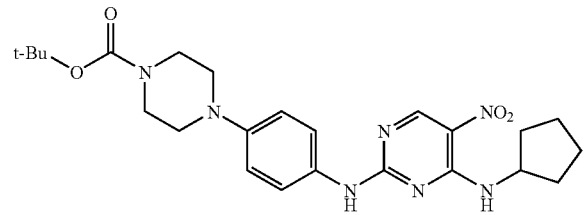

To a solution of 0.73 g (3 mmol) of 2-chloro-4-(cyclopentylamino)-5-nitropyrimidine and 0.49 g (4 mmol) N,N-dimethylaniline in 10 mL THF is added a solution of 0.94 g (3.4 mmol) of 1-(tert-butoxycarbonyl)-4-(4-aminophenyl)-piperazine in 20 mL of 2-propanol, and the resulting mixture is heated under reflux for 2 hours. After cooling and acidification with acetic acid, the mixture is diluted with water to give 1.37 g (94%) of the title compound: mp (MeOH) 194–196° C.

$^1$H NMR [(CD$_3$)$_2$SO]: δ 10.28 (br, 1H, exchangeable with D$_2$O, $^2$NH), 8.94 (s, 1H, H-6), 8.51 (br d, J=6.4 Hz, 1H, exchangeable with D$_2$O, $^4$NH), 7.69 (br d, J=7.9 Hz, 2H, H-2',6'), 6.95 (d, J=8.9 Hz, 2H, H-3',5'), 4.44 (m, 1H, cyclopentyl CH), 3.45 (br t, J=5.0 Hz, 4H, CH$_2$N), 3.06 (br t, J=5.0 Hz, 4H, CH$_2$N), 2.10–1.98 (m, 2H, cyclopentyl), 1.78–1.57 (m, 6H, cyclopentyl), 1.42 (s, 9H, CH$_3$).

Analysis calculated for C$_{24}$H$_{33}$N$_7$O$_4$: C, 59.61; H, 6.88; N, 20.28. Found: C, 59.63; H, 7.17; N, 20.42.

10. 2-[[4-[3-(tert-Butoxycarbonylamino)pyrrolidin-1-yl]phenyl]amino]-4-(cyclopentylamino)-5-nitropyrimidine

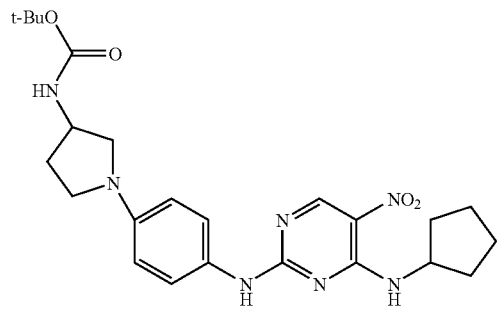

To a solution of 0.41 g (1.69 mmol) of 2-chloro-4-(cyclopentylamino)-5-nitropyrimidine and 0.25 g (2 mmol) N,N-dimethylaniline in 10 mL THF is added a solution of 0.47 g (1.69 mmol) of 3-(tert-butoxycarbonylamino)-1-(4-aminophenyl)pyrrolidine in 10 mL of 2-propanol, and the resulting mixture is heated under reflux for 2 hours. After cooling and acidification with acetic acid, the mixture is diluted with water to give 0.82 g (100%) of the title compound: mp (MeOH) 186–189° C.

$^1$H NMR [(CD$_3$)$_2$SO]: δ 10.19 (br, 1H, exchangeable with D$_2$O, $^2$NH), 8.91 (s, 1H, H-6), 8.50 (br d, J=6.8 Hz, 1H, exchangeable with D$_2$O, $^4$NH), 7.61 (br d, J=8.8 Hz, 2H, H-2',6'), 7.17 (br d, J=6.5 Hz, 1H, exchangeable with D$_2$O, $^3$'''NH), 6.50 (d, J=8.9 Hz, 2H, H-3',5'), 4.43 (m, 1H, cyclopentyl CHN), 4.13 (m, 1H, pyrrolidinyl CHN), 3.45 (m, 1H, pyrrolidinyl CHN), 3.34 (m, 1H, pyrrolidinyl CHN), 3.22 (m, 1H, pyrrolidinyl CHN), 3.02 (m, 1H pyrrolidinyl CHN), 2.14 (m, 1H, pyrrolidinyl), 2.09–1.99 (m, 2H, cyclopentyl), 1.88 (m, 1H, pyrrolidinyl), 1.77–1.56 (m, 6H, cyclopentyl), 1.40 (s, 9H, CH$_3$).

Analysis calculated for C$_{24}$H$_{33}$N$_7$O$_4$: C, 59.61; H, 6.88; N, 20.28. Found: C, 59.90; H, 6.80; N, 20.02.

EXAMPLE 3

Synthesis of 2-(Substituted-amino)-4-(substituted-amino-5-aminopyrimidines 1. 5-Amino-4-(methylamino)-2-[[4-(morpholin-4-yl)phenyl]amino]-pyrimidine

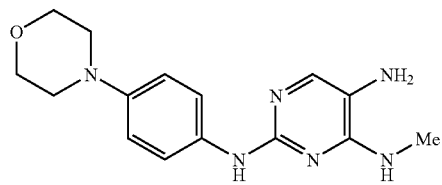

Hydrogenation of 4-(methylamino)-2-[(4-morpholinophenyl)amino]-5-nitropyrimidine (from Example 2(1) above) over palladium on charcoal (Pd/C) gave the title compound as a solid.

$^1$H NMR [(CD$_3$)$_2$SO]: δ 8.22 (br, 1H, exchangeable with D$_2$O, $^2$NH), 7.61 (d, J=8.9 Hz, 2H, H-2',6'), 7.33 (s, 1H, H-6), 6.80 (d, J=9.0 Hz, 2H, H-3',5'), 6.37 (q, J=4.6 Hz, 1H, exchangeable with D$_2$O, $^4$NH), 3.92 (br, 2H, exchangeable with D$_2$O, NH$_2$), 3.72 (br t, J=4.7 Hz, 4H, CH$_2$O), 2.97 (br t, J=4.7 Hz, 4H, CH$_2$N), 2.89 (d, J=4.5 Hz, 3H, CH$_3$).

2. 5Amino-2-[[4-[2-(diethylamino)ethoxy]phenyl]amino]-4-(methylamino)pyrimidine

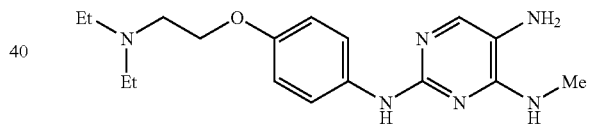

Hydrogenation of 2-[[4-[2-(diethylamino)ethoxy]phenyl]amino]-4-(methylamino)-5-nitropyrimidine (from Example 2(2) above) over Pd/C gave the title compound as an oil.

$^1$H NMR [(CD$_3$)$_2$SO]: δ 8.26 (br, 1H, exchangeable with D$_2$O, $^2$NH), 7.62 (d, J=9.0 Hz, 2H, H-2',6'), 7.33 (s, 1H, H-6), 6.76 (d, J=9.0 Hz, 2H, H-3',5'), 6.38 (q, J=4.6 Hz, 1H, exchangeable with D$_2$O, $^4$NH), 3.94–3.90 (m, 4H, CH$_2$O and NH$_2$), 2.89 (d, J=4.5 Hz, 3H, CH$_3$N), 2.73 (t, J=6.2 Hz, 2H, CH$_2$N), 2.53 (q, J=7.1 Hz, 4H, CH$_2$N), 0.97 (t, J=7.1 Hz, 6H, CH$_3$).

3. 5-Amino-2-[[4-(diethylaminocarbonyl)phenyl]amino]-4-(methylamino)pyrimidine

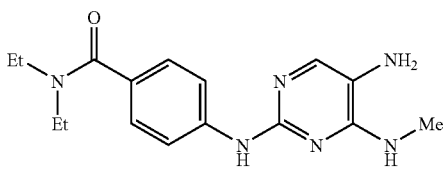

Hydrogenation of 2-[[4-(diethylaminocarbonyl)phenyl]amino]-4-(methylamino)-5-nitropyrimidine (from Example 2(3) above) over Pd/C gave the title compound as a solid.

¹H NMR [(CD₃)₂SO]: δ 8.76 (br, 1H, exchangeable with D₂O, ²NH, 7.78 (d, J=8.5 Hz, 2H, H-2',6'), 7.39 (s, 1H, H-6), 7.19 (d, J=8.6 Hz, 2H, H-3',5'), 6.48 (q, J=4.6 Hz, 1H, exchangeable with D₂O, ⁴NH), 4.08 (br, 2H, exchangeable with D₂O, NH₂), 3.34 (m, 4H, CH₂), 2.92 (d, J 4.5 Hz, 3H, CH₃N), 1.10 (t, J=7.0 Hz, 6H, CH₃).

4. 5-Amino-4-(cyclopentylamino)-2-[[4-(morpholin-4-yl)phenyl]amino]pyrimidine

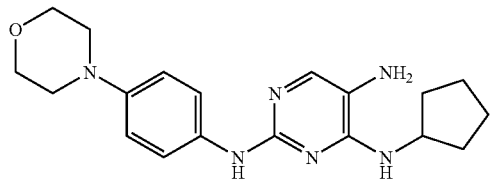

Hydrogenation of 4-(cyclopentylamino)-2-[[4-(morpholin-4-yl)phenyl)]amino]-5-nitropyrimidine (from example 2(4) above) over Pd/C gave the title compound as a solid.

¹H NMR [(CD₃)₂SO: δ 8.18 (br, 1H, exchangeable with D₂O, ²NH), 7.59 (d, J=9.0 Hz, 2H, H-2',6'), 7.33 (s, 1H, H-6), 6.79 (d, J=9.0 Hz, 2H, H-3',5'), 6.09 (d, J=6.7 Hz, 1H, exchangeable with D₂O, ⁴NH), 4.33 (sextet, J=6.7 Hz, 1H, cyclopentyl CH), 4.30 and 4.03 (2 br, 2H, exchangeable with D₂O, NH₂), 3.72 (br t, J=4.7 Hz, 4H, CH₂O), 2.97 (br t, J=4.7 Hz, 4H, CH₂N), 2.04–1.95 (m, 2H, cyclopentyl), 1.76–1.65 (m, 2H, cyclopentyl), 1.62–1.45 (m, 4H, cyclopentyl).

5. 5-Amino-4-(cyclopentylamino)-2-[[4-(4methylpiperazin-1-yl)phenyl]amino]pyrimidine

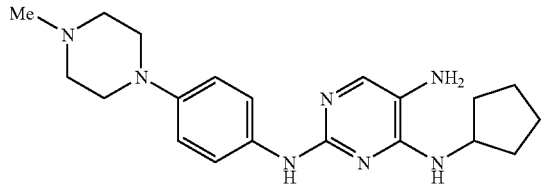

Hydrogenation of 4-(cyclopentylamino)-2-[[4-(4-methylpiperazin-1-yl)phenyl]amino]-5-nitropyrimidine (from Example 2(5) above) over Pd/C gave the title compound: mp (i-Pr₂O/CH₂Cl₂) 212° C. (dec).

¹H NMR [(CD₃)₂SO]: δ 8.14 (br, 1H, exchangeable with D₂O, ²NH), 7.57 (d, J=9.0 Hz, 2H, H-2',6'), 7.32 (s, 1H, H-6), 6.78 (d, J=9.0 Hz, 2H, H-3',5'), 6.08 (d, J=6.7 Hz, 1H, exchangeable with D₂O, ⁴NH), 4.32 (sextet, J=6.7 Hz, 1H, cyclopentyl CH), 4.01 (br, 2H, exchangeable with D₂O, NH₂), 2.99 (br t, J=4.7 Hz, 4H, CH₂N), 2.43 (br t, J=4.7 Hz, 4H, CH₂N), 2.21 (s, 3H, CH₃), 2.05–1.95 (m, 2H, cyclopentyl), 1.76–1.45 (m, 6H, cyclopentyl).

Analysis calculated for $C_{20}H_{29}N_7 \cdot 0.5H_2O$: C, 63.89; H, 7.91; N, 26.08. Found: C, 64.24; H, 7.90; N, 25.71.

6. 5-Amino-4-(cyclopentylamino)-2-[(pyridin-4-yl)amino]pyrimidine

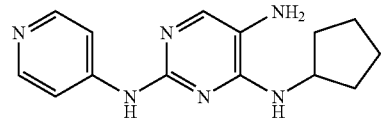

Hydrogenation of 4-(cyclopentylamino)-2-[(pyridin4-yl)amino]-5-nitropyrimidine (from Example 2(6) above) over Pd/C gave the title compound as a solid.

¹H NMR [(CD₃)₂SO]: δ 9.05 (br, 1H, exchangeable with D₂O, ²NH), 8.18 (d, J=6.2 Hz, 2H, H-2',6'), 7.67 (d, J=6.2 Hz, 2H, H-3',5'), 7.40 (s, 1H, H-6), 6.30 (d, J=6.6 Hz, 1H, exchangeable with D₂O, ⁴NH), 4.39–4.30 (m, 3H, cyclopentyl CH and NH₂), 2.13–1.98 (m, 2H, cyclopentyl), 1.78–1.66 (m, 2H, cyclopentyl), 1.64–1.47 (m, 4H, cyclopentyl).

7. 5-Amino-2-[[4-[2-(diethylamino)ethoxy]phenyl]amino]-4-(ethylamino)pyrimidine

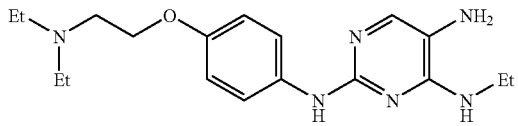

Hydrogenation of 2-[[4-[2-(diethylamino)ethoxy]phenyl]amino]-4-(ethylamino)-5-nitropyrimidine (from Example 2(7) above) over Pd/C gave the title compound as an oil.

¹H NMR [(CD₃)₂SO]: δ 8.21 (br, 1H, exchangeable with D₂O, ²NH), 7.60 (dd, J=8.9, 1.3 Hz, 2H, H-2',6'), 7.35 (s, 1H, H-6), 6.76 (d, J=9.1 Hz, 2H, H-3',5'), 6.28 (br t, J=5.1 Hz, 1H, exchangeable with D₂O, ⁴NH), 3.96 (m, 2H, exchangeable with D₂O, NH₂), 3.93 (t, J=6.2 Hz, 2H, CH₂O), 3.40 (br q, J=7.2 Hz, 2H, CH₂N), 2.73 (t, J=6.2 Hz, 2H, CH₂N), 2.53 (q, J=7.1 Hz, 4H, CH₂N), 1.19(t, J=7.2 Hz, 3H, CH₃), 0.97(t, J=7.1 Hz, 6H, CH₃).

8. 5-Amino-4-(ethylamino)-2-[(pyridin-4-yl)amino]pyrimidine

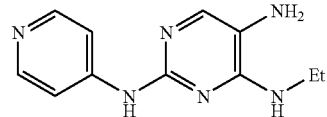

Hydrogenation of 4-(ethylamino)-2-[(pyridin4-yl)amino]-5-nitropyrimidine (from Example 2(8) above) over Pd/C gave the title compound as a solid.

¹HNMR [(CD₃)₂SO]: δ 9.05 (br, 1H, exchangeable with D₂O, ²NH), 8.19 (d, J=6.3 Hz, 2H, H-2',6'), 7.67 (d, J=6.4 Hz, 2H, H-3',5'), 7.41 (s, 1H, H-6), 6.49 (br t, J=5.0 Hz, 1H, exchangeable with D₂O, ⁴NH), 3.44 (qd, J=7.1, 5.3 Hz, 2H, CH₂N), 1.21 (t, J=7.2 Hz, 3H, CH₃).

9. 5-Amino-2-[[4-[4-(tert-butoxycarbonyl)piperazin-1-yl]phenyl]amino]-4-(cyclopentylamino)pyrimidine

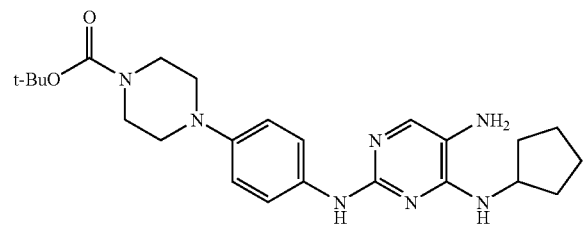

Hydrogenation of 2-[[4-[4-(tert-butoxycarbonyl)piperazin-1-yl]phenyl]-amino]-4-(cyclopentylamino)-5-nitropyrimidine (from Example 2(9) above) over Pd/C gave the title compound as a solid.

$^1$H NMR [(CD$_3$)$_2$SO]: δ 8.18 (br, 1H, exchangeable with D$_2$O, $^2$NH), 7.60 (d, J=9.0 Hz, 2H, H-2',6'), 7.33 (s, 1H, H-6), 6.81 (d, J=9.0 Hz, 2H, H-3',5'), 6.09 (d, J=6.7 Hz, 1H, exchangeable with D$_2$O, $^4$NH), 4.32 (sextet, J=6.6 Hz, 1H, cyclopentyl CH), 4.30 and 4.03 (2 br, 2H, exchangeable with D$_2$O, NH$_2$), 3.44 (br t, J=4.8 Hz, 4H, CH$_2$N), 2.94 (br t, J=5.0 Hz, 4H, CH$_2$N), 2.05–1.95 (m, 2H, cyclopentyl), 1.77–1.65 (m, 2H, cyclopentyl), 1.63–1.45 (m, 4H, cyclopentyl), 1.42 (s, 9H, CH$_3$).

10. 5-Amino-2-[[4-[3-(tert-butoxycarbonylamino)pyrrolidin-1-yl]phenyl]amino]-4-(cyclopentylamino)pyrimidine

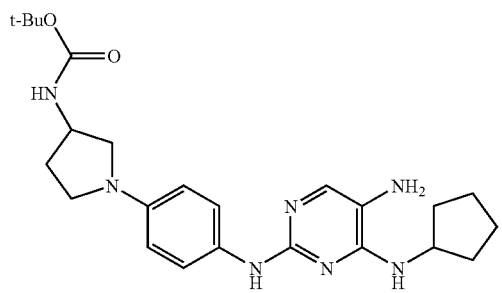

Hydrogenation of 2-[[4-[3-(tert-butoxycarbonylamino)pyrrolidin-1-yl]phenyl]amino]-4-(cyclopentylamino)-5-nitropyrimidine (from Example 2(10) above) over Pd/C gave the title compound as a solid.

$^1$H NM [(CD$_3$)$_2$SO]: δ 7.95 (br, 1H, exchangeable with D$_2$O, $^2$NH), 7.51 (d, J=9.0 Hz, 2H, H-2',6'), 7.31 (s, 1H, H-6), 7.13 (br d, J=6.7 Hz, 1H, exchangeable with D$_2$O, $^{3'''}$NH), 6.39 (d, J=9.0 Hz, 2H, H-3',5'), 6.03 (d, J=6.7 Hz, 1H, exchangeable with D$_2$O, $^4$NH), 4.31 (sextet, J=6.7 Hz, 1H, cyclopentyl CHN), 4.10 (m, 1H, pyrrolidinyl CHN), 3.95 and 3.92 (2 br, 2H, exchangeable with D$_2$O, NH$_2$), 3.39 (m, 1H, pyrrolidinyl CHN), 3.26 (m, 1H, pyrrolidinyl CHN), 3.15 (m, 1H, pyrrolidinyl CHN), 2.96 (m, 1H, pyrrolidinyl CHN), 2.13 (m, 1H, pyrrolidinyl), 2.04–1.95 (m, 2H, cyclopentyl), 1.84 (m, 1H, pyrrolidinyl), 1.77–1.65 (m, 2H, cyclopentyl), 1.62–1.44 (m, 4H, cyclopentyl), 1.39 (s, 9H, CH$_3$).

EXAMPLE 4

Synthesis of Pyruvates

1. Ethyl 2-(3,5-dichloropyridin-4-yl)-2-oxoacetate

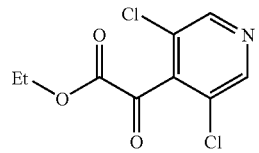

A solution of 4.44 g (30 mmol) of 3,5-dichloropyridine in 40 mL of THF is added dropwise over 30 minutes to a stirred solution of 23 mL (35 mmol) of 1.5 M LDA in 30 mL THF at −78° C. After a further 15 minutes at −78° C., a solution of 6.13 g (42 mmol) of diethyl oxalate in 15 mL THF is added, and the temperature is allowed to rise slowly to −20° C. The reaction mixture is then quenched with aqueous ammonium chloride, the solvent is removed, and the residue is worked up in EtOAc. Chromatography on silica, eluting with hexane/EtOAc (9:1), gives 2.4 g (32%) of the title compound as an oil.

$^1$H NMR (CDCl$_3$): δ 8.59 (s, 2H, H-2',6'), 4.44 (q, J=7.2 Hz, 2H, CH$_2$), 1.40 (t, J=7.0 Hz, 3H, CH$_3$).

$^{13}$C NMR (CDCl$_3$): δ 182.35 (s, CO), 158.42 (s, CO$_2$), 147.75 (d, C-2',6'), 141.94 (s, C-4'), 128.64 (s, C-3',5'), 63.79 (t, CH$_2$), 13.84 (q, CH$_3$).

high resolution electron immision mass spectroscopy (HREIMS) for C$_9$H$_7$Cl$_2$NO$_3$: M$^+$; 246.9803/248.9774 Found: 246.9801/248.9786.

2. Ethyl 2-(3,5-dichloro-2,6-dimethoxypyridin-4-yl)-2-oxoacetate

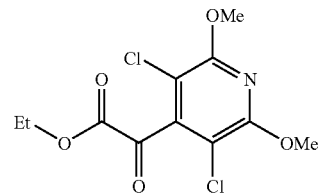

A solution of 5.20 g (25 mmol) of 3,5-dichloro-2,6-dimethoxypyridine (J. Bratt, H. Suschitzky, J.C.S. Perkin I, 1983:1689–1693) in 40 mL THF is added dropwise over 30 minutes to a solution of 20 mL (30 mmol) of 1.5 M LDA in 20 mL THF at −78° C. The resulting solution is stirred at −78° C. for 1 hour, and 4.5 mL (33 mmol) of diethyl oxalate is then added. The temperature is allowed to rise slowly to room temperature and aqueous ammonium chloride solution is added, and the solvent is removed under vacuum. The residue is extracted into EtOAc and chromatographed on SiO$_2$, eluting with hexane-EtOAc (9:1), to give 5.97 g (78%) of the title compound: mp (hexane) 195–196° C.

$^1$H NMR (CDCl$_3$): δ 4.41 (q, J=7.2 Hz, 2H, CH$_2$), 4.04 (s, 6H, CH$_3$O), 1.38 (t, J=7.1 Hz, 3H, CH$_3$).

$^{13}$C NMR (CDCl$_3$): δ 183.02 (s, CO), 158.50 (s, CO$_2$), 156.27 (s, C-2',6'), 145.99 (s, C-4'), 104.90 (s, C-3',5'), 63.51 (t, CH$_2$), 54.83 (q, CH$_3$O), 13.84 (q, CH$_3$).

Analysis calculated for C$_{11}$H$_{11}$Cl$_2$NO$_5$: C, 42.88; H, 3.60; N, 4.55. Found: C, 42.99; H, 3.46; N, 4.55.

3. Ethyl 2-(3,5-dibromopyridin-4-yl)-2-oxoacetate

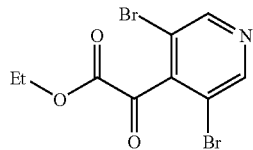

Lithiation of 4.74 g (20 mmol) of 3,5-dibromopyridine with LDA, according to the literature procedure (Y. G. Gu, E. K. Bayburt, *Tetrahedron Lett.*, 1996;37:2565–2568), followed by quenching with diethyl oxalate, and chromatography on silica, eluting with hexane/EtOAc (5:1), gives 4.53 g (67%) of the title compound.

$^1$H NMR (CDCl$_3$): δ 8.72 (s, 2H, H-2',6'), 4.44 (q, J=7.2 Hz, 2H, CH$_2$), 1.40 (t, J=7.1 Hz, 3H, CH$_3$).

$^{13}$C NMR (CDCl$_3$): δ 183.38 (s, CO), 157.66 (s, CO$_2$), 150.23 (d, C-2',6'), 145.93 (s, C-4'), 116.84 (s, C-3',5'), 63.78 (t, CH$_2$), 13.82 (q, CH$_3$).

HREIMS C$_9$H$_7$Br$_2$NO$_3$: M$^+$; 334.8793/336.8772/338.8752 Found: 334.8803/336.8771/338.8754.

4. Ethyl 2-(3,5-dimethoxyphenyl)-2-oxoacetate

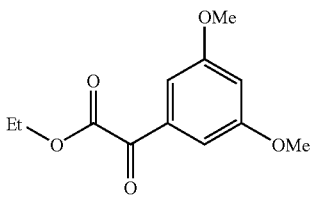

To a solution of 5.28 g (20 mmol) of 1-iodo-3,5-dimethoxybenzene (W. Riedhl, F. Imhof, *Justus Liebigs Ann. Chem.*, 1955;597:153–157) in 100 mL of THF at −78° C. is added 12.3 mL (21 mmol) of 1.7 M tert-BuLi in pentane, and after a further 5 minutes 4.4 g (30 mmol) of diethyl oxalate is added. After being allowed to warm to −20° C., the mixture is quenched with aqueous NH$_4$Cl, and the THF is removed under vacuum. Work-up in EtOAc, followed by chromatography on silica, eluting with hexane/EtOAc (9:1) gives 3.38 g (71%) of the title compound as an oil.

$^1$H NMR (CDCl$_3$): δ 7.13 (d, J=2.4 Hz, 2H, H-2',6'), 6.73 (d, J=2.3 Hz, 1H, H-4'), 4.44 (q, J=7.2 Hz, 2H, CH$_2$), 1.42 (t, J=7.1 Hz, 3H, CH$_3$).

$^{13}$C NMR (CDCl$_3$): δ 186.18 (s, CO), 163.77 (s, CO$_2$), 160.97 (s, C-3',5'), 134.11 (s, C-1'), 107.51 (d, C-2',4',6'), 62.30 (t, CH$_2$O), 55.63 (q, CH$_3$O), 14.08 (q, CH$_3$).

HREIMS C$_{12}$H$_{14}$O$_5$: M$^+$; 238.0841 Found: 238.0836.

EXAMPLE 5

Synthesis of 8H-Pteridin-7-ones 1. 8-Methyl-2-[[4-(morpholin-4-yl)phenyl]amino]-6-phenyl-8H-pteridin-7-one A mixture of 0.15 g (0.5 mmol) of 5-amino-4-(methylamino)-2-[[4-(morpholin-4-yl)phenyl]amino]pyrimidine (from Example 3(1)), 0.1 g (0.6 mmol) methyl benzoylformate and 0.25 mL HOAc in 15 mL EtOH is heated under reflux for 12 hours, and cooled to give 0.1 g (48%) of the title compound (Compound 1 in Tables 1 and 2): mp (EtOH) 302–304.5° C.

$^1$H NMR [(CD$_3$)$_2$SO]: δ 10.15 (br, 1H, exchangeable with D$_2$O, NH), 8.86 (s, 1H, H-4), 8.20–8.17 (m, 2H, H-2",6"), 7.70 (br d, J=6.1 Hz, 2H, H-2',6'), 7.50–7.48 (m, 3H, H-3",4",5"), 6.97 (d, J=9.0 Hz, 2H, H-3',5'), 3.75 (br t, J=4.7 Hz, 4H, CH$_2$O), 3.63 (s, 3H, CH$_3$N), 3.08 (br t, J=4.7 Hz, 4H, CH$_2$N).

Analysis calculated for C$_{23}$H$_{22}$N$_6$O$_2$: C, 66.65; H, 5.35; N, 20.28. Found: C, 66.39; H, 5.35; N, 20.49.

2. 6-(2,6-Dichlorophenyl)-8-methyl-2-[[4-(morpholin-4-yl)phenyl]amino]-8H-pteridin-7-one A mixture of 0.60 g (2 mmol) of 5-amino-4-(methylamino)-2-[[4-(morpholin-4-yl)phenyl]amino]pyrimidine, 0.74 g (3 mmol) ethyl 2-(2,6-dichlorophenyl)-2-oxoacetate (T. H. Kress and M. R. Leanna, *Synthesis*, 1988:803–805), and 0.3 mL HOAc in 25 mL of 2-methoxyethanol is heated under reflux for 16 hours before the solvent is removed under vacuum. The residue is extracted into EtOAc and, after being washed with water, the solution is dried over Na$_2$SO$_4$. Removal of the solvent and chromatography on silica, eluting with hexane/EtOAc 3:2 gives 0.36 g (37%) of the title compound (Compound 2 in Tables 1 and 2): mp (EtOH) 292–293° C.

$^1$H NMR [(CD$_3$)$_2$SO]: δ 10.31 (br, 1H, exchangeable with D$_2$O, NH, 8.90 (s, 1H, H-4), 7.70 (br, 2H, H-2',6'), 7.62 (br d, J=8.0 Hz, 2H, H-3",5"), 7.55 (dd, J=9.1, 6.9 Hz, 1H, H-4"), 6.98 (d, J=9.0 Hz, 2H, H-3',5'), 3.75 (br t, J=4.6 Hz, 4H, CH$_2$O), 3.63 (s, 3H, CH$_3$N), 3.09 (br t, J=4.7 Hz, 4H, CH$_2$N).

Analysis calculated for C$_{23}$H$_{20}$Cl$_2$N$_6$O$_2$: C, 57.15; H, 4.17; N, 17.39. Found: C, 57.17; H, 3.91; N, 17.37.

3. 6-(3,5-Dichloropyridin-4-yl)-8-methyl-2-[[4-(morpholin-4-yl)phenyl]amino]-8H-pteridin-7-one A mixture of 0.30 g (1 mmol) of 5-amino-4-(methylamino)-2-[[4-(morpholin-4-yl)phenyl]amino]pyrimidine, 0.37 g (1.5 mmol) of ethyl 2-(3,5-dichloropyridin-4-yl)-2-oxoacetate, and 0.3 mL HOAc in 15 mL 2-methoxyethanol as heated under reflux for 16 hours, and worked up as above in 2. Chromatography on alumina, eluting with CH$_2$Cl$_2$/EtOAc (4:1), gives 85 mg (18%) of the title compound (Compound 12 in Tables 1 and 2): mp (MeOH) 243–245° C.

$^1$H NMR [(CD$_3$)$_2$SO]: δ 10.41 (br, 1H, exchangeable with D$_2$O, NH), 8.93 (s, 1H, H-4), 8.84 (s, 2H, H-2",6"), 7.71 (br, 2H, H-2',6'), 6.98 (d, J=8.9 Hz, 2H, H-3',5'), 3.75 (br t, J=4.7 Hz, 4H, CH$_2$O), 3.64 (s, 3H, CH$_3$N), 3.09 (br t, J=4.7 Hz, 4H, CH$_2$N).

Analysis calculated for C$_{22}$H$_{19}$Cl$_2$N$_7$O$_2$.0.25H$_2$O C, 54.05; H, 4.02; N, 20.06. Found: C, 54.07; H, 3.63 N, 19.93.

4. 6-(3,5-Dichloro-2,6-dimethoxypyridin-4-yl)-8-methyl-2-[[4-(morpholin-4-yl)phenyl]amino]-8H-pteridin-7-one A mixture of 0.60 g (2 mmol) of 5-amino-4-(methylamino)-2-[[4-(morpholin-4-yl)phenyl]amino]pyrimidine, 1.23 g (4 mmol) of ethyl 2-(3,5-dichloro-2,6-dimethoxypyridin-4-yl)-2-oxoacetate, and 1 mL HOAc in 20 mL 2-methoxyethanol is heated under reflux for 16 hours. Workup in EtOAc, followed by chromatography on silica, eluting with hexane-EtOAc (3:2), gives 0.55 g (51%) of the title compound (Compound 18): mp (EtOH) 275–276° C.

$^1$H NMR [(CD$_3$)$_2$SO]: δ 10.36 (br, 1H, exchangeable with D$_2$O, NH), 8.91 (s, 1H, H-4), 7.70 (br, 2H, H-2',6'), 6.98 (d, J=8.9 Hz, 2H, H-3',5'), 4.07 (s, 6H, CH$_3$O), 3.75 (br t, J=4.8 Hz, 4H, CH$_2$O), 3.62 (s, 3H, CH$_3$N), 3.09 (br t, J=4.7 Hz, 4H, CH$_2$N).

Analysis calculated for C$_{24}$H$_{23}$Cl$_2$N$_7$O$_4$: C, 52.95; H, 4.26; N, 18.01. Found: C, 52.78; H, 4.13; N, 17.84.

5. 6-(3,5-Dibromopyridin-4-yl)-8-methyl-2-[[4-(morpholin-4-yl)phenyl]amino]-8H-pteridin-7-one A mixture of 0–30 g (1 mmol) of 5-amino-4-(methylamino)-2-[[4-(morpholin-4-yl)phenyl]amino]pyrimidine, 0.67 g (2 mmol) of ethyl 2-(3,5-dibromopyridin-4-yl)-2-oxoacetate (from preparation 17), and 0.5 mL of HOAc in 15 mL of 2-methoxyethanol is heated under reflux for 18 hours. Workup in EtOAc, followed by chromatography on silica, eluting with $CH_2Cl_2$/EtOAc (4:1), gives 0.15 g (26%) of the title compound (Compound 19): mp (EtOH) 204–206° C.

$^1$H NMR [$(CD_3)_2SO$]: δ 10.40 (br, 1H, exchangeable with $D_2O$, NH), 8.94 (s, 1H, H-4), 8.92 (s, 2H, H-2",6"), 7.70 (br, 2H, H-2',6'), 6.98 (d, J=8.7 Hz, 2H, H-3',5'), 3.75 (br t, J=4.7 Hz, 4H, $CH_2O$), 3.64 (s, 3H, $CH_3N$), 3.09 (br t, J=4.6 Hz, 4H, $CH_2N$).

Analysis calculated for $C_{22}H_{19}Br_2N_7O_2$: C, 46.10; H, 3.34; N, 17.10. Found: C, 46.14; H, 3.12; N, 17.09.

6. 2-[[4-[2-(Diethylamino)ethoxy]phenyl]amino]-8-methyl-6-phenyl-8H-pteridin-7-one A mixture of 0.165 g (0.5 mmol) of 5-amino-2-[[4-[2-(diethylamino)-ethoxy]phenyl]amino]-4-(methylamino)pyrimidine, 0.1 g (0.6 mmol) of methyl benzoylformate, and 0.2 mL of HOAc in 10 mL of EtOH is heated under reflux for 20 hours. Following removal of the solvent, the residue is treated with aqueous ammonia solution and extracted with EtOAc. Chromatography on alumina, eluting with EtOAc, gives 90 mg (40%) of the title compound (Compound 3): mp (MeOH) 162–165° C.

$^1$H NMR [$(CD_3)_2SO$]: δ 10.15 (br, 1H, exchangeable with $D_2O$, NH), 8.87 (s, 1H, H-4), 8.20–8.17 (m, 2H, H-2",6"), 7.71 (br d, J=8.2 Hz, 2H, H-2',6'), 7.50–7.48 (m, 3H, H-3",4",5"), 6.95 (d, J=8.9 Hz, 2H, H-3',5'), 4.00 (t, J=6.2 Hz, 2H, $CH_2O$), 3.62 (s, 3H, $CH_3N$), 2.77 (t, J=6.2 Hz, 2H, $CH_2N$), 2.55 (q, J=7.1 Hz, 4H, $CH_2N$), 0.98 (t, J=7.0 Hz, 6H, $CH_3$).

Analysis calculated for $C_{25}H_{28}N_6O_2$. C, 67.55; H, 6.35; N, 18.91. Found: C, 67.22; H, 6.22; N, 18.93.

7. 6-(2,6Dichlorophenyl)-2-[[4-[2-(diethylamino)ethoxy]phenyl]amino]-8-methyl-8H-pteridin-7-one A mixture of 0.165 g (0.5 mmol) of 5-amino-2-[[4-[2-(diethylamino)-ethoxy]phenyl]amino]4-(methylamino)pyrimidine, 0.16 g (0.65 mmol) of ethyl 2-(2,6-dichlorophenyl)-2-oxoacetate (T. H. Kress and M. R. Leanna, *Synthesis*, 1988:803–805), and 0.3 mL of HOAc in 10 mL of 2-methoxyethanol is heated under reflux for 18 hours. The reaction mixture is worked up as above in 6 to give 85 mg (33%) of the title compound (Compound 4): mp (MeOH) 156–161° C.

$^1$H NMR [$(CD_3)_2SO$]: δ 10.34 (br, 1H, exchangeable with $D_2O$, NH), 8.92 (s, 1H, H-4), 7.72 (br, 2H, H-2',6'), 7.63 (br d, J=7.9 Hz, 2H, H-3",5"), 7.55 (dd, J=9.1, 7.0 Hz, 1H, H-4"), 6.96 (d, J=8.9 Hz, 2-H, H-3',5'), 4.01 (t, J=6.2 Hz, 2H, $CH_2O$), 3.63 (s, 3H, $CH_3N$), 2.77 (t, J=6.2 Hz, 2H, $CH_2N$), 2.55 (q, J=7.1 Hz, 4H, $CH_2N$), 0.98 (t, J=7.0 Hz, 6H, $CH_3$).

Analysis calculated for $C_{25}H_{26}Cl_2N_6O_2$: C, 58.48; H, 5.10; N, 16.37. Found: C, 58.67; H, 5.04; N, 16.25.

8. 6-(3,5-Dichloropyridin-4-yl)-8-methyl-2-[[4-[2-(diethylamino)ethoxy]-phenyl]amino]-8H-pteridin-7-one A mixture of 0.465 g (1.4 mmol) of 5-amino-2-[[4-[2-(diethylamino)-ethoxy]-phenyl]amino]-4-(methylamino)pyrimidine, 0.69 g (2.8 mmol) of ethyl 2-(3,5-dichloropyridin-4-yl)-2-oxoacetate, and 0.5 mL of HOAc in 15 mL of 2-methoxyethanol is heated under reflux for 18 hours, and the reaction is worked up as above in 6 to give 0.11 g (15%) of the title compound (Compound 20): mp (MeOH) 179–180.5° C.

$^1$H NMR [$(CD_3)_2SO$]: δ 10.43 (br, 1H, exchangeable with $D_2O$, NH), 8.95 (s, 1H, H-4), 8.84 (s, 2H, H-2",6"), 7.72 (br, 2H, H-2',6'), 6.97 (d, J=8.9 Hz, 2H, H-3',5'), 4.02 (t, J=6.1 Hz, 2H, $CH_2O$), 3.63 (s, 3H, $CH_3N$), 2.78 (t, J=5.9 Hz, 2H, $CH_2N$), 2.56 (q, J=7.1 Hz, 4H, $CH_2N$), 0.98 (t, J=7.1 Hz, 6H, $CH_3$).

Analysis calculated for $C_{24}H_{25}Cl_2N_7O_2$: C, 56.04; H, 4.90; N, 19.06. Found: C, 56.34; H, 5.19; N, 19.32.

9. 6-(3,5-Dichloro-2,6-dimethoxypyridin-4-yl)-8-methyl-2-[[4-[2-(diethylamino)ethoxy]phenyl]amino]-8H-pteridin-7-one A mixture of 0.66 g (2 mmol) of 5-amino-2-[[4-[2-(diethylamino)-ethoxy]phenyl]amino]-4-(methylamino)pyrimidine, 1.23 g (4 mmol) of ethyl 2-(3,5-dichloro-2,6-dimethoxypyridin-4-yl)-2-oxoacetate, and 1 mL of HOAc in 20 mL of 2-methoxyethanol is heated under reflux for 16 hours. Workup as in 6 above gives 0.59 g (51%) of the title compound (Compound 21): mp (EtOH) 239–240° C.

$^1$H NMR [$(CD_3)_2SO$]: δ 10.38 (br, 1H, exchangeable with $D_2O$, NH), 8.92 (s, 1H, H-4), 7.72 (br, 2H, H-2',6'), 6.96 (d, J=9.0 Hz, 2H, H-3',5'), 4.04 (s, 6H, $CH_3O$), 4.01 (t, J=6.2 Hz, 2H, $CH_2O$), 3.62 (s, 3H, $CH_3N$), 2.77 (t, J=6.1 Hz, 2H, $CH_2N$), 2.55 (q, J=7.1 Hz, 4H, $CH_2N$), 0.98 (t, J=7.1 Hz, 6H, $CH_3$).

Analysis calculated for $C_{26}H_{29}C_{12}N_7O_4$: C, 54.36; H, 5.09; N, 17.07. Found: C, 54.17; H, 5.14; N, 16.94.

10. 2-[[4-(Diethylaminocarbonyl)phenyl]amino]-8-methyl-6-phenyl-8H-pteridin-7-one A mixture of 0.157 g (0.5 mmol) of 5-amino-2-[[4-(diethylaminocarbonyl)phenyl]amino]-4-(methylamino)pyrimidine, 0.1 g (6 mmol) methyl benzoylformate, and 0.2 mL of HOAc in 10 mL of EtOH is heated under reflux for 14 hours, and cooled to give 0.17 g (79%/o) of the title compound (Compound 5): mp (EtOH) 250–252° C.

$^1$H NMR [$(CD_3)_2SO$]: δ 10.46 (br, 1H, exchangeable with $D_2O$, NH), 8.96 (s, 1H, H-4), 8.21–8.18 (m, 2H, H-2",6"), 7.91 (d, J=8.6 Hz, 2H, H-2',6'), 7.52–7.50 (m, 3H, H-3",4", 5"), 7.38 (d, J=8.6 Hz, 2H, H-3',5'), 3.66 (s, 3H, $CH_3N$), 3.36 (m, 4H, $CH_2$), 1.12 (br t, J=6.5 Hz, 6H, $CH_3$).

Analysis calculated for $C_{24}H_{24}N_6O_2$: C, 67.27; H, 5.65; N, 19.61. Found: C, 67.23; H, 5.34; N, 19.68.

11. 6-(2,6-Dichlorophenyl)-2-[[4-(diethylaminocarbonyl)phenyl]amino]-8-methyl-8H-pteridin-7-one A mixture of 0.314 g (1 mmol) of 5-amino-2-[[4-(diethylaminocarbonyl)-phenyl]amino]-4-(methylamino)pyrimidine, 0.37 g (1.5 mmol) of ethyl 2-(2,6-dichlorophenyl)-2-oxoacetate (T. H. Kress, M. R. Leanna, *Synthesis*, 1988: 803–805), and 0.4 mL of HOAc in 15 mL of 2-methoxyethanol is heated under reflux for 16 hours. Following removal of the solvent, the residue is worked up in EtOAc and chromatographed on silica, eluting with $CH_2Cl_2$/EtOAc (4:1) to give 0.25 g (50%) of the title compound (Compound 6): mp (MeOH) 239–241° C.

$^1$H NMR [$(CD_3)_2SO$]: δ 10.63 (br, 1H, exchangeable with $D_2O$, NH), 9.01 (s, 1H, H-4), 7.91 (d, J 8.5 Hz, 2H, H-2',6'), 7.64 (br d, J=8.0 Hz, 2H, H-3",5"), 7.56 (dd, J=9.2, 6.9 Hz, 1H, H-4"), 7.39 (d, J=8.6 Hz, 2H, H-3',5'), 3.68 (s, 3H, $CH_3N$), 3.32 (m, 4H, $CH_2$), 1.12 (br t, J=6.4 Hz, 6H, $CH_3$).

Analysis calculated for $C_{24}H_{22}Cl_2N_6O_2$: C, 57.96; H, 4.46; N, 16.90. Found: C, 58.25; H, 4.36; N, 16.97.

12. 6-(3,5-Dichloropyridin-4-yl)-2-[[4-(diethylaminocarbonyl)phenyl]-amino]-8-methyl-8H-pteridin-7-one A mixture of 0.50 g (1.6 mmol) of 5-amino-2-[[4-(diethylaminocarbonyl)-phenyl]amino]-4-(methylamino)pyrimidine, 0.8 g (3.2 mmol) of ethyl 2-(3,5-dichloropyridin-4-yl)-2-oxoacetate, and 0.5 mL of HOAc in 20 mL of 2-methoxyethanol is heated under reflux for 16 hours. Workup in EtOAc, followed by chromatography on silica, eluting with EtOAc/hexane (3:2), gives 0.22 g (28%) of the title compound (Compound 13): mp (i-Pr$_2$O) 230–231° C.

$^1$H NMR [(CD$_3$)$_2$SO]: δ 10.71 (br, 1H, exchangeable with D$_2$O, NH), 9.04 (s, 1H, H-4), 8.85 (s, 2H, H-2″,6″), 7.91 (d, J=8.5 Hz, 2H, H-2',6'), 7.39 (d, J=8.6 Hz, 2H, H-3',5'), 3.68 (s, 3H, CH$_3$N), 3.33 (m, 4H, CH$_2$), 1.12 (br t, J=6.1 Hz, 6H, CH$_3$).

Analysis calculated for C$_{23}$H$_{21}$Cl$_2$N$_7$O$_2$: C, 55.43; H, 4.25; N, 19.67. Found: C, 55.12; H, 4.05; N, 19.44.

13. 6-(3,5Dichloro-2,6-dimethoxypyridin-4-yl)-2-[[4-(diethylaminocarbonyl)phenyl]amino]-8-methyl-8H-pteridin-7-one A mixture of 0.47 g (1.5 mmol) of 5-amino-2-[[4-(diethylaminocarbonyl)-phenyl]amino]-4-(methylamino)pyrimidine, 0.62 g (2 mmol) of ethyl 2-(3,5-dichloro-2,6-dimethoxypyridin-4-yl)-2-oxoacetate and 1.0 mL of HOAc in 20 mL of 2-methoxyethanol is heated under reflux for 16 hours. Workup in EtOAc, followed by chromatography on silica, eluting with hexane/EtOAc (1:1), gives 0.42 g (56%) of the title compound (Compound 22): mp (EtOH) 274–276° C.

$^1$H NMR [(CD$_3$)$_2$SO]: δ 10.66 (br, 1H, exchangeable with D$_2$O, NH), 9.02 (s, 1H, H-4), 7.91 (d, J=8.5 Hz, 2H, H-2',6'), 7.38 (d, J=8.6 Hz, 2H, H-3',5'), 4.05 (s, 6H, OCH$_3$), 3.67 (s, 3H, CH$_3$N), 3.33 (m, 4H, CH$_2$), 1.12 (br t, J=6.3 Hz, 6H, CH$_3$).

Analysis calculated for C$_{25}$H$_{25}$Cl$_2$N$_7$O$_4$: C, 53.77; H, 4.51; N, 17.56. Found: C, 53.68; H, 4.30; N, 17.39.

14. 8-Cyclopentyl-2-[[4-(morpholin-4-yl)phenyl]amino]-8H-pteridin-7-one

A mixture of 0.354 g (1 mmol) of 5-amino-4-(cyclopentylamino)-2-[[4-(morpholin-4-yl)phenyl]amino]pyrimidine, 0.26 g (2 mmol) of butyl glyoxylate (F. J. Wolf, J. Weijlard, *Org. Synth. Coll.*, 1963;4:124–125), and 0.5 mL of HOAc in 10 mL of EtOH is heated under reflux for 12 hours. Removal of the solvent and dilution with water gives the crude product which is chromatographed on alumina, eluting with CH$_2$Cl$_2$/EtOAc (4:1) to give 90 mg (23%) of the title compound (Compound 7): mp (MeOH) 182–184° C.

$^1$H NMR [(CD$_3$)$_2$SO]: δ 9.97 (br, 1H, exchangeable with D$_2$O, NH), 8.77 (s, 1H, H-4), 7.84 (s, 1H, H-6), 7.53 (br d, J=8.9 Hz, 2H, H-2',6'), 6.95 (d, J=9.0 Hz, 2H, H-3',5'), 5.65 (m, 1H, cyclopentyl CH), 3.74 (br t, J=4.8 Hz, 4H, CH$_2$O), 3.07 (br t, J=4.8 Hz, 4H, CH$_2$N), 2.28–2.18 (m, 2H, cyclopentyl), 1.93–1.74 (m, 4H, cyclopentyl), 1.64–1.53 (m, 2H, cyclopentyl).

Analysis calculated for C$_{21}$H$_{24}$N$_6$O$_2$: C, 64.27; H, 6.16; N, 21.41. Found: C, 64.39; H, 6.40; N, 21.55.

15. 8-Cyclopentyl-6-methyl-2-[[4-(morpholin-4-yl)phenyl]amino]-8H-pteridin-7-one A mixture of 0.32 g (0.9 mmol) of 5-amino-4-(cyclopentylamino)-2-[[4-(morpholin-4-yl)phenyl]amino]pyrimidine, 0.15 g (1.35 mmol) of 90% methyl pyruvate, and 0.2 mL HOAc in 10 mL of EtOH is heated under reflux for 12 hours. The mixture is cooled and diluted with water to give a precipitate which is collected and dried to give 0.28 g (76%) of the title compound (Compound 10): mp (EtOH) 230–234° C.

$^1$H NMR [(CD$_3$)$_2$SO]: δ 9.81 (br, 1H, exchangeable with D$_2$O, NH), 8.69 (s, 1H, H-4), 7.54 (br d, J=8.9 Hz, 2H, H-2',6'), 6.94 (d, J=9.1 Hz, 2H, H-3',5'), 5.69 (m, 1H, cyclopentyl CH), 3.74 (br t, J=4.8 Hz, 4H, CH$_2$O), 3.06 (br t, J=4.8 Hz, 4H, CH$_2$N), 2.34 (s, 3H, CH$_3$), 2.28–2.17 (m, 2H, cyclopentyl), 1.97–1.74 (m, 4H, cyclopentyl), 1.64–1.53 (m, 2H, cyclopentyl).

Analysis calculated for C$_{22}$H$_{26}$N$_6$O$_2$: C, 65.01; H, 6.45; N, 20.67. Found: C, 65.01; H, 6.56; N, 20.47.

16. 8-Cyclopentyl-2-[[4-(morpholin-4-yl)phenyl]amino]-5H,8H-pteridine-6,7-dione A mixture of 0.354 g (1 mmol) of 5-amino-4-(cyclopentylamino)-2-[[4-(morpholin-4-yl)phenyl]amino]pyrimidine and 5 mL (32 mmol) of diethyl oxalate in 20 mL of 2-ethoxyethanol is heated under reflux for 3 hours and then cooled to give 0.20 g (49%) of the title compound (Compound 23): mp (EtOH) 283–286° C. 1H NMR [(CD$_3$)$_2$SO]: δ 11.87 (br, 1H, exchangeable with D$_2$O, H-5), 9.29 (br, 1H, exchangeable with D$_2$O, $_2$NH), 8.12 (s, 1H, H-4), 7.50 (br d, J=9.0 Hz, 2H, H-2',6'), 6.90 (d, J=9.1 Hz, 2H, H-3',5'), 5.62 (pentet, J=8.8 Hz, 1H cyclopentyl CH), 3.74 (br t, J=4.7 Hz, 4H, CH$_2$O)), 3.03 (br t, J=4.7 Hz, 4H, CH$_2$N), 2.21–2.11 (m, 2H, cyclopentyl), 1.97–1.84 (m, 2H, cyclopentyl), 1.84–1.74 (m, 2H, cyclopentyl), 1.63–1.52 (m, 2H, cyclopentyl).

Analysis calculated for C$_{21}$H$_{24}$N$_6$O$_3$: C, 61.75; H, 5.92; N, 20.57. Found: C, 61.56; H, 5.86; N, 20.73.

17. 8-Cyclopentyl-2-[[4-(4methylpiperazin-1-yl)phenyl]amino]-8H-pteridin-7-one A mixture of 0.367 g (1 mmol) of 5-amino-4-(cyclopentylamino)-2-[[4-(4-methylpiperazin-1-yl)phenyl]amino]pyrimidine (from preparation 13), 0.26 g (2 mmol) of butyl glyoxylate (F. J. Wolf, J. Weijlard, *Org. Synth. Coll.*, 1963; 4:124–125) and 0.5 mL HOAc in 15 mL of EtOH is heated under reflux for 14 hours, and the solvent is removed under vacuum. The residue is diluted with aqueous ammonia solution and extracted into EtOAc. Chromatography on alumina, eluting with CH$_2$Cl$_2$/EtOAc (4:1), gives 0.26 g (64%) of the title compound (Compound 8): mp (MeOH) 208–211° C.

$^1$H NMR [(CD$_3$)$_2$SO]: δ 9.95 (br, 1H, exchangeable with D$_2$O, NH), 8.76 (s, 1H, H-4), 7.83 (s, 1H, H-6), 7.50 (br d, J=8.9 Hz, 2H, H-2',6'), 6.94 (d, J=9.0 Hz, 2H, H-3',5'), 5.65 (m, 1H, cyclopentyl CH), 3.10 (br t, J=4.9 Hz, 4H, CH$_2$N), 2.45 (br t, J=4.9 Hz, 4H, CH$_2$N), 2.27–2.18 (m, 2H, cyclopentyl), 2.22 (s, 3H, CH$_3$), 1.94–1.74 (m, 4H, cyclopentyl), 1.64–1.52 (m, 2H, cyclopentyl).

Analysis calculated for C$_{22}$H$_{27}$N$_7$O: C, 65.16; H, 6.71; N, 24.18. Found: C, 65.02; H, 6.96; N, 24.47.

18. 8-Cyclopentyl-6methyl-2-[[4-(4-methylpiperazin-1-yl)phenyl]amino]-8H-pteridin-7-one A mixture of 0.367 g (1 mmol) of 5-amino-4-(cyclopentylamino)-2-[[4-(4-methylpiperazin-1-yl)phenyl]amino]pyrimidine, 0.17 g (1.5 mmol) of 90% methyl pyruvate and 0.3 mL HOAc in 10 mL of EtOH is heated under reflux for 14 hours, and the solvent is removed under vacuum. Treatment of the residue with aqueous ammonia solution gives a solid which is collected and dried to give 0.39 g (93%) of the title compound (Compound 9): mp (MeOH) 210–211° C.

$^1$H NMR [(CD$_3$)$_2$SO]: δ 9.79 (br, 1H, exchangeable with D$_2$O, NH), 8.69 (s, 1H, H-4), 7.51 (br d, J=8.9 Hz, 2H, H-2',6'), 6.92 (d, J=8.9 Hz, 2H, H-3',5'), 5.69 (m, 1H, cyclopentyl CH), 3.09 (br t, J=4.8 Hz, 4H, CH$_2$N), 2.45 (br t, J=4.8 Hz, 4H, CH$_2$N), 2.34 (s, 3H, 6-CH$_3$), 2.28–2.15 (m, 2H, cyclopentyl), 2.22 (s, 3H, CH$_3$N) 1.95–1.73 (m, 4H, cyclopentyl), 1.64–1.53 (m, 2H, cyclopentyl).

Analysis calculated for C$_{23}$H$_{29}$N$_7$O: C, 65.85; H, 6.97; N, 23.37. Found: C, 65.85; H, 7.22; N, 23.66.

19. 8-Cyclopentyl-2-[[4-(4-methylpiperazin-1-yl)phenyl]amino]-5H,8H-pteridine-6,7-dione A mixture of 0.367 g (1 mmol) of 5-amino-4-(cyclopentylamino)-2-[[4-(4-methylpiperazin-1-yl)phenyl]amino]pyrimidine and 5 mL (32 mmol) of diethyl oxalate in 20 mL of 2-ethoxyethanol is heated under reflux for 3 hours, and cooled, to give 0.22 g (52%) of the title compound (Compound 24): mp (EtOH) 266–270° C.

$^1$H NMR [(CD$_3$)$_2$SO]: δ 11.86 (br, 1H, exchangeable with D$_2$O, H-5), 9.27 (br, 1H, exchangeable with D$_2$O, $^2$NH), 8.12 (s, 1H, H-4), 7.48 (br d, J=9.0 Hz, 2H, H-2',6'), 6.88 (d, J=9.1 Hz, 2H, H-3',5'), 5.62 (pentet, J=8.8 Hz, 1H cyclopentyl CH), 3.06 (br t, J=4.8 Hz, 4H, CH$_2$N), 2.45 (br t, J=4.8 Hz, 4H, CH$_2$N), 2.22 (s, 3H, CH$_3$), 2.19–2.11 (m, 2H, cyclopentyl), 1.99–1.86 (m, 2H, cyclopentyl), 1.84–1.74 (m, 2H, cyclopentyl), 1.63–1.52 (m, 2H, cyclopentyl).

Analysis calculated for C$_{22}$H$_{27}$N$_7$O$_2$.0.5H$_2$O: C, 61.37; H, 6.56; N, 22.78. Found: C, 61.08; H, 6.25; N, 22.90.

20. 8-Cyclopentyl-2-[(pyridin-4-yl)amino]-8H-pteridin-7-one

A mixture of 0.324 g (1.2 mmol) of 5-amino-4-(cyclopentylamino)-2-[(pyridin-4-yl)amino]pyrimidine, 0.31 g (2.4 mmol) of butyl glyoxylate (F. J. Wolf, J. Weijlard, *Org. Synth. Coll.*, 1963;4:124–125), and 0.5 mL of HOAc in 15 mL of EtOH is heated under reflux for 14 hours. Following removal of the solvent, the basified residue is worked up in EtOAc and chromatographed on alumina, eluting with EtOAc, to give 90 mg (24%) of the title compound (Compound 11): mp (MeOH) 236–238° C.

$^1$H NMR [(CD$_3$)$_2$SO]: δ 10.55 (br, 1H, exchangeable with D$_2$O, NH), 8.95 (s, 1H, H-4), 8.44 (br d, J=6.4 Hz, 2H, H-2',6'), 7.99 (s, 1H, H-6), 7.76 (br d, J=6.0 Hz, 2H, H-3',5'), 5.73 (pentet, J=8.8 Hz, 1H, cyclopentyl CH), 2.31–2.21 (m, 2H, cyclopentyl), 2.04–1.93 (m, 2H, cyclopentyl), 1.93–1.81 (m, 2H, cyclopentyl), 1.71–1.59 (m, 2H, cyclopentyl).

Analysis calculated for C$_{16}$H$_{16}$N$_6$O: C, 62.33; H, 5.23; N, 27.27. Found: C, 62.38; H, 5.21; N, 27.49.

21. 6-(3,5-Dimethoxyphenyl)-8-ethyl-2-[[4-[2-(diethylamino)ethoxyl]-phenyl]amino]-8H-pteridin-7-one A mixture of 0.96 g (2.8 mmol) of 5-amino-2-[[4-[2-(diethylamino)-ethoxy]phenyl]amino]-4-(ethylamino)pyrimidine pyrimidine, 0.83 g (35 mmol) of ethyl 2-(3,5-dimethoxyphenyl)-2-oxoacetate (from Example 4(2)), and 1 mL of acetic acid in 25 mL EtOH is heated under reflux for 14 hours, and the solvent is removed under vacuum. The residue is then dissolved in water and washed with EtOAc. The aqueous layer is made basic with aqueous ammonia, and the crude product is extracted into fresh EtOAc. Chromatography on alumina, eluting with hexane/EtOAc (1:1), then gives 0.81 g (56%) of the title compound (Compound 14): mp (MeOH) 154–155° C.

$^1$H NMR [(CD$_3$)$_2$SO]: δ 10.15 (br, 1H, exchangeable with D$_2$O, NH), 8.87 (s, 1H, H-4), 7.71 (br d, J=8.6 Hz, 2H, H-2',6'), 7.42 (d, J=2.3 Hz, 2H, H-2",6"), 6.94 (d, J=9.1 Hz,2H, H-3',5'), 6.63 (t, J=2.3 Hz, 1H, H-4"), 4.32 (q, J=7.0 Hz, 2H, CH$_2$N), 4.00 (t, J=6.2 Hz, 2H, CH$_2$O), 3.80 (s, 6H, CH$_3$O), 2.76 (t, J=6.2 Hz, 2H, CH$_2$N), 2.55 (q, J=7.1 Hz, 4H, CH$_2$N), 1.30 (t, J=7.0 Hz, 3H, CH$_3$), 0.98 (t, J=7.0 Hz, 6H, CH$_3$).

Analysis calculated for C$_{28}$H$_{34}$ClN$_6$O$_4$: C, 64.85; H, 6.61; N, 16.21. Found: C, 64.78; H, 6.63; N, 16.39.

22. 6-(3,5-Dimethoxyphenyl)-8-ethyl-2-[(pyridin-4-yl)amino]-8H-pteridin-7-one

A mixture of 0.46 g (2 mmol) of 5-amino-4-(ethylamino)-2-[(pyridin-4-yl) amino]pyrimidine, 0.71 g (3 mmol) of ethyl 2-(3,5-dimethoxyphenyl)-2-oxoacetate, and 1 mL of acetic acid is heated under reflux for 16 hours and cooled. The resulting precipitate is collected, washed with MeOH, and dried to give 0.38 g (47%) of the title compound (Compound 15): mp (EtOH) 245–246.5° C.

$^1$H NMR [(CD$_3$)$_2$SO]: δ 10.66 (br, 1H, exchangeable with D$_2$O, NH), 9.02 (s, 1H, H-4), 8.45 (dd, J=5.0, 1.4 Hz, 2H, H-2',6'), 7.83 (dd, J=5.1, 1.4 Hz, 2H, H-3',5'), 7.42 (d, J=2.5 Hz, 2H, H-2",6"), 6.67 (t, J=2.3 Hz, 1H, H-4"), 4.37 (q, J=7.1 Hz, 2H, CH$_2$N), 3.81 (s, 6H, CH$_3$O), 1.35 (t, J=7.1 Hz, 3H, CH$_3$).

Analysis calculated for C$_{21}$H$_{20}$N$_6$O$_3$: C, 62.37; H, 4.98; N, 20.78. Found: C, 62.60; H, 4.75; N, 20.56.

23. 8-Cyclopentyl-2-[[4-(piperazin-1-yl)phenyl]amino]-8H-pteridin-7-one a) 2-[[4-[4(tert-Butoxycarbonyl)piperazin-1-yl]phenyl]amino]-8-cyclopentyl-8H-pteridin-7-one

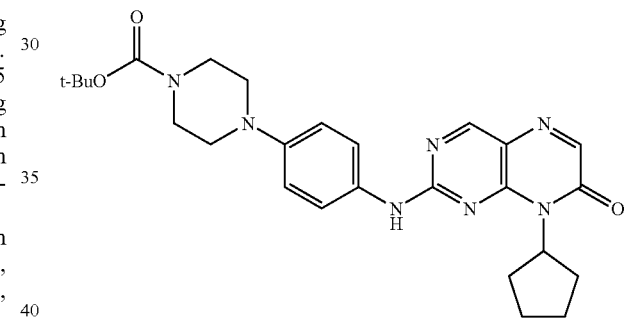

52

A mixture of 0.82 g (1.8 mmol) of 5-amino-2-[[4-[4-(tert-butoxycarbonyl)piperazin-1-yl]phenyl]amino]-4-(cyclopentylamino)pyrimidine (from preparation 14A), 0.52 g (4 mmol) of butyl glyoxylate (F. J. Wolf, J. Weijlard, *Org. Synth. Coll.*, 1963;4:124–125), and 0.5 mL HOAc in 15 mL of EtOH is heated under reflux for 14 hours, and the solvent is removed under vacuum. The residue is diluted with aqueous ammonia solution and extracted into EtOAc. Chromatography on silica, eluting with hexane/EtOAc (3:2) gave 0.38 g (43%) of the title compound (Compound 52): mp (MeOH) 215–217° C.

$^1$H NMR [(CD$_3$)$_2$SO]: δ 9.96 (br, 1H, exchangeable with D$_2$O, NH), 8.77 (s, 1H, H-4), 7.84 (s, 1H, H-6), 7.50 (dd, J=9.1, 3.2 Hz, 2H, H-2',6'), 6.94 (d, J=9.1 Hz, 2H, H-3',5'), 5.66 (m, 1H, cyclopentyl CH), 3.46 (br t, J=4.9 Hz, 4H, CH$_2$N), 3.05 (br t, J=5.0 Hz, 4H, CH$_2$N), 2.28–2.18 (m, 2H, cyclopentyl), 1.94–1.74 (m, 4H, cyclopentyl), 1.64–1.53 (m, 2H, cyclopentyl), 1.42 (s, 9H, CH$_3$).

Analysis calculated for C$_{26}$H$_{33}$N$_7$O$_3$: C, 63.53; H, 6.77; N, 19.94. Found: C, 63.55; H, 6.90; N, 19.82.

b) A solution of 0.15 g (0.3 mmol) of 2-[[4-[4-(tert-butoxycarbonyl)-piperazin-1-yl]phenyl]amino]-8-cyclopentyl-8H-pteridin-7-one in 10 mL of CH$_2$Cl$_2$ is treated with 1 mL of trifluoroacetic acid, and the mixture is stirred at room temperature for 3 hours. After removal of the solvent under vacuum, the residue is triturated with aqueous ammonia to give 0.112 g (94%) of the title compound (Compound 16): mp (MeOH) 215–217° C.

$^1$H NMR [(CD$_3$)$_2$SO]: δ 9.92 (br, 1H, exchangeable with D$_2$O, NH), 8.76 (s, 1H, H-4), 7.83 (s, 1H, H-6), 7.50 (dd, J=9.0, 3.4 Hz, 2H, H-2',6'), 6.92 (d, J=9.1 Hz, 2H, H-3',5'), 5.65 (m, 1H, cyclopentyl CH), 3.00 (br t, J=4.9 Hz, 4H, CH$_2$N), 2.82 (br t, J=4.9 Hz, 4H, CH$_2$N), 2.28–2.18 (m, 2H, cyclopentyl), 1.94–1.73 (m, 4H, cyclopentyl), 1.64–1.52 (m, 2H, cyclopentyl).

Analysis calculated for C$_{21}$H$_{25}$N$_7$O.0.5 H$_2$O: C, 62.98; H, 6.54; N, 24.48. Found: C, 63.32; H, 6.29; N, 24.34.

24. 2-[[4-(3-Aminopyrrolidin-1-yl)phenyl]amino]-8-cyclopentyl-8H-pteridin-7-one a) 2-[[4-[3-(tert-Butoxycarbonylamino)pyrrolidin-1-yl]phenyl]amino]-8-cyclopentyl-8H-pteridin-7-one

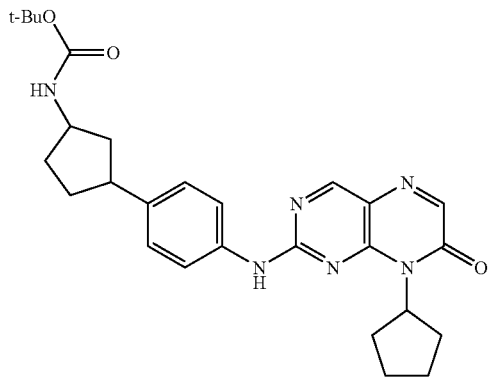

53

A mixture of 0.70 g (1.5 mmol) of 5-amino-2-[[4-[3-(tert-butoxycarbonylamino)pyrrolidin-1-yl]phenyl]amino]-4-(cyclopentylamino)-pyrimidine, 0.52 g (4 mmol) of butyl glyoxylate (F. J. Wolf, J. Weijlard, Org. Synth. Coll., 1963; 4:124–125) and 0.5 mL HOAc in 15 mL of EtOH is heated under reflux for 14 hours, and the solvent is removed under vacuum. The residue is diluted with aqueous ammonia solution and extracted into EtOAc. Chromatography on silica, eluting with hexane/EtOAc (3:2), gives 0.21 g (28%) of the title compound (Compound 53): mp (MeOH) 226–228° C.

$^1$H NMR [(CD$_3$)$_2$SO]: δ 9.83 (br, 1H, exchangeable with D$_2$O, $^2$NH), 8.73 (s, 1H, H-4), 7.80 (s, 1H, H-6), 7.44 (dd, J=8.8, 3.4 Hz, 2H, H-2',6'), 7.17 (br d, J=6.5 Hz, 1H, exchangeable with D$_2$O, $^{3''}$H), 6.51 (d, J=8.9 Hz, 2H, H-3', 5'), 5.63 (m, 1H, cyclopentyl CHN), 4.13 (m, 1H, pyrrolidinyl CHN), 3.45 (m, 1H, pyrrolidinyl), 3.34 (m, 1H, pyrrolidinyl), 3.22 (m, 1H, pyrrolidinyl), 3.03 (m, 1H, pyrrolidinyl), 2.28–2.19 (m, 2H, cyclopentyl), 2.16 (m, 1 H, pyrrolidinyl), 1.93–1.73 (m, 5H, (m, 1H, pyrrolidinyl and cyclopentyl), 1.63–1.52 (m, 2H, cyclopentyl), 1.40 (s, 9H, CH$_3$).

Analysis calculated for C$_{26}$H$_{33}$N$_7$O$_3$: C, 63.53; H, 6.77; N, 19.94. Found: C, 63.54; H, 6.74; N, 19.82.

b) A solution of 0.14 g (0.28 mmol) of 2-[[4-[3-(tert-butoxycarbonyl amino)pyrrolidin-1-yl]phenyl]amino]-8-cyclopentyl-8H-pteridin-7-one (from example 23) in 10 mL CH$_2$Cl$_2$ is treated with 1 mL of trifluoroacetic acid, and the resulting mixture is stirred at room temperature for 3 hours. After removal of the solvent, the residue is triturated with aqueous ammonia to give 0.11 g (100%) of the title compound (Compound 17): mp (MeOH$_{(aq)}$) 197–200° C.

$^1$H NMR [(CD$_3$)$_2$SO]: δ 9.82 (br, 1H, exchangeable with D$_2$O, NH), 8.72 (s, 1H, H-4), 7.80 (s, 1H, H-6), 7.42 (dd, J=8.9, 3.4 Hz, 2H, H-2',6'), 6.48 (d, J=8.9 Hz, 2H, H-3',5'), 5.62 (m, 1H, cyclopentyl CHN), 3.55 (br pentet, J=5.8 Hz, 1H, pyrrolidinyl CHN), 3.39 (m, 1H, pyrrolidinyl), 3.34 (m, 1H, pyrrolidinyl), 3.22 (m, 1H, pyrrolidinyl), 2.86 (m, 1H, pyrrolidinyl), 2.28–2.18 (m, 2H, cyclopentyl), 2.07 (m, 1H, pyrrolidinyl), 1.98–1.66 (m, 7H, NH$_2$, pyrrolidinyl and cyclopentyl), 1.63–1.52 (m, 2H, cyclopentyl).

Analysis calculated for C$_{21}$H$_{25}$N$_7$O.0.66 H$_2$O: C, 62.51; H, 6.58; N, 24.30. Found: C, 62.41; H, 6.55; N, 24.33.

Additional compounds prepared in an analogous fashion are as follows:

8-Cyclopentyl-5-methyl-2-(4-piperazin-1-yl-phenylamino)-5,8-dihydro-6H-pteridin-7-one;

2-[4-(4-Acetyl-piperazin-1-yl)-phenylamino]-8-cyclopentyl-5-methyl-5,8-dihydro-6H-pteridin-7-one;

N-{1-[4-(8-Cyclopentyl-5-methyl-7-oxo-5,6,7,8-tetrahydro-pteridin-2-ylamino)-phenyl]-pyrrolidin-3-yl}-3,3-dimethyl-butyramide;

8-Cyclopentyl-5-methyl-2-(4-morpholin-4-yl-phenylamino)-5,8-dihydro-6H-pteridin-7-one;

8-cyclopentyl-2-{4-[4-(2-hydroxy-ethyl)-piperazin-1-yl]-phenylamino}-5-methyl-5,8-dihydro-6H-pteridin-7-one;

8-cyclopentyl-2-{4-[4-(2-hydroxy-ethyl)-3,5-dimethyl-piperazin-1-yl]-phenylamino}-5-methyl-5,8-dihydro-6H-pteridin-7-one;

1-[4-(8-Isopropyl-5-methyl-7-oxo-5,6,7,8-tetrahydro-pteridin-2-ylamino)-phenyl]-.pyrrolidine-3-carboxylic acid butylamide;

{4-[4-(8-Cyclopentyl-5-methyl-7-oxo-5,6,7,8-tetrahydro-pteridin-2-ylamino)-phenyl]-piperazin-1-yl}-acetic acid; and 6-(2,6-Dichloro-3-hydroxy-phenyl)-8-methyl-2-(4-morpholin-4-yl-phenylamino)-8H-pteridin-7-one.

EXAMPLE 6

The pharmaceutical utilities of pteridines of this invention are established by the following assays for kinase inhibition.

1. Wee 1 OY Assay

These kinase assays are carried out on 96-well filter plates (Millpore, Cat. MADPN0B50) in 50 μL kinase assay buffer (50 mM Tris, pH 8.0, 10 mM NaCl, 10 mM MgCl$_2$, 10 μM ATP with 0.25 μCi [r-32P]ATP, 1 mM DTT) with 0.1 μg purified N-terminal truncated Wee 1 and 6 μg poly(Orn, Tyr)4:1 (Sigma, P4534). The assay is started by adding ATP and incubating at room temperature for 20 minutes with shaking. The reactions are terminated by adding 50 μL ice-cold 20% TCA (trichloracetic acid) with 0.1 M sodium pyrophosphate and shaking the resultant mixture for 1 minute. The plate is then incubated at 4° C. for 1 hour to allow protein to precipitate. These plates are then washed 5 times with 200 μL ice-cold 10% TCA and with 0.1 M sodium pyrophosphate per wash. Twenty-five microliters scintillation liquid is then added to each well, and the plate is counted in Wallac's MicroBeta counter 1450. Results for several of the pteridines of the invention are shown in Table 2.

2. Cyclin-dependent Kinase 4 (CDK4) Assay

Enzyme assays for IC$_{50}$ determinations (Table 1) and kinetic evaluation were performed in 96-well filter plates (Millipore MADVN6550) The total volume was 0.1 mL containing a final concentration of 20 mM TRIS (tris[hydroxymethyl]aminomethane), at pH 7.4, 50 mM NaCl, 1 mM dithiothreitol, 10 mM mgCl$_2$, 25 μM ATP containing 0.25

µCi of [$^{32}$P]ATP, 20 ng of cdk4/cyclin D$_1$ complex, 1 µg of retinoblastoma and appropriate dilutions of a compound of the present invention. All components except the ATP were added to the wells, and the plate was placed on a plate mixer for 2 minutes. The reaction was started by adding [$^{32}$P]ATP and the plate incubated at 25° C. for 15 minutes. The reaction was terminated by addition of 0.1 mL of 20% TCA. The plate was kept at 4° C. for at least 1 hour to allow the substrate to precipitate. The wells were then washed five times with 0.2 mL of 10% TCA and $^{32}$p incorporation determined with a beta plate counter (Wallac Inc., Gaithersburg, Md.).

3. PDGF and FGF Receptor Tyrosine Kinase Assays

Full-length cDNAs for the mouse PDGF-β and human FGF-1 (flg) receptor tyrosine kinases were obtained from J. Escobedo and prepared as described in *J. Biol. Chem.*, 1991;262:1482–1487. PCR primers were designed to amplify a fragment of DNA that codes for the intracellular tyrosine kinase domain. The fragment was inserted into a baculovirus vector, cotransfected with AcMNPV DNA, and the recombinant virus isolated. SF9 insect cells were infected with the virus to overexpress the protein, and the cell lysate was used for the assay. Assays were performed in 96-well plates (100 µL/incubation/well), and conditions were optimized to measure the incorporation of $^{32}$P from γ$^{32}$P-ATP into a glutamate-tyrosine co-polymer substrate. Briefly, to each well was added 82.5 µL of incubation buffer containing 25 mM Hepes (pH 7.0), 150 mM NaCl, 0.1% Triton X-100, 0.2 mM PMSF, 0.2 mM Na$_3$VO$_4$, 10 mM MnCl$_2$, and 750 µg/mL of Poly (4:1) glutamate-tyrosine followed by 2.5 µL of inhibitor and 5 µL of enzyme lysate (7.5 µg/µL FGF-TK or 6.0 µg/µL PDGF-TK) to initiate the reaction. Following a 10 minute incubation at 25° C., 10 mL of γ$^{32}$P-ATP (0.4 µCi plus 50 µM ATP) was added to each well, and samples were incubated for an additional 10 minutes at 25° C. The reaction was terminated by the addition of 100 µL of 30% TCA containing 20 mM sodium pyrophosphate and precipitation of material onto glass fiber mats (Wallac). Filters were washed three times with 15% TCA containing 100 mM sodium pyrophosphate, and the radioactivity retained on the filters counted in a Wallac 1250 Betaplate reader. Nonspecific activity was defined as radioactivity retained on the filters following incubation of samples with buffer alone (no enzyme). Specific enzymatic activity (enzyme plus buffer) was defined as total activity minus nonspecific activity. The concentration of a compound that inhibited specific activity by 50% (IC$_{50}$) was determined based on the inhibition curve.

4. C-src Kinase Assays

C-src kinase was purified from baculovirus infected insect cell lysates using an antipeptide monoclonal antibody directed against the N-terminal amino acids (amino acids 2–17) of c-src. The antibody, covalently linked to 0.65 µm latex beads, was added to a suspension of insect cell lysis buffer comprised of 150 mM NaCl, 50 mM Tris pH 7.5, 1 mM DTT, 1% NP-40, 2 mM EGTA, 1 mM sodium vanadate, 1 mM PMSF, 1 µg/mL each of leupeptin, pepstatin, and aprotinin. Insect cell lysate containing c-src protein was incubated with these beads for 3 to 4 hours at 4° C. with rotation. At the end of the lysate incubation, the beads were rinsed three times in lysis buffer, resuspended in lysis buffer containing 10% glycerol, and frozen. These latex beads were thawed, rinsed three times in assay buffer (40 mM Tris, pH 7.5, 5 mM mgCl$_2$) and suspended in the same buffer. In a Millipore 96-well plate with a 0.65 µm polyvinylidine membrane bottom were added the reaction components: 10 µL C-src beads, 10 µL of 2.5 mg/mL poly GluTyr substrate, 5 µM ATP containing 0.2 µCi labeled $^{32}$P-ATP, 5 µL DMSO containing inhibitors or as a solvent control, and buffer to make the final volume 125 µL. The reaction was started at room temperature by addition of the ATP and quenched 10 minutes later by the addition of 125 µL of 30% TCA, 0.1 M sodium pyrophosphate for 5 minutes on ice. The plate was then filtered and the wells washed with two 250 mL aliquots of 15% TCA, 0.1 M pyrophosphate. The filters were then punched, counted in a liquid scintillation counter, and the data examined for inhibitory activity in comparison to a known inhibitor such as erbstatin. The method is also described in *J. Med. Chem.*, 1994;37:598–609.

5. Cyclin-dependent Kinase Assays (cdk2/cyclinE, cdk2/cyclinA, cdc2/cyclinB)

Enzyme assays for IC$_{50}$ determinations and kinetic evaluation were performed in a 96-well filter plate (Millipore MADVN6550) in a total volume of 0.1 mL of 20 mM TRIS, pH 7.4, 50 mM NaCl, 1 mM dithiothreitol, 10 mM MgCl$_2$, 12 µM ATP containing 0.25 µCi of [$^{32}$P]ATP, 20 ng of enzyme (either cdk2/cyclinE, cdk2/cyclinA, or cdc2/cyclinB), 1 µg retinoblastoma, and appropriate dilutions of the particular invention compound. All components except the ATP were added to the wells, and the plate was placed on a plate mixer for 2 minutes. The reaction was begun by addition of [$^{32}$P]ATP, and the plate was incubated at 25° C. for 15 minutes. The reaction was terminated by addition of 0.1 mL of 20% TCA. The plate was kept at 4° C. for at least 1 hour to allow the substrate to precipitate. The wells were then washed five times with 0.2 mL of 10% TCA and $^{32}$P incorporation determined using a beta plate counter (Wallac Inc., Gaithersburg, Md.).

Several of the invention compounds exhibited good inhibitory activity when evaluated in the foregoing assays, as illustrated by the data in Table 2.

In the table, the columns have the following meanings:

C-src means C-src kinase
FGF means full length fibroblast growth factor receptor kinase
PDGF means platelet derived growth factor kinase
CDK4D means cyclin dependent kinase 4/cyclin D$_1$ complex
CDK2A means cyclin dependent kinase 2/cyclin A complex
CDK1B means cyclin dependent kinase 1/cyclin B complex
CDK2E means cyclin dependent kinase 2/cyclin E complex
IC$_{50}$ means the concentration of test compound in micromoles to inhibit the activity of a specified kinase by 50 percent.

TABLE 2

| Cmpd No. | WEE1OY IC$_{50}$ (µm) | C-src IC$_{50}$ (µm) | FGF IC$_{50}$ (µm) | PDGF IC$_{50}$ (µm) | CDK4D IC$_{50}$ (µm) | CDK2A IC$_{50}$ (µm) | CDK1B IC$_{50}$ (µm) | CDK2E IC$_{50}$ (µm) |
|---|---|---|---|---|---|---|---|---|
| 1 | >50 | >50 | >50 | >50 | | | | |
| 2 | 0.1445 | 0.057 | >50 | 7.7 | | | | |
| 3 | >50 | 1.53 | 54% @ 5 | 7.55 | | | | |

TABLE 2-continued

| Cmpd No. | WEE1OY IC$_{50}$ (μm) | C-src IC$_{50}$ (μm) | FGF IC$_{50}$ (μm) | PDGF IC$_{50}$ (μm) | CDK4D IC$_{50}$ (μm) | CDK2A IC$_{50}$ (μm) | CDK1B IC$_{50}$ (μm) | CDK2E IC$_{50}$ (μm) |
|---|---|---|---|---|---|---|---|---|
| 4 | 0.8605 | 0.015 | 69% @ 5 | 0.70 | | | | |
| 5 | >50 | >50 | 38% @ 5 | >50 | | | | |
| 6 | 0.987 | 0.29 | 0.05 | 3.13 | | | | |
| 7 | >50 | 8.47 | 33% @ 5 | 11.95 | 0.06 | 0.064 | | 0.65 |
| 8 | >50 | 3.35 | 41% @ 0.5 | 6 | 0.041 | 0.26 | | 0.95 |
| 9 | >50 | 3 | 41% @ 0.5 | 59% @ 5 | 0.047 | 2.78 | | 41 |
| 10 | >50 | 34 | 57% @ 50 | >50 | 0.44 | 1.84 | | 8 |
| 11 | >50 | 11 | 31% @ 5 | >50 | 1.25 | 0.036 | 0.354 | 0.05 |
| 12 | 1.01 | 0.38 | | 25.4 | | | | |
| 13 | 4.49 | 0.50 | 17% @ 5 | | | | | |
| 14 | | | 30 | | | | | |
| 15 | | | | | | | | |
| 16 | | 3.3 | | | 0.007 | 0.18 | 0.75 | 0.61 |
| 17 | | | | 2.19 | 0.0435 | 0.094 | 0.4 | 1.9 |
| 18 | >50 | 20 | 0.23 | | | | | |
| 19 | 7.4 | 1.45 | | | | | | |
| 20 | 7.07 | 0.12 | | | | | | |
| 21 | >50 | 6.8 | 0.054 | | | | | |
| 22 | >50 | 47 | 0.16 | | | | | |
| 23 | | | | | | | | |
| 24 | | 4.35 | | | | | | |
| 52 | | >50 | | | 1.8 | 0.53 | | 4.5 |
| 53 | | | | | | | | |
| 62 | 0.077 | | | | | | | |

The following examples further illustrate typical pharmaceutical formulations provided by this invention.

Example 7

Preparation of Pharmaceutical Compositions

1. A pharmaceutical formulation in the form of hard gelatin capsules for oral administration are prepared using the following ingredients:

| | Quantity (mg/capsule) |
|---|---|
| Active compound | 250 |
| Starch powder | 200 |
| Magnesium stearate | 10 |
| Total | 460 mg |

The above ingredients are mixed and filled into hard gelatin capsules in 460 mg quantities. A typical active ingredient is 6-(3,4-diethoxyphenyl)-2-[4-(2-diethylaminoethoxy)-phenylamino]-8-n-butyl-8H-pteridin-7-one. The composition is administered from 2 to 4 times a day for treatment of postsurgical restenosis.

2. Formulation for Oral Suspension

| Ingredient | Amount |
|---|---|
| 8-Sec-butyl-2-phenylamino-8H-6-(2,3-difluorophenyl)-7-one | 500 mg |
| Sorbitol solution (70% N.F.) | 40 mL |
| Sodium benzoate | 150 mg |
| Saccharin | 10 mg |
| Cherry Flavor | 50 mg |
| Distilled water q.s. ad | 100 mL |

The sorbitol solution is added to 40 mL of distilled water, and the naphthyridine is suspended therein. The saccharin, sodium benzoate, and flavoring are added and dissolved. The volume is adjusted to 100 mL with distilled water. 10 Each milliliter of syrup contains 5 mg of active ingredient. The suspension is well-suited for the oral treatment and prevention of atherosclerosis.

3. Tablets each containing 60 mg of active ingredient

| | |
|---|---|
| Active ingredient | 60 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1.0 mg |
| Total | 150 mg |

The active ingredients, starch and cellulose, are passed through a No. 45 mesh U.S. sieve and mixed thoroughly. The solution of polyvinylpyrrolidone is mixed with the resultant powders and then passed through a No. 14 mesh U.S. sieve. The granules are dried at 50–60° C. and passed through a No. 18 mesh U.S. sieve. The sodium carboxymethyl starch, magnesium stearate, and talc, previously passed through a No. 60 mesh U.S. sieve, are then added to the granules which, after mixing, are compressed on a tablet machine to yield tablets each weighing 150 mg.

A typical active ingredient utilized in the above preparation is the compound of Example 6 (7). This formulation is well-suited for prevention and treatment of psoriasis.

4. A parenteral composition suitable for administration by injection is prepared by dissolving 100 mg of 6-pyridine-2yl-8-(1-ethylpropyl)-2-[4-(4-methylpiperazin-1-yl)-phenylamino]-8H-pteridine-7-one in 250 mL of 0.9% aqueous sodium chloride solution and adjusting the pH of the solution to about 7.0. This formulation is well-suited for the treatment of cancer, for example breast cancer, leukemia, prostate cancer, bladder carcinomas, colorectal cancer, and small-cell lung carcinoma.

5. Preparation for Suppositories

A mixture of 500 mg of 2-(3-methyl-4-fluorophenyl)amino-8-cyclohexyl-8H-pteridine-7-one hydrochloride and 1500 mg of theobroma oil are blended to uniformity at 60° C. The mixture is cooled to 24° C. in tapered molds. Each suppository will weigh about 2 g and can be administered from 1 to 2 times each day for treatment of inflammatory bowel disease.

6. Topical Preparation

| Ingredient | Amount (mg) |
| --- | --- |
| 8-Methyl-2-(4-methoxyphenylamino)-6-phenyl-8H-pteridin-7-one | 20 |
| Propylene Glycol | 100 |
| White Petrolatum | 500 |
| Cetearyl Alcohol | 50 |
| Glyceryl Stearate | 100 |
| PEG 100 Stearate | 100 |
| Ceteth-20 | 50 |
| Monobasic Sodium Phosphate | 80 |
| TOTAL | 1000 |

The above ingredients are blended to uniformity into a cream and applied topically for treatment of melanoma.

What is claimed is:

1. A compound of the formula

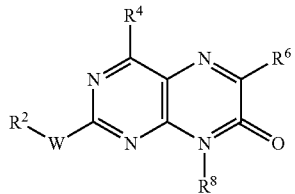

and pharmaceutically acceptable salts thereof, wherein:
W is NH;
$R^2$ is:
$C_1$–$C_{10}$ alkyl, $C_2$–$C_{10}$ alkenyl, $C_2$–$C_{10}$ alkynyl, $C_3$–$C_{10}$ cycloalkyl, $(CH_2)_n$-aryl, $COR^4$, $(CH_2)_n$-heteroaryl, and $(CH_2)_n$-heterocyclyl, wherein each of the foregoing alkyl, alkenyl, alkynyl, cycloalkyl, aryl, heteroaryl, and heterocyclyl groups can be unsubstituted or substituted with from 1 to 5 substituent groups selected from:
(a) halogen
(b) amino, alkylamino, and dialkylamino
(c) alkoxy, aminoalkoxy, alkylaminoalkoxy, and dialkylaminoalkoxy
(d) phenyl, substituted phenyl, phenoxy, and substituted phenoxy
(e) hydroxy
(f) thio, alkylthio
(g) cyano
(h) nitro
(i) alkanoyl, aminoalkanoyl, alkylaminoalkanoyl, and dialkylaminoalkanoyl
(j) aminocarbonyl, alkylaminocarbonyl, and dialkylaminocarbonyl (k) amino-$C_3$–$C_7$ cycloalkylcarbonyl, alkylamino-$C_3$–$C_7$ cycloalkylcarbonyl, and dialkylamino-$C_3$–$C_7$ cycloalkylcarbonyl
(l) COZ, $CO_2$Z, SOZ, $SO_2$Z, and $PO_3$Z, where Z is hydrogen, hydroxy, alkoxy, SOZ, lower alkyl, substituted alkyl, amino, alkylamino, dialkylamino, piperidinyl, substituted piperidinyl, morpholinyl, substituted morpholinyl, piperazinyl, and substituted piperazinyl
(m) a carbocyclic group containing from 3 to 7 ring members, one or two of which may be a heteroatom selected from O or N, and wherein the carbocyclic group may be substituted with one, two, or three substituent groups selected from:
(1) halogen
(2) hydroxy
(3) alkyl, aminoalkyl, alkyl and dialkylaminoalkyl
(4) trifluoromethyl
(5) alkoxy
(6) amino, alkylamino, dialkylamino, alkanoylamino
(7) COZ, $CO_2$Z, SOZ, $SO_2$Z, or $PO_3$Z
(8) aryl
(9) heteroaryl
(10) $(CH_2)_n$ morpholino
(11) $(CH_2)_n$ piperazinyl
(12) $(CH_2)_n$ piperadinyl
(13) $(CH_2)_n$ tetrazolyl
(n) trifluoromethyl;
$R^4$ and $R^6$ are:
(a) the same or different and are independently hydrogen, halogen, lower alkyl, or lower alkoxy, substituted alkyl, $(CH_2)_n$-alkenyl, $(CH_2)_n$-alkynyl, $(CH_2)_n$-cyano, amino, aminoalkoxy, phenoxy, hydroxy, trifluoromethyl, mono- or dialkylamino, mono- or dialkylaminoalkoxy, thiol, thioalkyl, nitrile, nitro, carboxylic acid, carboxylic acid esters, carboxamides, $SO_2$Z, $PO_3$Z, COZ, $CO_2$Z, SOZ, aminoalkanoyl, aminocarbonyl, amino-$C_3$–$C_7$-cycloalkylcarbonyl, and N-mono- or N,N-dialkylaminocarbonyl, provided that $R^6$ is not hydroxy;
(b) the same or different and are independently $(CH_2)_n$-aryl, $(CH_2)_n$-heteroaryl, arylalkyl, or heteroarylalkyl, wherein each aryl and heteroaryl is unsubstituted or substituted with up to five groups selected from halogen, hydroxy, lower alkyl, substituted alkyl, alkenyl, substituted alkenyl, alkynyl, substituted alkynyl, lower alkoxy, amino, mono- or dialkylamino, trifluoromethyl, thiol, thioalkyl, nitrile, nitro, carboxylic acid, carboxylic acid esters, carboxamide, $SO_3$Z, and $PO_3$Z;
$R^8$ is:
(a) hydrogen, lower alkyl, substituted alkyl, $(CH_2)_n$-alkenyl, substituted alkenyl, $(CH_2)_n$-alkynyl, substituted alkynyl, or a $(CH_2)_n$-carbocyclic group containing from 3–7 members, up to two of which members are hetero atoms selected from oxygen and nitrogen, wherein the carbocyclic group is unsubstituted or substituted with one, two or three groups selected from the group consisting of halogen, hydroxy, lower alkyl, lower alkoxy, acetoxy, amino, COZ, $CO_2$Z, SOZ, $SO_2$Z, $PO_3$Z, mono- or dialkylamino, aryl and heteroaryl;
(b) $(CH_2)_n$-aryl, $(CH_2)_n$-heteroaryl, arylalkyl, or heteroarylalkyl, wherein each aryl or heteroaryl is unsubstituted or substituted with up to five groups selected from the group consisting of halogen, hydroxy, lower alkyl, substituted alkyl, lower alkoxy, amino, mono- or dialkylamino, trifluoromethyl, alkenyl, substituted alkenyl, alkynyl, substituted alkynyl, thiol, thioalkyl, nitrile, nitro, carboxylic acid, carboxylic acid esters, carboxamides, COZ, $CO_2Z$, SOZ, $SO_2Z$, and $PO_3Z$; and n is an integer from 0 to 6, and provided that $R^8$ is other than hydrogen or $C_1$–$C_3$ alkyl when $R^2$ is methyl, ethyl, or acetyl.

2. A compound of the formula

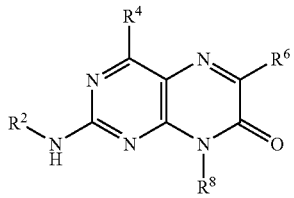

and pharmaceutically acceptable salts thereof, wherein:
$R^2$ is:
$C_1$–$C_{10}$ alkyl, $C_2$–$C_{10}$ alkenyl, $C_2$–$C_{10}$ alkynyl, $C_3$–$C_{10}$ cycloalkyl, $(CH_2)_n$-aryl, $COR^4$, $(CH_2)_n$-heteroaryl, and $(CH_2)_n$-heterocyclyl, wherein each of the foregoing alkyl, alkenyl, alkynyl, cycloalkyl, aryl, heteroaryl, and heterocyclyl groups can be unsubstituted or substituted with from 1 to 5 substituent groups selected from:
(a) halogen
(b) amino, alkylamino, and dialkylamino
(c) alkoxy, aminoalkoxy, alkylaminoalkoxy, and dialkylaminoalkoxy
(d) phenyl, substituted phenyl, phenoxy, and substituted phenoxy
(e) hydroxy
(f) thio, alkylthio
(g) cyano
(h) nitro
(i) alkanoyl, aminoalkanoyl, alkylaminoalkanoyl, and dialkylaminoalkanoyl
(j) aminocarbonyl, alkylaminocarbonyl, and dialkylaminocarbonyl
(k) amino-$C_3$–$C_7$ cycloalkylcarbonyl, alkylamino-$C_3$–$C_7$ cycloalkylcarbonyl, and dialkylamino-$C_3$–$C_7$ cycloalkylcarbonyl
(l) COZ, $CO_2Z$, SOZ, $SO_2Z$, and $PO_3Z$, where Z is hydrogen, hydroxy, alkoxy, lower alkyl, substituted alkyl, amino, alkylamino, dialkylamino, piperidinyl, substituted piperidinyl, morpholinyl, substituted morpholinyl, piperazinyl, and substituted piperazinyl
(m) a carbocyclic group containing from 3 to 7 ring members, one or two of which may be a heteroatom selected from O or N, and wherein the carbocyclic group may be substituted with one, two, or three substituent groups selected from:
(1) halogen
(2) hydroxy
(3) alkyl, aminoalkyl, alkyl and dialkylaminoalkyl
(4) trifluoromethyl
(5) alkoxy
(6) amino, alkylamino, dialkylamino, alkanoylamino
(7) COZ, $CO_2Z$, SOZ, $SO_2Z$, or $PO_3Z$
(8) aryl
(9) heteroaryl
(10) $(CH_2)_n$ morpholino
(11) $(CH_2)_n$ piperazinyl
(12) $(CH_2)_n$ piperadinyl
(13) $(CH_2)_n$ tetrazolyl
(n) trifluoromethyl;
$R^4$ and $R^6$ are:
(a) the same or different and are independently hydrogen, halogen, loweralkyl, or lower alkoxy, substituted alkyl, $(CH_2)_n$-alkenyl, substituted alkenyl, $(CH_2)_n$-alkynyl, substituted alkynyl, $(CH_2)_n$-cyano, amino, aminoalkoxy, phenoxy, hydroxy, trifluoromethyl, mono- or dialkylamino, mono- or dialkylaminoalkoxy, thiol, thioalkyl, nitrile, nitro, carboxylic acid, carboxylic acid esters, carboxamides, $SO_2Z$, $PO_3Z$, COZ, $CO_2Z$, SOZ, aminoalkanoyl, aminocarbonyl, amino-$C_3$–$C_7$-cycloalkylcarbonyl, and N-mono- or N,N-dialkylaminocarbonyl, provided that $R^6$ is not hydroxy;
(b) the same or different and are independently $(CH_2)_n$-aryl, $(CH_2)_n$-heteroaryl, arylalkyl, or heteroarylalkyl, wherein each aryl and heteroaryl is unsubstituted or substituted with up to five groups selected from halogen, hydroxy, lower alkyl, substituted alkyl, alkenyl, substituted alkenyl, alkynyl, substituted alkynyl, lower alkoxy, amino, mono- or dialkylamino, trifluoromethyl, thiol, thioalkyl, nitrile, nitro, carboxylic acid, carboxylic acid esters, carboxamide, $SO_3Z$, and $PO_3Z$;
$R^8$ is:
(a) hydrogen, lower alkyl, substituted alkyl, $(CH_2)_n$-alkenyl, substituted alkenyl, $(CH_2)_n$-alkynyl, substituted alkynyl, or a $(CH_2)_n$-carbocyclic group containing from 3–7 members, up to two of which members are hetero atoms selected from oxygen and nitrogen, wherein the carbocyclic group is unsubstituted or substituted with one, two or three groups selected from the group consisting of halogen, hydroxy, lower alkyl, lower alkoxy, acetoxy, amines, carboxylic acids, carboxylic esters, carboxyamides, amino, COZ, $CO_2Z$, SOZ, $SO_2Z$, $PO_3Z$, mono- or dialkylamino, aryl and heteroaryl;
(b) $(CH_2)_n$-aryl, $(CH_2)_n$-heteroaryl, arylalkyl, or heteroarylalkyl, wherein each aryl or heteroaryl is unsubstituted or substituted with up to five groups selected from the group consisting of halogen, hydroxy, lower alkyl, substituted alkyl, lower alkoxy, amino, mono- or dialkylamino, trifluoromethyl, alkenyl, substituted alkenyl, alkynyl, substituted alkynyl, thiol, thioalkyl, nitrile, nitro, carboxylic acid, carboxylic acid esters, carboxamides, COZ, $CO_2Z$, SOZ, $SO_2Z$, and $PO_3Z$; and n is an integer from 0 to 6, and provided that $R^8$ is other than hydrogen or $C_1$–$C_3$ alkyl when $R^2$ is methyl, ethyl, or acetyl.

3. A compound of the formula

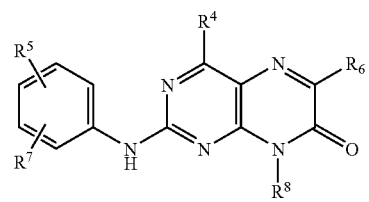

and pharmaceutically acceptable salts thereof, wherein:
$R^5$ and $R^7$ are the same or different and selected from:
(a) hydrogen, halogen, amino, aminoalkoxy, lower alkoxy, phenoxy, hydroxy, thiol, thioalkyl, nitrile, nitro, phenyl, substituted phenyl, heteroaryl, trifluoromethyl, mono- or dialkylamino, mono- or dialkylaminoalkoxy, alkanoylamino, aminocarbonyl, amino-$C_3$–$C_7$-cycloalkylcarbonyl, and N-mono- or N,N-dialkylaminocarbonyl;
(b) $CO_2Z$, COZ, SOZ, $SO_2Z$ or $PO_3Z$, where Z is H, lower alkyl, hydroxy, alkoxy, substituted alkyl, amino, mono- or dialkylamino, piperidinyl, morpholinyl or piperazinyl (with or without substitution);
(c) lower alkyl unsubstituted or substituted with one or two groups selected from lower alkoxy, halogen, amino, hydroxy, mono- or dialkylamino, carboxylic acid, carboxamide, carboxylic acid ester, aryl or a carbocyclic group containing from 3–7 members, up to two of which members are hetero atoms selected from oxygen and nitrogen, wherein the carbocyclic group is unsubstituted or substituted with one, two or three groups independently selected from the group consisting of halogen, hydroxy, lower alkyl, lower alkoxy, amino, or mono- or dialkylamino;
(d) a carbocyclic group containing from 3–7 members, up to two of which members are hetero atoms selected from oxygen and nitrogen, wherein the carbocyclic group is unsubstituted or substituted with one, two or three groups independently selected from the group consisting of halogen, hydroxy, lower alkyl, branched alkyl, trifluoromethyl, lower alkoxy, amino, mono- or dialkylamino, aryl, heteroaryl, carboxylic acid, carboxamide, carboxylic acid ester, aryl, heteroaryl, morpholinoalkyl, piperazinylalkyl, piperadinylalkyl, tetrazolylalkyl, aminoalkyl and alkanoylamino;

$R^4$ and $R^6$ are:
(a) the same or different and are independently hydrogen, halogen, lower alkyl, or lower alkoxy, substituted alkyl, $(CH_2)_n$-alkenyl, $(CH_2)_n$-alkynyl, $(CH_2)_n$-cyano, amino, aminoalkoxy, phenoxy, hydroxy, trifluoromethyl, mono- or dialkylamino, mono- or dialkylaminoalkoxy, thiol, thioalkyl, nitrile, nitro, carboxylic acid, carboxylic acid esters, carboxamides, $SO_2Z$, $PO_3Z$, COZ, $CO_2Z$, SOZ, aminoalkanoyl, aminocarbonyl, amino-$C_3$–$C_7$-cycloalkylcarbonyl, and N-mono- or N,N-dialkylaminocarbonyl, provided that $R^6$ is not hydroxy;
(b) the same or different and are independently $(CH_2)_n$-aryl, $(CH_2)_n$-heteroaryl, arylalkyl, or heteroarylalkyl, wherein each aryl and heteroaryl is unsubstituted or substituted with up to five groups selected from halogen, hydroxy, lower alkyl, substituted alkyl, alkenyl, substituted alkenyl, alkynyl, substituted alkynyl, lower alkoxy, amino, mono- or dialkylamino, trifluoromethyl, thiol, thioalkyl, nitrile, nitro, carboxylic acid, carboxylic acid esters, carboxamide, COZ, $CO_2Z$, SOZ, $SO_2Z$, and $PO_3Z$;

$R^8$ is:
(a) hydrogen, lower alkyl, substituted alkyl, $(CH_2)_n$-alkenyl, substituted alkenyl, $(CH_2)_n$-alkynyl, substituted alkynyl, or a $(CH_2)_n$-carbocyclic group containing from 3–7 members, up to two of which members are hetero atoms selected from oxygen and nitrogen, wherein the carbocyclic group is unsubstituted or substituted with one, two or three groups selected from the group consisting of halogen, hydroxy, lower alkyl, lower alkoxy, acetoxy, amino, carboxylic acids, esters, amides, mono- or dialkylamino, aryl and heteroaryl;
(b) $(CH_2)_n$-aryl, $(CH_2)_n$-heteroaryl, arylalkyl, or heteroarylalkyl, wherein each aryl or heteroaryl is unsubstituted or substituted with up to five groups selected from the group consisting of halogen, hydroxy, lower alkyl, substituted alkyl, lower alkoxy, amino, mono- or dialkylamino, trifluoromethyl, alkenyl, substituted alkenyl, alkynyl, substituted alkynyl, thiol, thioalkyl, nitrile, nitro, carboxylic acid, carboxylic acid esters, carboxamides, COZ, $CO_2Z$, SOZ, $SO_2Z$, and $PO_3Z$; and n is an integer from 0 to 6, and provided that $R^8$ is other than hydrogen or $C_1$–$C_3$ alkyl when $R^2$ is methyl, ethyl, or acetyl.

4. A compound of the formula

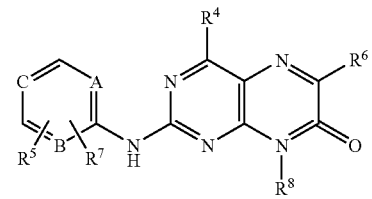

and pharmaceutically acceptable salts thereof, wherein:
A, B, and C are the same or different and represent N or CH, provided that at least one of A, B, or C is CH;
$R^5$ and $R^7$ are the same or different and selected from:
(a) hydrogen, halogen, amino, aminoalkoxy, lower alkoxy, hydroxy, trifluoromethyl, mono- or dialkylamino, mono- or dialkylaminoalkoxy, alkanoylamino, carbamoyl, amino-$C_3$–$C_7$-cycloalkylcarbonyl, N-mono- or N,N-dialkylcarbamoyl, or
(b) COZ, $CO_2Z$, SOZ, $SO_2Z$, $PO_3Z$, where Z is H, lower alkyl, hydroxy, alkoxy, amino, mono- or dialkylamino, piperidinyl, morpholinyl or piperazinyl, or
(c) lower alkyl unsubstituted or substituted with one or two groups selected from lower alkoxy, halogen, amino, hydroxy, mono- or dialkylamino, aryl or a carbocyclic group containing from 3–7 members, up to two of which members are hetero atoms selected from oxygen and nitrogen, wherein the carbocyclic group is unsubstituted or substituted with one, two or three groups independently selected from the group consisting of halogen, hydroxy, lower alkyl, lower alkoxy, amino, or mono- or dialkylamino, or
(d) a carbocyclic group containing from 3–7 members, up to two of which members are hetero atoms selected from oxygen and nitrogen, wherein the carbocyclic group is unsubstituted or substituted with one, two or three groups independently selected from the group consisting of halogen, hydroxy, lower alkyl, trifluoromethyl, lower alkoxy, amino, mono- or dialkylamino, aryl, heteroaryl, morpholinoalkyl, piperazinylalkyl, piperadinylalkyl, tetrazolylalkyl, aminoalkyl and alkanoylamino;

$R^4$ and $R^6$ are the same or different and are selected from:
(a) the same or different and are independently hydrogen, halogen, lower alkyl, or lower alkoxy, substituted alkyl, $(CH_2)_n$-alkenyl, $(CH_2)_n$-alkynyl, $(CH_2)_n$-cyano, amino, aminoalkoxy, phenoxy, hydroxy, trifluoromethyl, mono- or dialkylamino, mono- or dialkylaminoalkoxy, thiol, thioalkyl, nitrile, nitro, carboxylic acid, carboxylic acid esters, carboxamides, $SO_2Z$, $PO_3Z$, COZ, $CO_2Z$, SOZ, aminoalkanoyl, aminocarbonyl, amino-$C_3$–$C_7$-cycloalkylcarbonyl, and N-mono- or N,N-dialkylaminocarbonyl, provided that $R^6$ is not hydroxy;
(b) the same or different and are independently $(CH_2)_n$-aryl, $(CH_2)_n$-heteroaryl, arylalkyl, or heteroarylalkyl, wherein each aryl and heteroaryl is unsubstituted or substituted with up to five groups selected from halogen, hydroxy, lower alkyl, substituted alkyl, alkenyl, substituted alkenyl, alkynyl, substituted alkynyl, lower alkoxy, amino, mono- or dialkylamino, trifluoromethyl, thiol, thioalkyl, nitrile, nitro, carboxylic acid, carboxylic acid esters, carboxamide, COZ, $CO_2Z$, SOZ, $SO_2Z$, and $PO_3Z$;

$R^8$ is:

(a) hydrogen, lower alkyl, substituted alkyl, $(CH_2)_n$-alkenyl, substituted alkenyl, $(CH_2)_n$-alkynyl, substituted alkynyl, or a $(CH_2)_n$-carbocyclic group containing from 3–7 members, up to two of which members are hetero atoms selected from oxygen and nitrogen, wherein the carbocyclic group is unsubstituted or substituted with one, two or three groups selected from the group consisting of halogen, hydroxy, lower alkyl, lower alkoxy, acetoxy, amino, carboxylic acids, esters, amides, mono- or dialkylamino, aryl and heteroaryl;

(b) $(CH_2)_n$-aryl, $(CH_2)_n$-heteroaryl, arylalkyl, or heteroarylalkyl, wherein each aryl or heteroaryl is unsubstituted or substituted with up to five groups selected from the group consisting of halogen, hydroxy, lower alkyl, substituted alkyl, lower alkoxy, amino, mono- or dialkylamino, trifluoromethyl, alkenyl, substituted alkenyl, alkynyl, substituted alkynyl, thiol, thioalkyl, nitrile, nitro, carboxylic acid, carboxylic acid esters, carboxamides, COZ, $CO_2Z$, SOZ, $SO_2Z$, and $PO_3Z$.

5. A compound which is selected from:

8-Methyl-2-[[4-(morpholin-4-yl)phenyl)]amino]-6-phenyl-8H-pteridin-7-one;
6-(2,6-Dichlorophenyl)-8-methyl-2-[[4-(morpholin-4-yl)phenyl]amino]-8H-pteridin-7-one;
6-(3,5-Dichloropyridin-4-yl)-8-methyl-2-[[4-(morpholin-4-yl)phenyl]amino]-8H-pteridin-7-one;
6-(3,5-Dichloro-2,6-dimethoxypyridin-4-yl)-8-methyl-2-[[4-(morpholin-4-yl)phenyl]amino]-8H-pteridin-7-one;
6-(3,5-Dibromopyridin-4-yl)-8-methyl-2-[[4-(morpholin-4-yl)phenyl]amino]-8H-pteridin-7-one;
2-[[4-[2-(Diethylamino)ethoxy]phenyl]amino]-8-methyl-6-phenyl-8H-pteridin-7-one;
6-(2,6-Dichlorophenyl)-2-[[4-[2-(diethylamino)ethoxy]phenyl]-amino]-8-methyl-8H-pteridin-7-one;
6-(3,5-Dichloropyridin-4-yl)-8-methyl-2-[[4-[2-(diethylamino)-ethoxy]phenyl]amino]-8H-pteridin-7-one;
6-(3,5-Dichloro-2,6-dimethoxypyridin-4-yl)-8-methyl-2-[[4-[2-(diethylamino)ethoxy]phenyl]amino]-8H-pteridin-7-one;
2-[[4-(Diethylaminocarbonyl)phenyl]amino]-8-methyl-6-phenyl-8H-pteridin-7-one;
6-(2,6-Dichlorophenyl)-2-[[4-(diethylaminocarbonyl)phenyl]-amino]-8-methyl-8H-pteridin-7-one;
6-(3,5-Dichloropyridin-4-yl)-2-[[4-(diethylaminocarbonyl)phenyl]-amino]-8-methyl-8H-pteridin-7-one;
6-(3,5-Dichloro-2,6-dimethoxypyridin-4-yl)-2-[[4-(diethylaminocarbonyl)phenyl]amino]-8-methyl-8H-pteridin-7-one;
8-Cyclopentyl-2-[[4-(morpholin-4-yl)phenyl]amino]-8H-pteridin-7-one;
8-Cyclopentyl-6-methyl-2-[[4-(morpholin-4-yl)phenyl]amino]-8H-pteridin-7-one;
8-Cyclopentyl-2-[[4-(4-methylpiperazin-1-yl)phenyl]amino]-8H-pteridin-7-one;
8-Cyclopentyl-6-methyl-2-[[4-(4-methylpiperazin-1-yl)phenyl]-amino]-8H-pteridin-7-one;
8-Cyclopentyl-2-[(pyridin-4-yl)amino]-8H-pteridin-7-one;
2-[[4-(3-Aminopyrrolidin-1-yl)phenyl]amino]-8-cyclopentyl-8H-pteridin-7-one;
8-Cyclopentyl-2-[[4-(piperazin-1-yl)phenyl]amino]-8H-pteridin-7-one;
6-(3,5-Dimethoxyphenyl)-8-ethyl-2-[(pyridin-4-yl)amino]-8H-pteridin-7-one;
6-(3,5-Dimethoxyphenyl)-8-ethyl-2-[[4-[2-(diethylamino)ethoxy]-phenyl]amino]-8H-pteridin-7-one;
2-[[4-[4-(tert-butoxycarbonyl)piperazin-1-yl]phenyl]amino]-8-cyclopentyl-8H-pteridin-7-one;
2-[[4-[3-(tert-butoxycarbonylamino)pyrrolidin-1-yl]phenyl]-amino]-8-cyclopentyl-8H-pteridin-7-one;
8-Cyclopentyl-2-(4-fluoro-3-methyl-phenylamino)-8H-pteridin-7-one;
2-(3-Chloro-4-fluoro-phenylamino)-8-cyclopentyl-8H-pteridin-7-one;
8-Cyclohexyl-2-(4-fluoro-3-methyl-phenylamino)-8H-pteridin-7-one;
8-Cyclopentyl-2-{3-fluoro-4-[4-(3-morpholin-4-yl-propyl)-piperidin-1-yl]-phenylamino}-8H-pteridin-7-one;
8-Cyclopentyl-2-{4-[4-(3-morpholin-4-yl-propyl)-piperidin-1-yl]-phenylamino)-8H-pteridin-7-one;
8-Cyclopentyl-2-{4-[4-(3-piperazin-1-yl-propyl)-piperidin-1-yl]-phenylamino}-8H-pteridin-7-one;
8-Cyclopentyl-2-(4-{4-[3-(1H-tetrazol-5-yl)-propyl]-piperidin-1-yl}-phenylamino)-8H-pteridin-7-one;
8-Cyclopentyl-2-(4-fluoro-3-methyl-phenylamino)-6-methyl-8H-pteridin-7-one;
5-(8-Cyclopentyl-7-oxo-7,8-dihydro-pteridin-2-ylamino)-2-methyl-isoindole-1,3-dione;
N-[4-(8-Cyclopentyl-7-oxo-7,8-dihydro-pteridin-2-ylamino)-phenyl]-propionamide;
N-[4-(8-Cyclopentyl-6-methyl-7-oxo-7,8-dihydro-pteridin-2-ylamino)-phenyl]-propionamide;
2-(3-Chloro-4-piperazin-1-yl-phenylamino)-8-cyclopentyl-8H-pteridin-7-one-;
2-[3-Chloro-4-(3-chloro-pyrrolidin-1-yl)-phenylamino]-8-cyclopentyl-8H-pteridin-7-one;
2-[3-Chloro-4-(3-chloro-4-trifluoromethyl-pyrrolidin-1-yl)-phenylamino]-8-cyclopentyl-8H-pteridin-7-one;
N-{1-[4-(8-Cyclopentyl-7-oxo-7,8-dihydro-pteridin-2-ylamino)-phenyl]-pyrrolidin-3-yl}-3 ,3-dimethyl-butyramide;
2-(4-[3-(1-Amino-1-methyl-ethyl)-pyrrolidin-1-yl]-3-chloro-phenylamino}-8-cyclopentyl-8H-pteridin-7-one;
2-[4-(3-Amino-cyclopentanecarbonyl)-phenylamino]-8-cyclopentyl-8H-pteridin-7-one;
8-Cyclopentyl-2-(4-methanesulfonyl-phenylamino)-6-methyl-8H-pteridin-7-one;
4-(8-Cyclopentyl-6-methyl-7-oxo-7,8-dihydro-pteridin-2-ylamino)-benzenesulfonamide;
8-Cyclopentyl-6-methyl-2-[4-(piperidine-1-sulfonyl)-phenylamino]-8H-pteridin-7-one;
6-(2,6-Dichloro-3-methoxyphenyl)-8-methyl-2-{[4-(morpholin-4-yl)phenyl]amino}-8H-pteridin-7-one; and
6-(2,6-Dichloro-3-hydroxyphenyl)-8-methyl-2-{[4-(morpholin-4-yl)phenyl]amino}-8H-pteridin-7-one.

6. A compound which is selected from:
6-(2,6-Dichloro-3-hydroxy-phenyl)-8methyl-2-(4-morpholin-4-ylamino)-8H-pteridine-7-one.

7. A pharmaceutical formulation comprising a compound of claim 1 in combination with a pharmaceutically acceptable carrier, diluent, or excipient.

* * * * *